(12) United States Patent
Aaronson et al.

(10) Patent No.: US 11,273,151 B2
(45) Date of Patent: Mar. 15, 2022

(54) METHODS OF TREATING TUMORS AND CANCER, AND IDENTIFYING CANDIDATE SUBJECTS FOR SUCH TREATMENT

(71) Applicant: ICAHN SCHOOL OF MEDICINE AT MOUNT SINAI, New York, NY (US)

(72) Inventors: Stuart Aaronson, New York, NY (US); Albino Troilo, New York, NY (US); Davide Esposito, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/773,463

(22) PCT Filed: Nov. 3, 2016

(86) PCT No.: PCT/US2016/060342
§ 371 (c)(1),
(2) Date: May 3, 2018

(87) PCT Pub. No.: WO2017/079442
PCT Pub. Date: May 11, 2017

(65) Prior Publication Data
US 2018/0318272 A1 Nov. 8, 2018

Related U.S. Application Data

(60) Provisional application No. 62/335,642, filed on May 12, 2016, provisional application No. 62/250,801, filed on Nov. 4, 2015.

(51) Int. Cl.
| | | |
|---|---|---|
| *A61K 31/4409* | (2006.01) | |
| *A61K 31/519* | (2006.01) | |
| *C12Q 1/6886* | (2018.01) | |
| *C07K 14/47* | (2006.01) | |
| *A61K 45/06* | (2006.01) | |
| *A61P 35/00* | (2006.01) | |
| *A61K 31/551* | (2006.01) | |

(52) U.S. Cl.
CPC ........ *A61K 31/4409* (2013.01); *A61K 31/519* (2013.01); *A61K 31/551* (2013.01); *A61K 45/06* (2013.01); *A61P 35/00* (2018.01); *C07K 14/4746* (2013.01); *C12Q 1/6886* (2013.01); *C12Q 2600/106* (2013.01); *C12Q 2600/156* (2013.01)

(58) Field of Classification Search
CPC ............ A61K 2300/00; A61K 31/4409; A61K 31/519; A61K 31/551; A61K 45/06; A61P 35/00; C07K 14/4746; C12Q 1/6886; C12Q 2600/106; C12Q 2600/156
See application file for complete search history.

(56) References Cited

U.S. PATENT DOCUMENTS

| | | | |
|---|---|---|---|
| 2006/0079493 A1 * | 4/2006 | Fritz | A61K 31/33 514/183 |
| 2009/0318684 A1 | 12/2009 | Sebti et al. | |
| 2015/0071930 A1 * | 3/2015 | Lee | A61K 39/39558 424/138.1 |

FOREIGN PATENT DOCUMENTS

| | | | | |
|---|---|---|---|---|
| WO | WO-2009065232 A1 | * | 5/2009 | A61K 31/404 |
| WO | WO-2011/031308 | * | 3/2011 | |
| WO | 2015/069512 A1 | | 5/2015 | |

OTHER PUBLICATIONS

Wei et al. (Arch Immunol. Ther. Exp 2016, 64, 259-278) (Year: 2016).*
Ying et al. (Mol Cancer Ther 2006, 5, (9), Sep. 2006) (Year: 2006).*
Anastassiadis et al. (Nature Biotechnology, 29, 11, Nov. 2011, p. 1039-1046). (Year: 2011).*
Bao et al. (PLOS One, Nov. 2012, 7, 11, pp. 1-9) (Year: 2012).*
Cao et al. (Jiepouxue Zazhi, 2013, 36(3). (Year: 2013).*
Walerych et al. (Carcinogenesis, 33, 11, 2007-2017, 2012). (Year: 2012).*
International Search Report and Written Opinion for corresponding Application No. PCT/US2016/060342 (dated Mar. 23, 2017).
Zhang et al., "Tumour-Associated Mutant p53 Drives the Warburg Effect," Nat. Comm. 4(2935):1-15 (2013).
Extended European Search Report, European Patent Application No. 16862973.1 (dated Apr. 12, 2019).
Extended European Search Report, European Patent Application No. 16862973.1 (dated Jul. 19, 2019).
Communication in corresponding European Patent Application No. 16862973.1 (dated Nov. 6, 2020).
LoGrasso et al., "Rho Kinase (ROCK) Inhibitors and Their Application to Inflammatory Disorders," Current Topics in Medicinal Chemistry 9:704-723 (2009).

* cited by examiner

*Primary Examiner* — Umamaheswari Ramachandran
(74) *Attorney, Agent, or Firm* — Troutman Pepper Hamilton Sanders LLP (Rochester)

(57) ABSTRACT

The present invention relates to methods of treating a tumor or treating cancer in a subject having a p53 DNA contact mutation that involve administering, to the subject, a ROCK inhibitor. Also disclosed is a method of identifying a subject as a candidate for such treatment.

17 Claims, 7 Drawing Sheets
Specification includes a Sequence Listing.

XAV939 and Y-27632 cooperate to specifically target tumor cells harboring p53 DNA-contact mutations

XAV939 and Y-27632 treatment in different cell lines

METHODS OF TREATING TUMORS AND CANCER, AND IDENTIFYING CANDIDATE SUBJECTS FOR SUCH TREATMENT

This application is a national stage application under 35 U.S.C. § 371 of PCT Application No. PCT/US2016/060342, filed Nov. 3, 2016, which claims the priority benefit of U.S. Provisional Patent Application Ser. No. 62/335,642, filed May 12, 2016, and U.S. Provisional Patent Application Ser. No. 62/250,801, filed Nov. 4, 2015, which are hereby incorporated by reference in their entirety.

FIELD OF THE INVENTION

The present invention relates to methods of treating a tumor and cancer in a subject by administering a Rho-associated protein kinase ("ROCK") inhibitor to a subject with a tumor comprising a p53 DNA contact mutation, and identifying a subject as a candidate for such treatment.

BACKGROUND OF THE INVENTION

The evolutionarily conserved Hippo pathway plays a key role in tissue homeostasis and organ size control by regulating cell survival, proliferation and differentiation (Harvey et al., "The Hippo Pathway and Human Cancer," *Nature Reviews Cancer* 13:246-257 (2013)). This inhibitory pathway is comprised of a core kinase cascade, in which the mammalian sterile 20-like kinases MST1/2 and SAV1 form a complex that phosphorylates and activates the large tumor suppressor kinases LATS1/2, which in turn phosphorylate and inhibit the activities of the transcriptional co-activators YAP and TAZ (Oh et al., "Yorkie: The Final Destination of Hippo Signaling," *Trends in Cell Biology* 20:410-417 (2010); Pan, "The Hippo Signaling Pathway in Development and Cancer," *Developmental Cell* 19:491-505 (2010)). When liberated from Hippo pathway inhibition, YAP and TAZ accumulate in the nucleus where they drive gene expression by binding to TEAD, the DNA binding transcription factor regulated by the Hippo pathway as well as possibly other transcription factors, to promote cell proliferation and inhibit apoptosis (Harvey et al., "The Drosophila Mst Ortholog, Hippo, Restricts Growth and Cell Proliferation and Promotes Apoptosis," *Cell* 114:457-467 (2003); Udan et al., "Hippo Promotes Proliferation Arrest and Apoptosis in the Salvador/Warts Pathway," *Nature Cell Biology* 5:914-920 (2003); Pantalacci et al., "The Salvador Partner Hippo Promotes Apoptosis and Cell-cycle Exit in Drosophila," *Nature Cell Biology* 5:921-927 (2003); Wu et al., "Hippo Encodes a Ste-20 Family Protein Kinase that Restricts Cell Proliferation and Promotes Apoptosis in Conjunction with Salvador and Warts," *Cell* 114:445-456 (2003)). In fact, persistent nuclear localization of YAP and/or TAZ due to genetic alterations in the Hippo pathway has been linked mechanistically to oncogenesis (Moroishi et al., "The Emerging Roles of YAP and TAZ in Cancer," *Nature Reviews Cancer* 15:73-79 (2015); Steinhardt et al., "Expression of Yes-associated Protein in Common Solid Tumors," *Human Pathology* 39:1582-1589 (2008)).

The Hippo pathway can be modulated by a variety of stimuli, including G protein-coupled receptor (GPCR) signaling (Yu et al., "Regulation of the Hippo-YAP Pathway by G-protein-coupled Receptor Signaling," *Cell* 150:780-791 (2012)), actin cytoskeleton changes, cell-cell contact, and cell polarity (Dupont et al., "Role of YAP/TAZ in Mechanotransduction," *Nature* 474:179-183 (2011); Schroeder et al., "Regulation of the Hippo Pathway by Cell Architecture and Mechanical Signals," *Seminars in Cell & Developmental Biology* 23:803-811 (2012)). Various tumors have been shown to exhibit loss of function of LATS2 (Murakami et al., "LATS2 is a Tumor Suppressor Gene of Malignant Mesothelioma," *Cancer Research* 71:873-883 (2011)) or NF2 (Evans, "Neurofibromatosis 2 [Bilateral Acoustic Neurofibromatosis, Central Neurofibromatosis, NF2, Neurofibromatosis Type II]," *Genetics in Medicine: Official Journal of the American College of Medical Genetics* 11:599-610 (2009)), whose functions enforce Hippo negative regulation, or YAP amplification/overexpression (Xu et al., "Yes-associated Protein is an Independent Prognostic Marker in Hepatocellular Carcinoma," *Cancer* 115:4576-4585 (2009); Zhang et al., "The Hippo Pathway Transcriptional Co-activator, YAP, is an Ovarian Cancer Oncogene," *Oncogene* 30:2810-2822 (2011); Wang et al., "Overexpression of Yes-associated Protein Contributes to Progression and Poor Prognosis of Non-small-cell Lung Cancer," *Cancer Science* 101:1279-1285 (2010)). However, these alterations are relatively infrequent compared to aberrations afflicting oncogenes such as Ras or Raf or tumor suppressors such as p53 (Samatar et al., "Targeting RAS-ERK Signalling in Cancer: Promises and Challenges," *Nature Reviews Drug Discovery* 13:928-942 (2014); Muller et al., "p53 Mutations in Cancer," *Nature Cell Biology* 15:2-8 (2013); Selcukbiricik et al., "The Role of K-RAS and B-RAF Mutations as Biomarkers in Metastatic Colorectal Cancer," *Journal of B.U.ON.: Official Journal of the Balkan Union of Oncology* 18:116-123 (2013); Gast et al., "B-RAF Mutations in Tumors from Melanoma-breast Cancer Families," *International Journal of Cancer. Journal International du Cancer* 113:336-337 (2005)). Nonetheless, increasing interest in Hippo deregulation as an oncogenic driver has led to increased efforts to identify new activating mechanisms, most recently Gq11 activating mutations that up-regulate TEAD/YAP transcription in ocular melanomas (Yu et al., "Mutant Gq/11 Promote Uveal Melanoma Tumorigenesis by Activating YAP," *Cancer Cell* 25:822-830 (2014); Feng et al., "Hippo-independent Activation of YAP by the GNAQ Uveal Melanoma Oncogene Through a Trio-regulated Rho GTPase Signaling Circuitry," *Cancer Cell* 25:831-845 (2014)).

In efforts to identify new mechanisms of Hippo deregulation in human tumors, a large panel of human tumor lines was surveyed for activated TEAD/YAP transcription. By searching genomic data bases to identify alterations that might account for the high levels of TEAD activity detected in some, it was noted that a number contained p53 missense mutations, which result in a high level of expression of p53 protein unable to exert normal p53 tumor suppressor functions (Goh et al., "The Role of Mutant p53 in Human Cancer," *The Journal of Pathology* 223:116-126 (2011)). The dominant negative potential of mutant p53 when heterozygous with the wild-type allele has been proposed as an underlying basis for the high preponderance of p53 missense mutations in tumors (Bougeard et al., "Molecular Basis of the Li-Fraumeni Syndrome: an Update From the French LFS Families," *Journal of Medical Genetics* 45:535-538 (2008); Capponcelli et al., "Evaluation of the Molecular Mechanisms Involved in the Gain of Function of a Li-Fraumeni TP53 Mutation," *Human Mutation* 26:94-103 (2005); Hanel et al., "Two Hot Spot Mutant p53 Mouse Models Display Differential Gain of Function in Tumorigenesis," *Cell Death and Differentiation* 20:898-909 (2013); Lang et al., "Gain of Function of a p53 Hot Spot Mutation in a Mouse Model of Li-Fraumeni Syndrome," *Cell* 119:861-872 (2004); Olive et al., "Mutant p53 Gain of Function in Two Mouse Models of Li-Fraumeni Syndrome," *Cell* 119:847-860 (2004)). In fact, in Li-Fraumeni patients, germline missense mutations in TP53 consistently show an association with an earlier age of onset when compared with germline deletions. Moreover, mouse genetic models have revealed that some hotspot missense mutations generated as knock-in alleles produce an altered tumor spectrum and/or more metastatic tumors as compared to the loss of one or both wild type p53 alleles.

p53 missense mutants have also been reported to induce various biological effects (Muller et al., "Mutant p53 in Cancer: New Functions and Therapeutic Opportunities," *Cancer Cell* 25:304-317 (2014)). Such phenotypes are generally referred to as gain of function ("GOF"), although it is unclear whether all GOF mutant p53 share the same properties or how many specific GOF mechanisms may exist. Thus, increased understanding of mechanisms by which p53 missense mutations may acquire GOF could be important for prognosis and conceivably for therapy given that p53 missense mutations occur so frequently and in diverse tumor types (Petitjean et al., "TP53 Mutations in Human Cancers: Functional Selection and Impact on Cancer Prognosis and Outcomes," *Oncogene* 26:2157-2165 (2007)). Recently, one research group reported, based on expression array analysis, the upregulation of mevalonate pathway genes by the p53 mutant R273H (Freed-Pastor et al., "Mutant p53 Disrupts Mammary Tissue Architecture Via the Mevalonate Pathway," *Cell* 148:244-258 (2012)). Subsequent evidence indicated that the mutant p53 R280K was able to regulate YAP activity through modulation of the mevalonate pathway in MDA-MB-231 cells, which exhibit NF2 loss of function and constitutive activation of Yap (Sorrentino et al., "Metabolic Control of YAP and TAZ by the Mevalonate Pathway," *Nature Cell Biology* 16:357-366 (2014)). To illustrate the lack of clarity in mechanistic understanding of p53 mutant gain of function, these same p53 DNA contact mutants were more recently reported to cooperate with members of the SWI/SNF chromatin remodeling complex to regulate VEGFR2 in breast cancer cells (Pfister et al., "Mutant p53 Cooperates With the SWI/SNF Chromatin Remodeling Complex to Regulate VEGFR2 in Breast Cancer Cells," *Genes and Development* 29:1298-1315 (2015)).

The present invention is directed to overcoming deficiencies in the art.

SUMMARY OF THE INVENTION

One aspect of the present invention relates to a method of treating a tumor in a subject. This method involves administering to a subject having a tumor comprising a p53 DNA contact mutation a Rho-associated protein kinase (ROCK) inhibitor, where the ROCK inhibitor treats the tumor in the subject.

Another aspect of the present invention relates to a method of treating cancer in a subject. This method involves administering to a subject having a cancer comprising a p53 DNA contact mutation a ROCK inhibitor, where the ROCK inhibitor treats the subject for cancer.

A further aspect of the present invention relates to a method of identifying a subject as a candidate for treatment. This method involves obtaining a sample from a tumor in a subject and determining the presence of a p53 DNA contact mutation in the sample. The presence of a p53 DNA contact mutation in the sample indicates the tumor is susceptible to targeted treatment with a ROCK inhibitor and the subject is a candidate for treatment.

The present invention establishes that human tumors containing p53 missense mutations affecting amino acids that directly interact with DNA but not those which impair DNA binding through altered conformation of the DNA binding domain or X mutants which encode truncated, unstable p53 proteins show constitutive activation of TEAD/YAP-dependent transcription, which functions as an oncogenic driver. It is shown herein that genetic manipulations, which downregulate either p53 or TEAD/YAP transcription markedly and specifically inhibit proliferation of such tumor cells. Moreover it is demonstrated that inhibitors of ROCK, which act downstream of RhoA to mediate its signaling, phenocopy these effects. The exquisite specificity of these inhibitors for tumor cells bearing p53 DNA contact mutations strongly support the utility of ROCK inhibitors in therapeutically targeting these tumors.

BRIEF DESCRIPTION OF THE DRAWINGS

FIG. 1A shows a comparison of TEAD4 reporter activity in human tumor lines expressing different p53 mutations, and FIG. 1B shows mRNA expression of TEAD/YAP target genes (CTGF, CYR61, and ANKRD1) in human tumor lines expressing different p53 mutations. 293T and H2052 cells were used as a negative and positive control, respectively.

FIGS. 2A-C show analysis of TEAD4 reporter activity (FIG. 2A), CTGF mRNA expression (FIG. 2B), and proliferation in vitro in the indicated tumor lines upon either overexpression of DN TEAD4 or knock-down of p53 (FIG. 2C). FIG. 2D shows the effects of lentiviral transduction of DN TEAD4 or p53 knock-down on the tumor formation in vivo by MDA-MB-231 cells expressing a p53 DNA-contact mutation R280K. 1 million cells were inoculated orthotopically into the fat pads of the fifth mammary glands of 6-week-old immunocompromised female NOD/SCID mice. Time-course of tumor growth is shown on the left, tumor size at the time of sacrifice (4 months) is shown on the right.

FIGS. 3A-C show analysis of TEAD4 reporter activity (FIG. 3A), mRNA expression of TEAD/YAP target genes (CTGF, CYR61, ANKRD1) (FIG. 3B), and anchorage-independent growth in soft agar of immortalized MCF10A cells exogenously expressing by lentiviral transduction either YAP WT, p53 R248Q, p53 R273H, p53 R175H, or p53 G245S (FIG. 3C). FIGS. 3D-F show analysis of TEAD4 reporter activity (FIG. 3D), mRNA expression of TEAD/YAP target genes (CTGF, CYR61, ANKRD1) (FIG. 3E), and anchorage-independent growth in soft agar of immortalized MCF10A cells exogenously expressing by lentiviral transduction YAP WT, p53 R273H, or p53 R175H in the presence or in the absence of concurrent DN TEAD4 lentiviral transduction (FIG. 3F).

FIG. 4B shows the effects of treatment with Verteporfin, Simvastatin, or Y-27632 on proliferation of in vitro tumor lines with different p53 mutations. Of note, Y-27632 specifically inhibited proliferation of Hippo deregulated tumor cells with p53 DNA-contact mutations, whereas Verteporfin and Simvastatin exerted nonspecific effects by inhibiting proliferation also in tumor lines expressing p53 conformational mutations. FIG. 4C shows the effects treatment with the ROCK inhibitor Y-27632 on the colony formation in soft agar of a representative p53 DNA-contact mutant (R273H) or a different p53 mutant (R175H) or HRAS G12V in MCF10A cells. Note the lack of effects of Y-27632 treatment on the transformed phenotype induced by either p53 R175H or HRAS G12V.

FIG. 5A shows analysis of TEAD4 reporter activity in MDA-MB-231, a representative tumor line harboring a p53 DNA-contact mutation treated with either increasing doses of Y-27632, 1 µM Glycyl-H-1152, or 10 µM Fasudil. Note the lack of effect of 10 µM Fasudil on the TEAD reporter activity. FIG. 5B shows the effects of treatment with either increasing doses of Y-27632, 1 µM Glycyl-H-1152, or 10 µM Fasudil on proliferation of in vitro tumor lines with different p53 mutations. Note the specific inhibition of proliferation of tumor lines with p53 DNA-contact mutations at a concentration of 10-50 µM. Of note, Glycyl-H-1152 was able to specifically inhibit the proliferation of the same cells at concentrations 10-fold lower than Y-27632, whereas 10 µM Fasudil had no effect on proliferation of either MDA-MB-231 or SK-BR-3 cells, which are representative tumor lines harboring a p53 DNA-contact or conformational mutation, respectively.

FIG. 6 shows that suboptimal concentrations of the tankyrase inhibitor XAV939 and the ROCK inhibitor Y-27632 cooperate in specifically inhibiting the proliferation of tumor cells with p53 DNA contact mutations.

FIG. 7 shows that neither XAV939 nor Y-27632 inhibits proliferation of non-tumorigenic cells or p53 conformational mutant tumor cells without lesions in Hippo pathway core components. Further, ROCK inhibitors generally do not inhibit proliferation of tumor cells with lesions in Hippo pathway core components in contrast to XAV939, which inhibits proliferation of such tumor cells with p53 DNA contact mutants.

DETAILED DESCRIPTION OF THE INVENTION

Figure 1A:
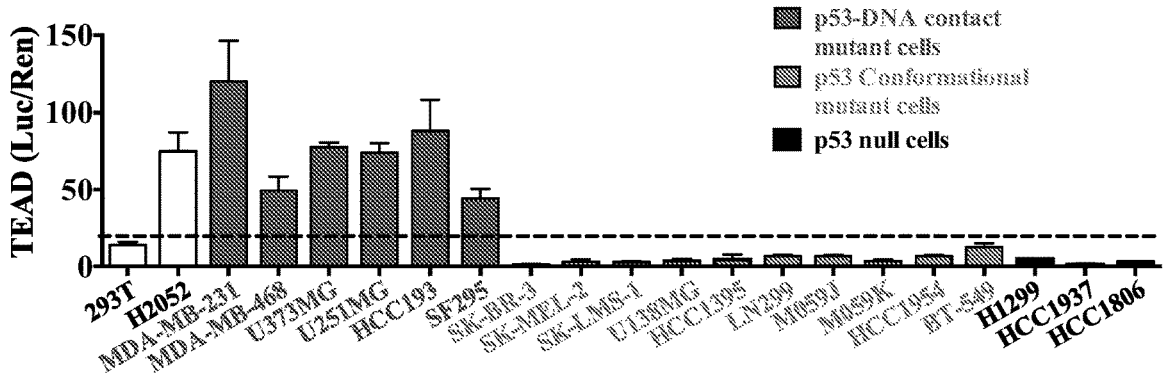
FIGS. 1A-B illustrate that p53 DNA-contact mutants identify a new class of Hippo deregulated tumors.

The present invention relates to methods of treating a tumor and cancer in a subject by administering a Rho-associated protein kinase (ROCK) inhibitor to a subject with a tumor comprising a p53 DNA contact mutation, and identifying a subject as a candidate for such treatment.

A first aspect of the present invention relates to a method of treating a tumor in a subject. This method involves administering to a subject having a tumor comprising a p53 DNA contact mutation a Rho-associated protein kinase (ROCK) inhibitor, where the ROCK inhibitor treats the tumor in the subject.

Another aspect of the present invention relates to a method of treating cancer in a subject. This method involves administering to a subject having a cancer comprising a p53 DNA contact mutation a ROCK inhibitor, where the ROCK inhibitor treats the subject for cancer.

In accordance with all aspects of the present invention, a "subject" encompasses any animal, but preferably a mammal, e.g., human, non-human primate, a dog, a cat, a horse, a cow, or a rodent. More preferably, the subject is a human.

As used herein, a "tumor" is any kind of new growth, benign or malignant. The term "cancer", as used herein, refers to a form of a tumor, namely malignant.

Cancers and tumors to be treated according to the methods of the present invention include, without limitation, carcinoma of the bladder, breast, colon, kidney, liver, lung, head and neck, gall-bladder, ovary, pancreas, stomach, cervix, thyroid, prostate, or skin; a hematopoietic tumor of lymphoid lineage (i.e., leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); a hematopoietic tumor of myeloid lineage (i.e., acute myelogenous leukemia, chronic myelogenous leukemia, multiple myelogenous leukemia, myelodysplastic syndrome, and promyelocytic leukemia); a tumor of mesenchymal origin (i.e., fibrosarcoma and rhabdomyosarcoma); a tumor of the central or peripheral nervous system (i.e., astrocytoma, neuroblastoma, glioma, and schwannomas); melanoma; seminoma; teratocarcinoma; osteosarcoma; thyroid follicular cancer; Kaposi's sarcoma; hepatoma; and mesothelioma.

As used herein, a "p53 DNA contact mutation" is a p53 mutation that affects amino acids that directly interact with DNA, but that does not impair DNA binding through altered conformation of the DNA binding domain or encode a truncated, unstable p53 protein. Mutations may include an insertion, a truncation, a deletion, a nonsense mutation, a frameshift mutation, a splice-site mutation, or a missense mutation.

In one embodiment of this and all other aspects of the present invention, the mutation comprises a non-synonymous single nucleotide base substitution. Such mutations can occur in the coding region of a p53 nucleic acid sequence, more particularly in any of the identified domains involved in contact with DNA. However, the present invention also encompasses mutations in p53 other than those specifically identified below. These mutations may be in coding or non-coding regions of p53.

P53 comprises the nucleotide sequence of SEQ ID NO: 1 as follows:

```
gatgggattg gggtttttccc ctcccatgtg ctcaagactg gcgctaaaag ttttgagctt ctcaaaagtc tagagccacc gtccagggag caggtagctg ctgggctccg gggacacttt gcgttcgggc tgggagcgtg cttccacga cggtgacacg cttccctgga ttggcagcca gactgccttc cgggtcactg ccatggagga gccgcagtca gatcctagcg tcgagccccc tctgagtcag gaaacatttt cagacctatg gaaactactt cctgaaaaca acgttctgtc ccccttgccg tcccaagcaa tggatgattt gatgctgtcc ccggacgata ttgaacaatg gttcactgaa gacccaggtc cagatgaagc tcccagaatg ccagaggctg ctccccccgt
```

```
ggcccctgca ccagcagctc ctacaccggc ggcccctgca
ccagccccct cctggcccct gtcatcttct
gtcccttccc agaaaaccta ccagggcagc tacggtttcc
gtctgggctt cttgcattct gggacagcca
agtctgtgac ttgcacgtac tcccctgccc tcaacaagat
gttttgccaa ctggccaaga cctgccctgt
gcagctgtgg gttgattcca cacccccgcc cggcacccgc
gtccgcgcca tggccatcta caagcagtca
cagcacatga cggaggttgt gaggcgctgc ccccaccatg
agcgctgctc agatagcgat ggtctggccc
ctcctcagca tcttatccga gtggaaggaa atttgcgtgt
ggagtatttg gatgacagaa acacttttcg
acatagtgtg gtggtgccct atgagccgtg tgaggttggc
tctgactgta ccaccatcca ctacaactac
atgtgtaaca gttcctgcat gggcggcatg aaccggaggc
ccatcctcac catcatcaca ctggaagact
ccagtggtaa tctactggga cggaacagct tgaggtgcg
tgtttgtgcc tgtcctggga gagaccggcg
cacagaggaa gagaatctcc gcaagaaagg ggagcctcac
cacgagctgc ccccagggag cactaagcga
gcactgccca acaaccacag ctcctctccc cagccaaaga
agaaaccact ggatggagaa tatttcaccc
ttcagatccg tgggcgtgag cgcttcgaga tgttccgaga
gctgaatgag gccttggaac tcaaggatgc
ccaggctggg aaggagccag ggggagcag gctcactcc
agccacctga agtccaaaaa gggtcagtct
acctcccgcc ataaaaaact catgttcaag acagaagggc
ctgactcaga ctgacattct ccacttcttg
ttccccactg acagcctccc acccccatct ctccctcccc
tgccatttg ggttttgggt ctttgaaccc
ttgcttgcaa taggtgtgcg tcagaagcac ccaggacttc
catttgcttt gtcccggggc tccactgaac
aagttggcct gcactggtgt tttgttgtgg ggaggaggat
ggggagtagg acataccagc ttagatttta
aggtttttac tgtgagggat gtttgggaga tgtaagaaat
gttcttgcag ttaagggtta gtttacaatc
agccacattc taggtagggg cccacttcac cgtactaacc
agggaagctg tccctcactg ttgaatttc
tctaacttca aggcccatat ctgtgaaatg ctggcatttg
cacctacctc acagagtgca ttgtgaggg
```

```
taatgaaata atgtacatct ggccttgaaa ccaccttta
ttacatgggg tctagaactt gacccccttg
agggtgcttg ttccctctcc ctgttggtcg gtgggttggt
agtttctaca gttgggcagc tggtaggta
gagggagttg tcaagtctct gctggcccag ccaaaccctg
tctgacaacc tcttggtgaa ccttagtacc
taaaagaaa tctcaccca tcccacaccc tggaggattt
catctcttgt atatgatgat ctggatccac
caagacttgt tttatgctca gggtcaattt ctttttttctt
tttttttttt tttttctttt ttctttgaga
ctgggtctcg ctttgttgcc caggctggag tggagtggcg
tgatcttggc ttactgcagc ctttgcctcc
ccggctcgag cagtcctgcc tcagcctccg gagtagctgg
gaccacaggt tcatgccacc atggccagcc
aacttttgca tgttttgtag agatggggtc tcacagtgtt
gcccaggctg gtctcaaact cctgggctca
ggcgatccac ctgtctcagc ctcccagagt gctgggatta
caattgtgag ccaccacgtc cagctggaag
ggtcaacatc ttttacattc tgcaagcaca tctgcatttt
caccccaccc ttcccctcct tctcccttt
tatatcccat ttttatatcg atctcttatt ttacaataaa
actttgctgc cacctgtgtg tctgagggt g
```

The amino acid sequence of p53 (SEQ ID NO:2) is as follows:

```
MEEPQSDPSV EPPLSQETFS DLWKLLPENN VLSPLPSQAM
DDLMLSPDDI EQWFTEDPGP DEAPRMPEAA
PPVAPAPAAP TPAAPAPAPS WPLSSSVPSQ KTYQGSYGFR
LGFLHSGTAK SVTCTYSPAL NKMFCQLAKT
CPVQLWVDST PPPGTRVRAM AIYKQSQHMT EVVRRCPHHE
RCSDSDGLAP PQHLIRVEGN LRVEYLDDRN
TFRHSVVVPY EPPEVGSDCT TIHYNYMCNS SCMGGMNRRP
ILTIITLEDS SGNLLGRNSF EVRVCACPGR
DRRTEEENLR KKGEPHHELP PGSTKRALPN NTSSSPQPKK
KPLDGEYFTL QIRGRERFEM FRELNEALEL
KDAQAGKEPG GSRAHSSHLK SKKGQSTSRH KKLMFKTEGP
DSD
```

The p53 DNA contact mutation can encode an amino acid substitution at one or more amino acid residues corresponding to amino acid positions 120, 241, 248, 273, 276, 277, 280, and/or 283 of SEQ ID NO: 2. Exemplary mutations in the nucleotide sequence encoding these amino acid substitutions include, without limitation, those that result in a lysine (K) to glutamic acid (E) substitution at an amino acid position corresponding to position 120 (K120E) of SEQ ID NO: 2; a lysine (K) to asparagine (N) substitution at an amino acid position corresponding to position 120 (K120N) of SEQ ID NO: 2; a serine (S) to phenylalanine (F) substitution at an amino acid position corresponding to position 241 (S241F) of SEQ ID NO: 2; a serine (S) to cysteine (C) substitution at an amino acid position corresponding to position 241 (S241C) of SEQ ID NO: 2; a serine (S) to tyrosine (Y) substitution at an amino acid position corresponding to position 241 (S241Y) of SEQ ID NO: 2; a serine (S) to proline (P) substitution at an amino acid position corresponding to position 241 (S241P) of SEQ ID NO: 2; an arginine (R) to glutamine (Q) substitution at an amino acid position corresponding to position 248 (R248Q) of SEQ ID NO: 2; an arginine (R) to tryptophan (W) substitution at an amino acid position corresponding to position 248 (R248W) of SEQ ID NO: 2; an arginine (R) to leucine (L) substitution at an amino acid position corresponding to position 248 (R248L) of SEQ ID NO: 2; an arginine (R) to proline (P) substitution at an amino acid position corresponding to position 248 (R248P) of SEQ ID NO: 2; an arginine (R) to glycine (G) substitution at an amino acid position corresponding to position 248 (R248G) of SEQ ID NO: 2; an arginine (R) to cysteine (C) substitution at an amino acid position corresponding to position 273 (R273C) of SEQ ID NO: 2; an arginine (R) to histidine (H) substitution at an amino acid position corresponding to position 273 (R273H) of SEQ ID NO: 2; an arginine (R) to leucine (L) substitution at an amino acid position corresponding to position 273 (R273L) of SEQ ID NO: 2; an arginine (R) to proline (P) substitution at an amino acid position corresponding to position 273 (R273P) of SEQ ID NO: 2; an arginine (R) to serine (S) substitution at an amino acid position corresponding to position 273 (R273S) of SEQ ID NO: 2; an arginine (R) to tyrosine (Y) substitution at an amino acid position corresponding to position 273 (R273Y) of SEQ ID NO: 2; an alanine (A) to proline (P) substitution at an amino acid position corresponding to position 276 (A276P) of SEQ ID NO: 2; an alanine (A) to aspartic acid (D) substitution at an amino acid position corresponding to position 276 (A276D) of SEQ ID NO: 2; an alanine (A) to glycine (G) substitution at an amino acid position corresponding to position 276 (A276G) of SEQ ID NO: 2; an alanine (A) to valine (V) substitution at an amino acid position corresponding to position 276 (A276V) of SEQ ID NO: 2; a cysteine (C) to phenylalanine (F) substitution at an amino acid position corresponding to position 277 (C277F) of SEQ ID NO: 2; an arginine (R) to threonine (T) substitution at an amino acid position corresponding to position 280 (R280T) of SEQ ID NO: 2; an arginine (R) to lysine (K) substitution at an amino acid position corresponding to position 280 (R280K) of SEQ ID NO: 2; an arginine (R) to glycine (G) substitution at an amino acid position corresponding to position 280 (R280G) of SEQ ID NO: 2; an arginine (R) to isoleucine (I) substitution at an amino acid position corresponding to position 280 (R280I) of SEQ ID NO: 2; an arginine (R) to serine (S) substitution at an amino acid position corresponding to position 280 (R280S) of SEQ ID NO: 2; and an arginine (R) proline (P) substitution at an amino acid position corresponding to position 283 (R283P) of SEQ ID NO. 2.

In some embodiments of the present invention, the p53 DNA contact mutation is selected from the group consisting of R280K, R273H, and R248Q.

Rho family of small GTPases is a class of small G-proteins which play a critical role in signaling pathways and control organelle development, cytoskeletal dynamics, cell growth and division, cell movement, and other cellular functions. Rho must be located at the interior of the plasma membrane and is translocated by attachment of the C-20 geranyl group to a C-terminal. The GTP bound form of Rho is "switched on" and interacts with a variety of downstream effectors, including the Rho-associated protein kinases (ROCKs) (Boureax et al., "Evolution of the Rho Family of Ras-like GTPases in Eukaryotes," *Mol. Biol. Evol.* 24(1): 203-16 (2007); Bustel et al., "GTP-binding Proteins of the Rho/Rac Family: Regulation, Effectors and Functions In Vivo," *BioEssays* 29(4):356-370 (2007), which are hereby incorporated by reference in their entirety).

Two ROCK isoforms have been identified in the art and include ROCK1 and ROCK2. Both ROCK1 and ROCK2 are serine/threonine protein kinases that are activated by the GTP-bound form of RhoA. Activation of ROCKS results in phosphorylation of substrates involved in cell signaling. ROCK signaling pathways are implicated in cell morphology, motility, smooth muscle contraction, formation of stress fiber, focal adhesion, cell transformation, and cytokinesis. Based on the broad involvement of the ROCK signaling pathway in a variety of cellular functions, ROCK inhibitors have been under investigation for treating many diseases, including diabetes, neurodegenerative diseases such as Parkinson's disease, cardiovascular diseases such as pulmonary hypertension, inflammation, and glaucoma. In addition, recent findings have shown that ROCK inhibitors can be used to establish 3D-organoid cultures derived from patients with tumors and to grow stem cells in culture (Mueller et al., "Rho Kinase, a Promising Drug Target for Neurological Disorders," *Nat. Rev. Drug Discovery* 4:387-398 (2005); Liao et al., "Rho Kinase (ROCK) Inhibitors," *J. Cardiovasc. Pharmacol.* 50(1):17-24 (2007); Ohgushi and Sasai, "Lonely Death Dance of Human Pluripotent Stem Cells: ROCKing Between Metastable Cell States," *Trends Cell Bio.* 21(5):274-82 (2011), which are hereby incorporated by reference in their entirety).

ROCK1 comprises the nucleotide sequence (NCBI Reference Sequence: NM_005406) of SEQ ID NO:3 as follows:

```
gctggttccc cttccgagcg tccgcgcccc gcatgcgcag tctgcccgg cggtctccgt    60 ttgtttgaac aggaaggcgg acatattagt ccctctcagc cccctcgcc ccaccccca   120 ggcattcgcc gccgcgactc gcccttccc cggctgggac cgcagcccct cccagaagct   180
cccccatcag cagccgccgg gacccaacta tcgtcttcct cttcgcccgc tctccagcct   240
ttcctctgct aagtctccat cgggcatcga cctcgccctg ccccaccgga caccgtagca   300 gcagcccag cagcgacggg acaaaatggg agagtgaggc tgtcctgcgt ggaccagctc   360
gtggccgaga ctgatcggtg cgtcgggccg ggccgagtag agccggggac gcggggctag   420
accgtctaca gcgcctctga gcggagcggg cccggcccgt ggcccgagcg gcggccgcag   480
```

-continued

```
ctggcacagc tcctcacccg cccttttgctt tcgccttttcc tcttctccct cccttgttgc    540
ccggagggag tctccaccct gcttctcttt ctctacccgc tcctgcccat ctcgggacgg    600
ggacccctcc atggcgacgg cggccggggc ccgctagact gaagcacctc gccggagcga    660
cgaggctggt ggcgacggcg ctgtcggctg tcgtgagggg ctgccgggtg ggatgcgact    720
ttgggcgtcc gagcggctgt gggtcgctgt tgccccccggc ccggggtctg gagagcggag    780
gtcccctcag tgaggggaag acgggggaac cgggcgcacc tggtgacccct gaggttccgg    840 ctcctccgcc ccgcggctgc gaacccaccg cggaggaagt tggttgaaat tgctttccgc    900
tgctggtgct ggtaagaggg cattgtcaca gcagcagcaa catgtcgact ggggacagtt    960
ttgagactcg atttgaaaaa atggacaacc tgctgcggga tcccaaatcg gaagtgaatt   1020
cggattgttt gctggatgga ttggatgctt tggtatatga tttggatttt cctgccttaa   1080
gaaaaaacaa aaatattgac aacttttttaa gcagatataa agacacaata aataaaatca   1140 gagattttacg aatgaaagct gaagattatg aagtagtgaa ggtgattggt agaggtgcat   1200
ttggagaagt tcaattggta aggcataaat ccaccaggaa ggtatatgct atgaagcttc   1260
tcagcaaatt tgaaatgata aagagatctg attctgcttt tttctgggaa gaaagggaca   1320
tcatggcttt tgccaacagt ccttgggttg ttcagctttt ttatgcattc caagatgatc   1380
gttatctcta catggtgatg gaatacatgc ctggtggaga tcttgtaaac ttaatgagca   1440
actatgatgt gcctgaaaaa tgggcacgat tctatactgc agaagtagtt cttgcattgg   1500
atgcaatcca ttccatgggt tttattcaca gagatgtgaa gcctgataac atgctgctgg   1560
ataaatctgg acatttgaag ttagcagatt ttggtacttg tatgaagatg aataaggaag   1620
gcatggtacg atgtgataca gcggttggaa cacctgatta tatttcccct gaagtattaa   1680
aatcccaagg tggtgatggt tattatggaa gagaatgtga ctggtggtcg gttggggtat   1740
ttttatacga aatgcttgta ggtgatacac ctttttatgc agattctttg gttggaactt   1800
acagtaaaat tatgaaccat aaaaattcac ttacctttttcc tgatgataat gacatatcaa   1860
aagaagcaaa aaaccttatt tgtgccttcc ttactgacag ggaagtgagg ttagggcgaa   1920
atggtgtaga agaaatcaaa cgacatctct tcttcaaaaa tgaccagtgg gcttgggaaa   1980
cgctccgaga cactgtagca ccagttgtac ccgatttaag tagtgacatt gatactagta   2040
attttgatga cttggaagaa gataaaggag aggaagaaac attccctatt cctaaagctt   2100
tcgttggcaa tcaactacct tttgtaggat ttacatatta tagcaatcgt agatacttat   2160
cttcagcaaa tcctaatgat aacagaacta gctccaatgc agataaaagc ttgcaggaaa   2220
gtttgcaaaa aacaatctat aagctggaag aacagctgca taatgaaatg cagttaaaag   2280
atgaaatgga gcagaagtgc agaacctcaa acataaaact agacaagata atgaaagaat   2340
tggatgaaga gggaaatcaa agaagaaatc tagaatctac agtgtctcag attgagaagg   2400
agaaaatgtt gctacagcat agaattaatg agtaccaaag aaaagctgaa caggaaaatg   2460
agaagagaag aaatgtagaa aatgaagttt ctacattaaa ggatcagttg gaagacttaa   2520
agaaagtcag tcagaattca cagcttgcta atgagaagct gtcccagtta caaaagcagc   2580
tagaagaagc caatgactta cttaggacag aatcggacac agctgtaaga ttgaggaaga   2640
gtcacacaga gatgagcaag tcaattagtc agttagagtc cctgaacaga gagttgcaag   2700
agagaaatcg aatttttagag aattctaagt cacaaacaga caaagattat taccagctgc   2760
aagctatatt agaagctgaa cgaagagaca gaggtcatga ttctgagatg attggagacc   2820
ttcaagctcg aattacatct ttacaagagg aggtgaagca tctcaaacat aatctcgaaa   2880
```

-continued

```
aagtggaagg agaaagaaaa gaggctcaag acatgcttaa tcactcagaa aaggaaaaga    2940
ataatttaga gatagattta aactacaaac ttaaatcatt acaacaacgg ttagaacaag    3000
aggtaaatga acacaaagta accaaagctc gtttaactga caaacatcaa tctattgaag    3060
aggcaaagtc tgtggcaatg tgtgagatgg aaaaaaagct gaaagaagaa agagaagctc    3120
gagagaaggc tgaaaatcgg gttgttcaga ttgagaaaca gtgttccatg ctagacgttg    3180
atctgaagca atctcagcag aaactagaac atttgactgg aaataaagaa aggatggagg    3240
atgaagttaa gaatctaacc ctgcaactgg agcaggaatc aaataagcgg ctgttgttac    3300
aaaatgaatt gaagactcaa gcatttgagg cagacaattt aaaaggttta gaaaagcaga    3360
tgaaacagga aataaatact ttattggaag caaagagatt attagaattt gagttagctc    3420
agcttacgaa acagtataga ggaaatgaag gacagatgcg ggagctacaa gatcagcttg    3480
aagctgagca atatttctcg acactttata aacccaggt aaaggaactt aaagaagaaa    3540
ttgaagaaaa aaacagagaa aatttaaaga aaatacagga actacaaaat gaaaagaaa     3600 ctcttgctac tcagttggat ctagcagaaa caaaagctga gtctgagcag ttggcgcgag    3660
gccttctgga agaacagtat tttgaattga cgcaagaaag caagaaagct gcttcaagaa    3720
atagacaaga gattacagat aaagatcaca ctgttagtcg gcttgaagaa gcaaacagca    3780
tgctaaccaa agatattgaa atattaagaa gagagaatga agagctaaca gagaaaatga    3840
agaaggcaga ggaagaatat aaactggaga aggaggagga gatcagtaat cttaaggctg    3900
cctttgaaaa gaatatcaac actgaacgaa cccttaaaac acaggctgtt aacaaattgg    3960
cagaaataat gaatcgaaaa gattttaaaa ttgatagaaa gaaagctaat acacaagatt    4020
tgagaaagaa agaaaaggaa aatcgaaagc tgcaactgga actcaaccaa gaaagagaga    4080
aattcaacca gatggtagtg aaacatcaga aggaactgaa tgacatgcaa gcgcaattgg    4140
tagaagaatg tgcacatagg aatgagcttc agatgcagtt ggccagcaaa gagagtgata    4200
ttgagcaatt gcgtgctaaa cttttggacc tctcggattc tacaagtgtt gctagttttc    4260
ctagtgctga tgaaactgat ggtaacctcc cagagtcaag aattgaaggt tggctttcag    4320
taccaaatag aggaaatatc aaacgatatg gctggaagaa acagtatgtt gtggtaagca    4380
gcaaaaaaat tttgttctat aatgacgaac aagataagga gcaatccaat ccatctatgg    4440
tattggacat agataaactg tttcacgtta gacctgtaac ccaaggagat gtgtatagag    4500
ctgaaactga agaaattcct aaaatattcc agatactata tgcaaatgaa ggtgaatgta    4560
gaaaagatgt agagatggaa ccagtacaac aagctgaaaa aactaatttc caaaatcaca    4620
aaggccatga gtttattcct acactctacc actttcctgc caattgtgat gcctgtgcca    4680
aacctctctg gcatgttttt aagccacccc ctgccctaga gtgtcgaaga tgccatgtta    4740
agtgccacag agatcactta gataagaaag aggacttaat ttgtccatgt aaagtaagtt    4800
atgatgtaac atcagcaaga gatatgctgc tgttagcatg ttctcaggat gaacaaaaaa    4860
aatgggtaac tcatttagta aagaaaatcc ctaagaatcc accatctggt tttgttcgtg    4920
cttcccctcg aacgctttct acaagatcca ctgcaaatca gtctttccgg aaagtggtca    4980 aaatacatc tggaaaaact agttaaccat gtgactgagt gccctgtgga atcgtgtggg    5040
atgctacctg ataaaccagg cttctttaac catgcagagc agacaggctg tttctttgac    5100
acaaatatca caggcttcag ggttaagatt gctgttttc tgtccttgct ttggcacaac    5160
acactgaggg ttttttttat tgcgggtttg cctacaggta gattagatta attattacta    5220
tgtaatgcaa gtacagttgg gggaaagctt aggtagatat attttttta aaaggtgctg    5280 ccttttttgga tttataagaa aatgcctgtc agtcgtgata gaacagagtt ttcctcatat    5340
```

-continued

```
gagtaagagg aagggacttt cactttcaag tggaacagcc atcactatca agatcagctc   5400
atggaaggag taaagaaaat atctcaaaat gagacaaact gaagttttgt ttttttttta   5460
atgacttaag ttttgtgct cttgcaagac tatacaaaac tattttaaga aagcagtgat   5520
atcacttgaa cttcagtgcc ctcactgtag aatttaaaag ccttactgtt gattgcccat   5580
gttggacttg atggagaaat taaatatctt tcattatgct ttacaaaata ctgtatatgt   5640
ttcagcaagt ttggggaatg ggagaggaca aaaaaaagtt acatttaatc tatgcattt    5700 tgccaagcca tattgagtta ttttactact agagacatta ggaaactaac tgtacaaaag   5760
aaccaagttt aaaagcattt tgtggggtac atcatttcta taattgtata atgtatttct   5820
ttgtggtttt aaatgataaa gacattaagt taacaaacat ataagaaatg tatgcactgt   5880
ttgaaatgta aattattctt agaacacttt caatggggt tgcattgtcc ttttagtgcc    5940
ttaatttgag ataattattt tactgccatg agtaagtata gaaatttcaa aaaatgtatt   6000
ttcaaaaaat tatgtgtgtc agtgagtttt tcattgataa ttggtttaat ttaaaatatt   6060
tagaggtttg ttggactttc ataaattgag tacaatcttt gcatcaaact acctgctaca   6120
ataatgactt tataaaactg caaaaaatgt agaaggttgc accaacataa aaggaaata    6180 tggcaataca tccatgatgt tttccagtta acataggaat taccagataa atactgttaa   6240
actcttgtcc agtaacaaga gttgattcat atggacagta tgatttattg tttatttttt   6300
taaccaaata cctcctcagt aatttataat ggctttgcag taatgtgtat cagataagaa   6360
gcactggaaa accgatcgtc tctaggatga tatgcatgtt tcaagtggta ttgaaagccg   6420
cactgatgga tatgtaataa taaacatatc tgttattaat atactaatga ctctgtgctc   6480
atttaatgag aaataaaagt aatttatgga tgggtatctt taattttttac tgcaatgtgt   6540 tttctcatgg ctgaaatgaa tggaaaacat acttcaaatt agtctctgat tgtatataaa   6600
tgtttgtgaa attccatggt tagattaaag tgtattttta aaagataaaa               6650
```

ROCK2 comprises the nucleotide sequence NCBI Reference Sequence: NM_004850) of SEQ ID NO:4 as follows:

```
caaggcggcc ggcggcgacc atggcagcgg gccggcggcg gccgtagtgg cccaggcctg     60
ggcttcagcc tcccggggcc ccagagggcg gggcggtccg ggccgcggcg gtggcggcgc    120
cacttccctg ctcccgcccg aggactcctg cgggcactcg ctgaggacca gcggaccggc    180
ggcgcgaatc tgactgaggg gcggggacgc cgtctgttcc ccgccgctcc cggcagggcc    240
gggccgggct gggccgggct gggccgggcg ggccctggg agcagccccc aggcggggga     300
ccgccttgga gacccgaagc cggagctaga ggcaggcggt gggcccgggt ggagtcccgg    360
ccggagctgg tggttcgggg gcggtgctag gccccgaggc tgcgggacct gagcgcgagg    420
agcctgagtg cgggtccagc ggtggcggca tgagccggcc cccgccgacg gggaaaatgc    480
ccggcgcccc cgagaccgcg ccggggacg ggcaggcgc gagccgccag aggaagctgg      540
aggcgctgat ccgagaccct cgctccccca tcaacgtgga gagcttgctg gatggcttaa    600
attccttggt ccttgattta gatttttcctg ctttgaggaa aaacaagaac atagataatt    660 tcttaaaatag atatgagaaa attgtgaaaa aaatcagagg tctacagatg aaggcagaag    720
actatgatgt tgtaaaagtt attggaagag gtgcttttgg tgaagtgcag ttggttcgtc    780
acaaggcatc gcagaaggtt tatgctatga agcttcttag taagtttgaa atgataaaaa    840
gatcagattc tgccttttt tgggaagaaa gagatattat ggcctttgcc aatagcccct    900
```

-continued

```
gggtggttca gctttttat gcctttcaag atgataggta tctgtacatg gtaatggagt    960
acatgcctgg tggagacctt gtaaaccttta tgagtaatta tgatgtgcct gaaaaatggg  1020
ccaaatttta cactgctgaa gttgttcttg ctctggatgc aatacactcc atgggtttaa  1080
tacacagaga tgtgaagcct gacaacatgc tcttggataa acatgacat ctaaaattag   1140 cagattttgg cacgtgtatg aagatggatg aaacaggcat ggtacattgt gatacagcag  1200
ttggaacacc ggattatata tcacctgagg ttctgaaatc acaagggggt gatggtttct  1260
atgggcgaga atgtgattgg tggtctgtag gtgttttcct ttatgagatg ctagtggggg  1320
atactccatt ttatgcggat tcacttgtag gaacatatag caaaattatg gatcataaga  1380
attcactgtg tttccctgaa gatgcagaaa tttccaaaca tgcaaagaat ctcatctgtg  1440
ctttcttaac agatagggag gtacgacttg ggagaaatgg ggtggaagaa atcagacagc  1500
atcctttctt taagaatgat cagtggcatt gggataacat aagagaaacg gcagctcctg  1560
tagtacctga actcagcagt gacatagaca gcagcaattt cgatgacatt gaagatgaca  1620
aaggagatgt agaaaccttc ccaattccta agcttttgt tggaaatcag ctgcctttca   1680
tcggatttac ctactataga gaaaatttat tattaagtga ctctccatct tgtagagaaa  1740
ctgattccat acaatcaagg aaaaatgaag aaagtcaaga gattcagaaa aaactgtata  1800
cattagaaga acatcttagc aatgagatgc aagccaaaga ggaactggaa cagaagtgca  1860
aatctgttaa tactcgccta gaaaaaacag caaaggagct agaagaggag attaccttac  1920
ggaaaagtgt ggaatcagca ttaagacagt tagaaagaga aaaggcgctt cttcagcaca  1980
aaaatgcaga atatcagagg aaagctgatc atgaagcaga caaaaaacga aatttggaaa  2040
atgatgttaa cagcttaaaa gatcaacttg aagatttgaa aaaagaaat caaaactctc    2100 aaatatccac tgagaaagtg aatcaactcc agagacaact ggatgaaacc aatgctttac  2160
tgcgaacaga gtctgatact gcagcccggt taaggaaaac ccaggcagaa agttcaaaac  2220
agattcagca gctggaatct aacaatagag atctacaaga taaaaactgc ctgctggaga  2280
ctgccaagtt aaaacttgaa aaggaattta tcaatcttca gtcagctcta gaatctgaaa  2340
ggagggatcg aacccatgga tcagagataa ttaatgattt acaaggtaga atatgtggcc  2400
tagaagaaga tttaaagaac ggcaaaatct tactagcgaa agtagaactg gagaagagac  2460
aacttcagga gagatttact gatttggaaa aggaaaaaag caacatggaa atagatatga  2520
cataccaact aaaagttata cagcagagcc tagaacaaga agaagctgaa cataaggcca  2580
caaaggcacg actagcagat aaaaataaga tctatgagtc catcgaagaa gccaaatcag  2640
aagccatgaa agaaatggag aagaagctct tggaggaaag aactttaaaa cagaaagtgg  2700
agaacctatt gctagaagct gagaaaagat gttctctatt agactgtgac ctcaaacagt  2760
cacagcagaa aataaatgag ctccttaaac agaaagatgt gctaaatgag gatgttagaa  2820
acctgacatt aaaaatagag caagaaactc agaagcgctg ccttacacaa aatgacctga  2880
agatgcaaac acaacaggtt aacacactaa aaatgtcaga aaagcagtta agcaagaaa   2940 ataaccatct catggaaatg aaaatgaact tggaaaaaca aaatgctgaa cttcgaaaag  3000
aacgtcagga tgcagatggg caaatgaaag agctccagga tcagctcgaa gcagaacagt  3060
atttctcaac ccttttataaa acacaagtta gggagcttaa agaagaatgt gaagaaaaga  3120
ccaaacttgg taaagaattg cagcagaaga acaggaatt acaggatgaa cgggactctt   3180
tggctgccca actggagatc accttgacca aagcagattc tgagcaactg gctcgttcaa  3240
ttgctgaaga acaatattct gatttggaaa agagaaagat catgaagag ctggagatca   3300 aagagatgat ggctagacac aaacaggaac ttacggaaaa agatgctaca attgcttctc  3360
```

-continued

```
ttgaggaaac taataggaca ctaactagtg atgttgccaa tcttgcaaat gagaagaag    3420 aattaaataa caaattgaaa gatgttcaag agcaactgtc aagattgaaa gatgaagaaa    3480
taagcgcagc agctattaaa gcacagtttg agaagcagct attaacagaa agaacactca    3540
aaactcaagc tgtgaataag ttggctgaga tcatgaatcg aaaagaacct gtcaagcgtg    3600
gtaatgacac agatgtgcgg agaaaagaga aggagaatag aaagctacat atggagctta    3660
aatctgaacg tgagaaattg acccagcaga tgatcaagta tcagaaagaa ctgaatgaaa    3720
tgcaggcaca atagctgaa gagagccaga ttcgaattga actgcagatg acattggaca    3780
gtaaagacag tgacattgag cagctgcggt cacaactcca agccttgcat attggtctgg    3840
atagttccag tataggcagt ggaccagggg atgctgaggc agatgatggg tttccagaat    3900
caagattaga aggatggctt tcattgcctg tacgaaacaa cactaagaaa tttggatggg    3960
ttaaaaagta tgtgattgta agcagtaaga agattctttt ctatgacagt gaacaagata    4020
aagaacaatc caatccttac atggttttag atatagacaa gttatttcat gtccgaccag    4080
ttacacagac agatgtgtat agagcagatg ctaaagaaat tccaaggata ttccagattc    4140
tgtatgccaa tgaaggagaa agtaagaagg aacaagaatt tccagtggag ccagttggag    4200
aaaaatctaa ttatatttgc cacaagggac atgagtttat tcctactctt tatcatttcc    4260
caaccaactg tgaggcttgt atgaagcccc tgtggcacat gtttaagcct cctcctgctt    4320
tggagtgccg ccgttgccat attaagtgtc ataaagatca tatggacaaa aaggaggaga    4380
ttatagcacc ttgcaaagta tattatgata tttcaacggc aaagaatctg ttattactag    4440
caaattctac agaagagcag cagaagtggg ttagtcggtt ggtgaaaaag atacctaaaa    4500
agcccccagc tccagaccct tttgcccgat catctcctag aacttcaatg aagatacagc    4560
aaaaccagtc tattagacgg ccaagtcgac agcttgcccc aaacaaacct agctaactgc    4620
cttctatgaa agcagtcatt attcaaggtg atcgtattct tccagtgaaa acaagactga    4680
aatatgatgg cccaaaattt attaaaaagc tatattttcc tgagagactg atacatacac    4740
tcatacatat atgtgttccc cttttccctg taatataaat tacaaatctg ggctcctttg    4800
aagcaacagg ttgaaccaac aatgattggt tgatagacta aggatatatg caactcttcc    4860
agacttttcc ataaagctct ctcggcagtc gctcacacta caatgcacac aaggattgag    4920
aagagttaaa ggctaaagaa aacatctttt ctagcttcaa cagagaggtt tcaccagcac    4980
atttaccaga agaatctggg aatggattcc actacagtga tattgactgc atctttaaga    5040
agtgaccatt atactgtgta tatatatata aacacacaca catatatata tatatatata    5100
gtactctaat actgcaagaa ggttttttaa acttcccact ttatttttta tacacattaa    5160
tcagatatca ttacttgctg cagttgcaac tatgcacttg tataaagcca taatgttgga    5220
gtttatatca ctcattcctg tgtacctgat ggaagttgca tgttcatgtt taagcagtta    5280
ctgtaacaag aagtttaaag ttaattatat cagtttccta atgcttcatg ataggcaact    5340
ttacccattt tgaatgcctt aatttaattt ttttcaaagt ctcagccctg tctgtattaa    5400
aaaacaaaaa aagcgtttac cagctcttag gatgtaaact agctttgtgg aagataaatc    5460
gtgcactatt tttacacata aatagttata tcaatgtcag cctattttga ttaacaaatg    5520 ttttttaaagt attattggtt atagaaacaa taatggatgg tgttggaact aatatatcct    5580
tgatgtctgt ctattattca ttcaactctt tttacagacc tcagtattag tctgtgacta    5640
caaaatattt tatttgcttt aaatttgctg gctaccctag atgtgttttt attcctggta    5700
aagacatttg tgattacatt ttcacactta agattcaaaa ttttttccaa atataaagaa    5760
```

-continued

```
aactaagaca gactgtagat gcattttaaa tatttaaata tgatcctcag acatgcagct  5820
gtgtgtggca gtattttagt accgggttaa gaaaactggc aactgggaag aagtggcctc  5880
aaaggcactt aatttgattt ttatttttta aatgctgtca aagttacagt ttacgcagga  5940
cattcttgcc gtattctcat gatcccagat aagtgtgtgt tttatactgc aacaatatgc  6000
agcaatggta agcgtaaagt ttttttttttg tttttgtttt tttttatatt atgaagtctt  6060
ttaacagtct ctctttatat aaatacacag agtttggtat gatatttaaa tacatcatct  6120
ggccaggcat ggtggcttac gcctgtaatc ctagcacttt gggaggccaa gacgggcgga  6180
tcacctgagg tgaggagttc aagaccagcc tgcccaacat agtgaaactc cgtctctacc  6240
aatatacaaa aattagccgg gcatgatggt ggtggcctgt aatcccagct acttgggagg  6300
ctgagacagg agaatcgctt gaacccagga gacggtggtt gcagtgagcg aagatcgagc  6360
cactgcactc cagcctgggc agctgaacaa gactccgtct c                      6401
```

In another embodiment of the methods of the present invention, a tankyrase inhibitor is also administered. Thus, according to various embodiments of the methods of the present invention, both a ROCK inhibitor and a tankyrase inhibitor are administered to a subject to treat a tumor in a subject or to treat cancer in a subject.

In one embodiment, both the ROCK inhibitor and the tankyrase inhibitor are combined in a single pharmaceutical formulation. In an alternative embodiment, the ROCK inhibitor and the tankyrase inhibitor are separately formulated into two different pharmaceutical formulations as described herein and administered in two separate dosages. Thus, according to various embodiments, the ROCK inhibitor and the tankyrase inhibitor may be administered together, separately, or as co-treatments.

According to one embodiment, the ROCK inhibitor and the tankyrase inhibitor are each administered at a dose sufficient in their combination to treat a tumor in a subject or to treat a subject for cancer, but in a dosage not sufficient (e.g., too low of an amount) for either the ROCK inhibitor or the tankyrase inhibitor alone to treat a tumor in a subject or to treat a subject for cancer. Thus, according this embodiment, the ROCK inhibitor and the tankyrase inhibitor are administered at dosages such that they cause a synergistic treatment effect.

There are two human tankyrases—tankyrase 1 and tankyrase 2. Human tankyrase 1 has a published nucleotide sequence as set forth in Accession No. NM_003747 (SEQ ID NO:5), as follows:

```
cgaagatggc ggcgtcgcgt cgctctcagc atcatcacca ccatcatcaa caacagctcc    60
agcccgcccc aggggcttca gcgccgccgc cgccacctcc tcccccactc agccctggcc   120
tggccccggg gaccacccca gcctctccca cggccagcgg cctggccccc ttcgcctccc   180
cgcggcacgg cctagcgctg ccggaggggg atggcagtcg ggatccgccc gacaggcccc   240
gatccccgga cccggttgac ggtaccagct gttgcagtac caccagcaca atctgtaccg   300
tcgccgccgc tcccgtggtc ccagcggttt ctacttcatc tgccgctggg gtcgctccca   360
acccagccgg cagtggcagt aacaattcac cgtcgtcctc ttcttccccg acttcttcct   420
catcttcctc tccatcctcc cctggatcga gcttggcgga gagccccgag gcggccggag   480
ttagcagcac agcaccactg gggcctgggg cagcaggacc tgggacaggg gtcccagcag   540 tgagcgggc cctacgggaa ctgctggagg cctgtcgcaa tggggacgtg tcccgggtaa   600
agaggctggt ggacgcggca aacgtaaatg caaaggacat ggccggccgg aagtcttctc   660
ccctgcactt cgctgcaggt tttggaagga aggatgttgt agaacactta ctacagatgg   720
gtgctaatgt ccacgctcgt gatgatggag gtctcatccc gcttcataat gcctgttctt   780
ttggccatgc tgaggttgtg agtctgttat tgtgccaagg agctgatcca aatgccaggg   840
ataactggaa ctatacacct ctgcatgaag ctgctattaa agggaagatc gatgtgtgca   900
ttgtgctgct gcagcacgga gctgacccaa acattcggaa cactgatggg aaatcagccc   960
tggacctggc agatcctttca gcaaaagctg tccttacagg tgaatacaag aaagacgaac  1020
tcctagaagc tgctaggagt ggtaatgaag aaaaactaat ggctttactg actcctctaa  1080
atgtgaattg ccatgcaagt gatgggcgaa agtcgactcc tttacatcta gcagcgggct  1140
```

-continued

```
acaacagagt tcgaatagtt cagcttcttc ttcagcatgg tgctgatgtt catgcaaaag   1200
acaaaggtgg acttgtgcct cttcataatg catgttcata tggacattat gaagtcacag   1260
aactgctact aaagcatgga gcttgtgtta atgccatgga tctctggcag tttactccac   1320
tgcacgaggc tgcttccaag aaccgtgtag aagtctgctc tttgttactt agccatggcg   1380
ctgatcctac attagtcaac tgccatggca aaagtgctgt ggatatggct ccaactccgg   1440
agcttaggga gagattgact tatgaattta aaggtcattc tttactacaa gcagccagag   1500
aagcagactt agctaaagtt aaaaaaacac tcgctctgga aatcattaat ttcaaacaac   1560
cgcagtctca tgaaacagca ctgcactgtg ctgtggcctc tctgcatccc aaacgtaaac   1620
aagtgacaga attgttactt agaaaggag caaatgttaa tgaaaaaaat aaagatttca    1680
tgactcccct gcatgttgca gccgaaagag cccataatga tgtcatggaa gttctgcata   1740
agcatggcgc caagatgaat gcactggaca cccttggtca gactgctttg catagagccg   1800
ccctagcagg ccacctgcag acctgccgcc tcctgctgag ttacggctct gaccctcca    1860 tcatctcctt acaaggcttc acagcagcac agatgggcaa tgaagcagtg cagcagattc   1920
tgagtgagag tacacctata cgtacttctg atgttgatta tcgactctta gaggcatcta   1980
aagctggaga cttggaaact gtgaagcaac tttgcagctc tcaaaatgtg aattgtagag   2040
acttagaggg ccggcattcc acgcccttac acttcgcagc aggctacaac cgcgtgtctg   2100
ttgtagagta cctgctacac cacggtgccg atgtccatgc caaagacaag ggtggcttgg   2160
tgccccttca taatgcctgt tcatatggac actatgaggt ggctgagctt ttagtaaggc   2220
atggggcttc tgtcaatgtg gcggacttat ggaaatttac ccctctccat gaagcagcag   2280
ctaaaggaaa gtatgaaatc tgcaagctcc ttttaaaaca tggagcagat ccaactaaaa   2340
agaacagaga tggaaataca cctttggatt tggtaaagga aggagacaca gatattcagg   2400
acttactgag agggggatgct gctttgttgg atgctgccaa gaagggctgc ctggcaagag   2460
tgcagaagct ctgtaccccca gagaatatca actgcagaga cacccagggc agaaattcaa   2520
cccctctgca cctggcagca ggctataata acctggaagt agctgaatat cttctagagc   2580
atggagctga tgttaatgcc caggacaagg gtggtttaat tcctcttcat aatgcggcat   2640
cttatgggca tgttgacata gcggctttat tgataaaata caacacgtgt gtaaatgcaa   2700
cagataagtg ggcgtttact ccccttccatg aagcagccca gaaaggaagg acgcagctgt   2760
gcgccctcct cctagcgcat ggtgcagacc ccaccatgaa gaaccaggaa ggccagacgc   2820
ctctggatct ggcaacagct gacgatatca gagctttgct gatagatgcc atgccccag    2880 aggccttacc tacctgtttt aaacctcagg ctactgtagt gagtgcctct ctgatctcac   2940
cagcatccac cccctcctgc ctctcggctg ccagcagcat agacaacctc actggccctt   3000
tagcagagtt ggccgtagga ggagcctcca atgcagggga tggcgccgcg ggaacagaaa   3060
ggaaggaagg agaagttgct ggtcttgaca tgaatatcag ccaatttcta aaaagccttg   3120
gccttgaaca ccttcgggat atctttgaaa cagaacagat tacactagat gtgttggctg   3180
atatgggtca tgaagagttg aaagaaatag gcatcaatgc atatgggcac cgccacaaat   3240
taatcaaagg agtagaaaga ctcttaggtg acaacaagg caccaatcct tatttgactt    3300
ttcactgtgt taatcaggga acgattttgc tggatcttgc tccagaagat aaagaatatc   3360
agtcagtgga agaagagatg caaagtacta ttcgagaaca cagagatggt ggtaatgctg   3420
gcggcatctt caacagatac aatgtcattc gaattcaaaa agttgtcaac aagaagttga   3480
gggagcggtt ctgccaccga cagaaggaag tgtctgagga gaatcacaac catcacaatg   3540
```

-continued

```
agcgcatgtt gtttcatggt tctccttttca ttaatgccat tattcataaa gggtttgatg   3600
agcgacatgc atacatagga ggaatgtttg gggccgggat ttattttgct gaaaactcct   3660
caaaaagcaa ccaatatgtt tatggaattg gaggaggaac aggctgccct acacacaagg   3720
acaggtcatg ctatatatgt cacagacaaa tgctcttctg tagagtgacc cttgggaaat   3780
cctttctgca gtttagcacc atgaaaatgg cccacgcgcc tccagggcac cactcagtca   3840
ttggtagacc gagcgtcaat gggctggcat atgctgaata tgtcatctac agaggagaac   3900
aggcataccc agagtatctt atcacttacc agatcatgaa gccagaagcc ccttcccaga   3960
ccgcaacagc cgcagagcag aagacctagt gaatgcctgc tggtgaaggc cagatcagat   4020
ttcaacctgg gactggatta cagaggattg tttctaataa caacatcaat attctagaag   4080
tccctgacag cctagaaata agctgtttgt cttctataaa gcattgctat agtgatgaat   4140
agtatgagta actgatacat actcaactgc tactgttccc tttgaggaaa tgtttacagg   4200
ggcggccttt taacatatct caggctcatt ttcattgcaa ttatccattt ctaaaacaag   4260
attgcttcga tctagacttg gaaatggaaa ataagaaaac caatgctttt tcaaatgttc   4320
acaattcaca cactacattt gttttgttat gcatgacgtg tctataacaa atatacacat   4380
acgacaggca acaagcttgt ttttgatttg ccagacatgc atcattggct attgtttgtt   4440
tgttttttgt ttttttgtgt ttttgggtt actttgaaaa tgagccagag ccttcttgag    4500
gatattttgc acaaagtcac gctgacaaaa tcattagcag tgcaacccaa gcttctggct   4560
gagcaagatt cagtttccac ttttttaaaat tttttttattt tgctctgtag ctgcacttct   4620
cgttatcata aattgagatg aaaggaaaa acatcaagt tttagtacct ttttatgaat    4680
tggcctatct tacaagagaa gggcacaaac accaacctga cttaggaacg cctaaattca   4740
gagaagtcaa agccggtgaa ggccacttgc tctttccaac acaagcctgc cacagaggtc   4800
ttcgggacag tactggagat gcaggttgac acgggcttga gttccaaggt gaaaaaactg   4860
gggaggctgt gaaggaagag ctgcattaag gagggtgagg agcgtgtggt tctgtatcat   4920
ggcagcccca atggatccag gggatgcctc caaaaaatac atgcttccct tcccttaatc   4980
tgtactgttg ggattgttac ccctccaaat tagctgcctt atttcaaaag tcagtgaaat   5040
tactgcactt gatgagggtc acaaaaatac cacttgattg tttctttagt tgagaatgct   5100
gggattcaga ctcgaatagt ggatagatac acacaaatgc aaggactttt ttgtttactc   5160
cagatttggg gtttattttg agtggcatgc ttcaaatagt tcataaagat ccttgcatta   5220
aatttctgaa ccatttcttc aaacttctta gtgtgtttag acaaggagaa caaaaattga   5280
aaccaaagcc ctttctgtta ttttttcaat gaaggtgaga aagaaatacc atacaatttt   5340
ctttgtgaaa ttactgtttta ttttcatcaa catttaccaa gtgccattga catttataaa   5400
aaaaaatgat cctttatagt tcttacactt gccctttca ccttaactga atatgaattg   5460
agtgcactaa cttatttact tgatatactg tgcatctact ctgctttgaa gcgaaagaaa   5520
tataaacacg aggaggaata ggaaagacag tgtgacacaa acttgccatt gcaattcaaa   5580
gccctgaaaa cgatgggttt aatgcaaggt gattaagctg tgacctcctt taatctcctg   5640
aagcaaaata aaatggttac atgcaaaact tctagaaata gactcttaaa atatatacat   5700
tttgctttga ttttggcttc aacccagtgc tggaactagg catccagact agtttgaatg   5760
tttgtagctg aatttttatg ggtcctcaaa attaaatcga gaattagcct cagttgttgc   5820
ttcttttgaa gttcagtga cccaagctgg gtgtttgtgt cttggctact tgtttaatag   5880
cactagaatt ccaggtgaag ctttgagagt tgatattcat taagagggct ttttttcccc   5940
ttctttcctt ctctttttgct gtaacaaagg gttgaagaaa ttgccatctg tgtagttttc   6000
```

```
agtagctgtc aagtgtgtct tacttacctt cccccagacg tagtttaaaa tggtaaacac   6060
agctgtgatt tttagttaag taaaagagtt aatatgatat agatatggaa agctttatgg   6120
cttcattaaa aagataaacc actacctaac tgtggttgta tgttgtttcc atcatactaa   6180
ctagatgaat ggatgcgcca gttttcatct tggtccttac acttgagaag ttaaactgtg   6240
gttcagtatt taaactgcca gtgttatacg tctcatgctc tgtgtgccag gtgaaggtac   6300
tgtgtaagga agacatttgc ggtgcttctt gtcctataat gattcaagta tatagtagtt   6360
cttgaaagag tgtgcatata ttactcatct gcttaagaga gtgggttaat ggatatatca   6420
gaggagccaa atacattttt ttcagaactt gaaaaccaaa ggtcatcatg agtgcactca   6480
aaagttagga caagtttatt acatttggga ttttcatctg tagccgtatg aagaacccct   6540
tccaatataa aagcatggca ttaaattagg ctgaagtctt ttatttttg tatatgtact    6600 atatagaaat actagcaagt taggatcatc caatatggcc taccccgaaa tggcccctct   6660
gtttccctaa ccacatggaa gaagaatct gaacgtctcc accggctcta cccgagttcc    6720
aaaactaaag ggcttctcca gacctgatgg ttccagttta cctgctgttg gcctgctgga   6780
tacttgactc aggcataaat taagtgccct ggtcccgaac tttctccctg tatttgacct   6840
ccttccctct ttcctaaatt actagtctgg aattaaaatt agctccagca atgaccttg    6900 actccattca ttttctcctc atcttgggtc ttaaaaaagg agaccagata cctcctagct   6960
tttgtatcac aaccaggaat gggtattagg cctcatgcgc tttgctcaga acactgccgc   7020
tttgttaaca aatgacagca tggaacccag agttttgatt cgatgcaaaa taacagcagt   7080
gcaaccagga ttcttgtttt ccttttcctt cttggagttt ggaatttcta gcttttcaag   7140
cagcataagt agaatcaaca ttaggatgtt ttcatgaaat agcatcctta tacttctttg   7200
agcttgatgt tagtggctag actgatttcc ctttgctctc aaaatacaaa gtgcattgaa   7260
gtatacagag aaatgcctga atatggcaag caaataatgt agattaacat tctattattg   7320
tatccgtttt acaaaaaata aaattttgat atatgccgga gaacggcatt agaatgcaat   7380
aagttgtcta ggttttctg tttcagtgtc tctcccaatg gcacgaaggg ttattgggca   7440
ttgtccccac ccccgccttt ttaacatgtg cactatctgg attcctgtaa atggccttgc   7500
aaacagaagt ggtgtgtatt ttcaagcacc tttccccat tgtatccgaa tccctcttgt    7560
gtgatatctg tgacaaatag ccttcttctt gtgttttctg ttggactaat tgtctcacgt   7620
aaagctatag accttactaa tttggcaggt attcaaaact gccattaaga taggatttca   7680
tgtcagatac gtatttaaag agtaaagtca aatttgttta atgtcagatc agtgacagaa   7740
gtgaaaagaa agtaattgtg aaagtgatgt ttgagctatt gtacacatct agcatatgga   7800
aagcaaatgc actcgaaaac tactattcta gaacatgagg cttcttcagc aacttgtgca   7860
ctctgccatt aataaattaa attttccc tctagaaagc cttaactatg gcggaaactt     7920
tttaaccttt tatattttaa taaataaaac attgtagtcc catttcttag tgtttgaaag   7980
gtgtgtcagt gagtcggcca tgtctccatg tgtttcagac ctgttcatct tatttatga    8040 tggtatattt cataagtaat attcccttac atgcaatgga gctgattaaa attaatccat   8100
ttcaatttct ccatattgga acttcctcag ctaccagatt tctggtttgg agaagtgctg   8160
gaaagatttc aaagcctatt cagttgtgta tgtggggata cgacagcaac tgtgatacct   8220
```

```
tgtagaatat gagtgatatg caagctgtgt tttttaattg ttttaaaatg taaattatgg   8280
ttatgctaaa gtgaaaacct agaggaagct aatgatttta tatactttgc acgaccaaat   8340
atggtcgtag tatgacgagt tttatacatt gccagagagt tctgcctcct ctgaaataac   8400
attcgcactg tagattgcat ttcggctttt cctcctttca cattcttttt tgctttacac   8460
ttcacgtctt cgcacctgcc ctacctccca tcctttcaaa gaggtttctt tcacgttcca   8520
gaattcagat tgttctgtga tttcttttac atcagtctac ccatttctgc aggcagccct   8580
gaaagccctt gtgttgattc agagtgtttg cagagaaatg cagttgaacc ctggtagtgg   8640
ggtgtccctc acacacccgc gcaccccctcc caaagttcag gatgaaaggc tagaaaaccc   8700
attcaaagtt aggaaagaac acagatcttt gaggccgata gcctagacct agaagatgac   8760
cttgagtatg taaacattgt ctccgtgaca caaaacactg aaactcttca tgtgcatata   8820
acacctgctt ctgctcccat tgtttcaagc tcatcttatc tttgtagtag taatgttgt    8880 ctttgatacc tacaaactaa aaaggtactt ttatcaaggt ttctcaaaac atttacaaaa   8940
ccagctttga gaaaatgtta tgttgcctgg caacagcact cggagtagta attgtgtttt   9000
ctcattgtga tgttggtctg tgtgagcaac cagtgtagtg actctttggt tcattattcg   9060
tgttgttttt attttagtc tctgtgtgac ccaacagtgg caggggttac aacccctct    9120 cctttctttt ttgtatttat ctatttgtag gattgtcaga tcaagtacaa gatgcccagt   9180
taagtttgaa tttcagagaa acaatttcac gttaagaatg tttcatgcaa tatttggcat   9240
atatttacag taaaagcatt cattatttgt ctgaaattca aatttaactg agcatgctgg   9300 ttttctcat tgtttggttt ttctaaatct ggcaatccta cagctgtggt catgggaaat    9360
cacctacagc atgttaaagt cctctagtca tcatctcgtc acctgaaatg gaagtccttt   9420
ttccctcacc ctccacttct ttccaaagga gggcatcaag gaacttaacc tgcctgcctg   9480
gtgggtttct atttaagaca tctttgtgat tatatttaac ctgcaattgt gctttggctt   9540
aatgtctagc tcactgtact tgtaaatgat taatattcaa taaaaccatt tttaaagta    9599
```

The human tankyrase 1 protein encoded by this nucleotide sequence is as follows (SEQ ID NO:6):

```
MAASRRSQHH HHHHQQQLQP APGASAPPPP PPPPLSPGLA

PGTTPASPTA SGLAPFASPR HGLALPEGDG

SRDPPDRPRS PDPVDGTSCC STTSTICTVA AAPVVPAVST

SSAAGVAPNP AGSGSNNSPS SSSSPTSSSS

SSPSSPGSSL AESPEAAGVS STAPLGPGAA GPGTGVPAVS

GALRELLEAC RNGDVSRVKR LVDAANVNAK

DMAGRKSSPL HFAAGFGRKD VVEHLLQMGA NVHARDDGGL

IPLHNACSFG HAEVVSLLLC QGADPNARDN

WNYTPLHEAA IKGKIDVCIV LLQHGADPNI RNTDGKSALD

LADPSAKAVL TGEYKKDELL EAARSGNEEK

LMALLTPLNV NCHASDGRKS TPLHLAAGYN RVRIVQLLLQ

HGADVHAKDK GGLVPLHNAC SYGHYEVTEL

LLKHGACVNA MDLWQFTPLH EAASKNRVEV CSLLLSHGAD

PTLVNCHGKS AVDMAPTPEL RERLTYEFKG

HSLLQAAREA DLAKVKKTLA LEIINFKQPQ SHETALHCAV

ASLHPKRKQV TELLLRKGAN VNEKNKDFMT

PLHVAAERAH NDVMEVLHKH GAKMNALDTL GQTALHRAAL

AGHLQTCRLL LSYGSDPSII SLQGFTAAQM

GNEAVQQILS ESTPIRTSDV DYRLLEASKA GDLETVKQLC

SSQNVNCRDL EGRHSTPLHF AAGYNRVSVV

EYLLHHGADV HAKDKGGLVP LHNACSYGHY EVAELLVRHG

ASVNVADLWK FTPLHEAAAK GKYEICKLLL

KHGADPTKKN RDGNTPLDLV KEGDTDIQDL LRGDAALLDA

AKKGCLARVQ KLCTPENINC RDTQGRNSTP

LHLAAGYNNL EVAEYLLEHG ADVNAQDKGG LIPLHNAASY

GHVDIAALLI KYNTCVNATD KWAFTPLHEA

AQKGRTQLCA LLLAHGADPT MKNQEGQTPL DLATADDIRA

LLIDAMPPEA LPTCFKPQAT VVSASLISPA

STPSCLSAAS SIDNLTGPLA ELAVGGASNA GDGAAGTERK

EGEVAGLDMN ISQFLKSLGL EHLRDIFETE
```

```
QITLDVLADM GHEELKEIGI NAYGHRHKLI KGVERLLGGQ

QGTNPYLTFH CVNQGTILLD LAPEDKEYQS

VEEEMQSTIR EHRDGGNAGG IFNRYNVIRI QKVVNKKLRE

RFCHRQKEVS EENHNHHNER MLFHGSPFIN
```

```
AIIHKGFDER HAYIGGMFGA GIYFAENSSK SNQYVYGIGG

GTGCPTHKDR SCYICHRQML FCRVTLGKSF

LQFSTMKMAH APPGHHSVIG RPSVNGLAYA EYVIYRGEQA

YPEYLITYQI MKPEAPSQTA TAAEQKT
```

Human tankyrase 2 has a published nucleotide sequence as set forth in Accession No. NM_025235 (SEQ ID NO:7), as follows:

```
ggctggacgg agctggcagg aggggccttg ccagcttccg ccgccgcgtc gtttcaggac    61
ccggacggcg gattcgcgct gcctccgccg ccgcggggca gccgggggc agggagccca   121 gcgaggggcg cgcgtgggcg cggccatggg actgcgccgg atccggtgac agcagggagc   181
caagcggccc gggccctgag cgcgtcttct ccggggggcc tcgccctcct gctcgcgggg   241
ccggggctcc tgctccggtt gctggcgctg ttgctggctg tggcggcggc caggatcatg   301
tcgggtcgcc gctgcgccgg cggggagcg gcctgcgcga gcgccgcggc cgaggccgtg   361
gagccggccg cccgagagct gttcgaggcg tgccgcaacg gggacgtgga acgagtcaag   421
aggctggtga cgcctgagaa ggtgaacagc cgcgacacgg cgggcaggaa atccaccccg   481
ctgcacttcg ccgcaggttt tgggcggaaa gacgtagttg aatatttgct tcagaatggt   541
gcaaatgtcc aagcacgtga tgatggggc cttattcctc ttcataatgc atgctctttt   601
ggtcatgctg aagtagtcaa tctccttttg cgacatggtg cagaccccaa tgctcgagat   661
aattggaatt atactcctct ccatgaagct gcaattaaag gaaagattga tgtttgcatt   721
gtgctgttac agcatggagc tgagccaacc atccgaaata cagatggaag gacagcattg   781
gatttagcag atccatctgc caaagcagtg cttactggtg aatataagaa gatgaactc   841 ttagaaagtg ccaggagtgg caatgaagaa aaaatgatgg ctctactcac accattaaat   901
gtcaactgcc acgcaagtga tggcagaaag tcaactccat acatttggc agcaggatat   961 aacagagtaa agattgtaca gctgttactg caacatggag ctgatgtcca tgctaaagat  1021
aaaggtgatc tggtaccatt acacaatgcc tgttcttatg gtcattatga agtaactgaa  1081
cttttggtca agcatggtgc ctgtgtaaat gcaatggact tgtggcaatt cactcctctt  1141
catgaggcag cttctaagaa cagggttgaa gtatgttctc ttctcttaag ttatggtgca  1201
gacccaacac tgctcaattg tcacaataaa agtgctatag acttggctcc cacaccacag  1261
ttaaaagaaa gattagcata tgaatttaaa ggccactcgt tgctgcaagc tgcacgagaa  1321
gctgatgtta ctcgaatcaa aaaacatctc tctctggaaa tggtgaattt caagcatcct  1381
caaacacatg aaacagcatt gcattgtgct gctgcatctc catatcccaa aagaaagcaa  1441
atatgtgaac tgttgctaag aaaaggagca aacatcaatg aaaagactaa agaattcttg  1501
actcctctgc acgtggcatc tgagaaagct cataatgatg ttgttgaagt agtggtgaaa  1561
catgaagcaa aggttaatgc tctggataat cttggtcaga cttctctaca cagagctgca  1621
tattgtggtc atctacaaac ctgccgccta ctcctgagct atgggtgtga tcctaacatt  1681
atatcccttc agggctttac tgctttacag atgggaaatg aaaatgtaca gcaactcctc  1741
caagagggta tctcattagg taattcagag gcagacagac aattgctgga agctgcaaag  1801
gctggagatg tcgaaactgt aaaaaaactg tgtactgttc agagtgtcaa ctgcagagac  1861 attgaaggc gtcagtctac accacttcat tttgcagctg gtataacag agtgtccgtg  1921 gtggaatatc tgctacagca tggagctgat gtgcatgcta agataaagg aggccttgta  1981 cctttgcaca atgcatgttc ttatggacat tatgaagttg cagaacttct tgttaaacat  2041
```

-continued

```
ggagcagtag ttaatgtagc tgatttatgg aaatttacac ctttacatga agcagcagca   2101
aaaggaaaat atgaaatttg caaacttctg ctccagcatg gtgcagaccc tacaaaaaaa   2161
aacagggatg gaaatactcc tttggatctt gttaaagatg gagatacaga tattcaagat   2221
ctgcttaggg gagatgcagc tttgctagat gctgccaaga agggttgttt agccagagtg   2281
aagaagttgt cttctcctga taatgtaaat tgccgcgata cccaaggcag acattcaaca   2341
cctttacatt tagcagctgg ttataataat ttagaagttg cagagtattt gttacaacac   2401
ggagctgatg tgaatgccca agacaaagga ggacttattc ctttacataa tgcagcatct   2461
tacgggcatg tagatgtagc agctctacta ataaagtata atgcatgtgt caatgccacg   2521
gacaaatggg ctttcacacc tttgcacgaa gcagcccaaa agggacgaac acagctttgt   2581
gctttgttgc tagcccatgg agctgacccg actcttaaaa atcaggaagg acaaacacct   2641
ttagatttag tttcagcgga tgatgtcagc gctcttctga cagcagccat gccccccatct   2701 gctctgccct cttgttacaa gcctcaagtg ctcaatggtg tgagaagccc aggagccact   2761
gcagatgctc tctcttcagg tccatctagc ccatcaagcc tttctgcagc cagcagtctt   2821
gacaacttat ctgggagttt ttcagaactg tcttcagtag ttagttcaag tggaacagag   2881
ggtgcttcca gtttggagaa aaaggaggtt ccaggagtag atttttagcat aactcaattc   2941 gtaaggaatc ttggacttga gcacctaatg gatatatttg agagagaaca gatcactttg   3001
gatgtattag ttgagatggg gcacaaggag ctgaaggaga ttggaatcaa tgcttatgga   3061
cataggcaca aactaattaa aggagtcgag agacttatct ccggacaaca aggtcttaac   3121
ccatatttaa ctttgaacac ctctggtagt ggaacaattc ttatagatct gtctcctgat   3181
gataaagagt ttcagtctgt ggaggaagag atgcaaagta cagttcgaga gcacagagat   3241
ggaggtcatg caggtggaat cttcaacaga tacaatattc tcaagattca gaaggtttgt   3301
aacaagaaac tatgggaaag atacactcac cggagaaaag aagtttctga agaaaaccac   3361
aaccatgcca atgaacgaat gctatttcat gggtctcctt ttgtgaatgc aattatccac   3421
aaaggctttg atgaaaggca tgcgtacata ggtggtatgt ttggagctgg catttatttt   3481
gctgaaaact cttccaaaag caatcaatat gtatatggaa ttggaggagg tactgggtgt   3541
ccagttcaca agacagatc ttgttacatt tgccacaggc agctgctctt ttgccgggta   3601
accttgggaa agtctttcct gcagttcagt gcaatgaaaa tggcacattc tcctccaggt   3661
catcactcag tcactggtag gcccagtgta aatggcctag cattagctga atatgttatt   3721
tacagaggag aacaggctta tcctgagtat ttaattactt accagattat gaggcctgaa   3781
ggtatggtcg atggataaat agttatttta agaaactaat tccactgaac ctaaaatcat   3841
caaagcagca gtggcctcta cgttttactc ctttgctgaa aaaaaatcat cttgcccaca   3901
ggcctgtggc aaaaggataa aaatgtgaac gaagtttaac attctgactt gataaagctt   3961
taataatgta cagtgttttc taaatatttc ctgttttttc agcactttaa cagatgccat   4021
tccaggttaa actgggttgt ctgtactaaa ttataaacag agttaacttg aacctttat   4081 atgttatgca ttgattctaa caaactgtaa tgccctcaac agaactaatt ttactaatac   4141
aatactgtgt tctttaaaac acagcattta cactgaatac aatttcattt gtaaaactgt   4201
aaataagagc ttttgtacta gcccagtatt tatttacatt gctttgtaat ataaatctgt   4261
tttagaactg cagcggttta caaaattttt tcatatgtat tgttcatcta tacttcatct   4321
tacatcgtca tgattgagtg atctttacat ttgattccag aggctatgtt cagttgttag   4381
ttgggaaaga ttgagttatc agatttaatt tgccgatggg agcctttatc tgtcattaga   4441
aatctttctc attttaagaac ttatgaatat gctgaagatt taatttgtga tacctttgta   4501
```

-continued

```
tgtatgagac acattccaaa gagctctaac tatgataggt cctgattact aaagaagctt  4561
ctttactggc ctcaatttct agctttcatg ttggaaaatt ttctgcagtc cttctgtgaa  4621
aattagagca aagtgctcct gttttttaga gaaactaaat cttgctgttg aacaattatt  4681
gtgttctttt catggaacat aagtaggatg ttacatttcc agggtgggaa gggtaatcct  4741
aaatcatttc ccaatctatt ctaattacct taaatctaaa ggggaaaaaa aaaatcacaa  4801
acaggactgg gtagtttttt atcctaagta tattttttcc tgttctttttt acttggtttt  4861 attgctgtat ttatagccaa tctatacatc atgggtaaac ttaacccaga actataaaat  4921
gtagttgtct cagtcccctc caggcctcct gaatgggcaa gtgcagtgaa acaggtgctt  4981
cttgctcctg ggtttttctct ccatgatgtt atgcccaatt ggaaatatgc tgtcagtttg  5041
tgcaccatat ggtgaccacg cctgtgctca gtttggcagc tatagaagga aatgctgtcc  5101
cataaaatgc cattcctatt ttctaatata aaactctttt ccaggaagca tgcttaagca  5161
tcttgttaca gagacataca tccattatgg cttggcaatc tcttttattt gttgactcta  5221
gctcccttca aagtcgagga aagatcttta ctcacttaat gaggacattc cccatcactg  5281
tctgtaccag ttcacccttta ttttacgttt tattcagtct gtaaattaac tggccctttg  5341
cagtaacttg tacataaagt gctagaaaat catgttcctt gtcctgagta agagttaatc  5401
agagtaaatg catttctgga gttgtttctg tgatgtaaat tatgatcatt atttaagaag  5461
tcaaatcctg atcttgaagt gcttttttata cagctctcta ataattacaa atatccgaaa  5521
gtcatttctt ggaacacaag tggagtatgc caaattttat atgaattttt cagattatct  5581
aagcttccag gttttataat tagaagataa tgagagaatt aatggggttt atatttacat  5641
tatctctcaa ctatgtagcc catattactc accctatgag tgaatctgga attgcttttc  5701
atgtgaaatc attgtggtct atgagtttac aatactgcaa actgtgttat tttatctaat  5761
ccattgctta atgagtgtgt ttttccatga atgaatatac cgtggttcat atgttagcat  5821
ggcagcattt tcagatagct ttttgtttgt tgggaagttg gggttttggg gggaggggga  5881
gtattagtac gttgcatgaa atagcttact ttataatgat ggaattgctt tttcttttgt  5941
cttgtgattt ttttttttga agtgaaattt aactttttgt gcaagtagta ctattatacc  6001
catcttcagt gtcttacttg tactgtatca cattccatac cctcatttaa ttcttaataa  6061
aactgttcac ttgttttttct gggtagcatg gtaattactg gaatagtata aatgtgttga  6121
atggtctttg agaaaatgaa ttaagattac aataaaccac aattgcagga aaacaatgta  6181
gttctgagtc taatagtgat aaagaatgca gtttgaagtt tgaaatattg aatattgtag  6241
ctgtacttgc tcattaaaat gaaagtagct gtga
```

The human tankyrase 2 protein encoded by this nucleotide sequence is as follows (SEQ ID NO:8):

```
MSGRRCAGGG AACASAAAEA VEPAARELFE ACRNGDVERV

KRLVTPEKVN SRDTAGRKST PLHFAAGFGR

KDVVEYLLQN GANVQARDDG GLIPLHNACS FGHAEVVNLL

LRHGADPNAR DNWNYTPLHE AAIKGKIDVC

IVLLQHGAEP TIRNTDGRTA LDLADPSAKA VLTGEYKKDE

LLESARSGNE EKMMALLTPL NVNCHASDGR

KSTPLHLAAG YNRVKIVQLL LQHGADVHAK DKGDLVPLHN

ACSYGHYEVT ELLVKHGACV NAMDLWQFTP

LHEAASKNRV EVCSLLLSYG ADPTLLNCHN KSAIDLAPTP

QLKERLAYEF KGHSLLQAAR EADVTRIKKH

LSLEMVNFKH PQTHETALHC AAASPYPKRK QICELLLRKG

ANINEKTKEF LTPLHVASEK AHNDVVEVVV

KHEAKVNALD NLGQTSLHRA AYCGHLQTCR LLLSYGCDPN

IISLQGFTAL QMGNENVQQL LQEGISLGNS
```

```
                        -continued
EADRQLLEAA KAGDVETVKK LCTVQSVNCR DIEGRQSTPL

HFAAGYNRVS VVEYLLQHGA DVHAKDKGGL

VPLHNACSYG HYEVAELLVK HGAVVNVADL WKFTPLHEAA

AKGKYEICKL LLQHGADPTK KNRDGNTPLD

LVKDGDTDIQ DLLRGDAALL DAAKKGCLAR VKKLSSPDNV

NCRDTQGRHS TPLHLAAGYN NLEVAEYLLQ

HGADVNAQDK GGLIPLHNAA SYGHVDVAAL LIKYNACVNA

TDKWAFTPLH EAAQKGRTQL CALLLAHGAD

PTLKNQEGQT PLDLVSADDV SALLTAAMPP SALPSCYKPQ

VLNGVRSPGA TADALSSGPS SPSSLSAASS

LDNLSGSFSE LSSVVSSSGT EGASSLEKKE VPGVDFSITQ

FVRNLGLEHL MDIFEREQIT LDVLVEMGHK

ELKEIGINAY GHRHKLIKGV ERLISGQQGL NPYLTLNTSG

SGTILIDLSP DDKEFQSVEE EMQSTVREHR

DGGHAGGIFN RYNILKIQKV CNKKLWERYT HRRKEVSEEN

HNHANERMLF HGSPFVNAII HKGFDERHAY

IGGMFGAGIY FAENSSKSNQ YVYGIGGGTG CPVHKDRSCY

ICHRQLLFCR VTLGKSFLQF SAMKMAHSPP

GHHSVTGRPS VNGLALAEYV IYRGEQAYPE YLITYQIMRP

EGMVDG
```

The ROCK inhibitor and/or the tankyrase inhibitor may include any of the following: nucleic acid inhibitory molecules, inhibitory peptides, antibodies, and small molecules, each of which is described in more detail below. Inhibitors of both ROCK1 and ROCK2 and tankyrase are encompassed in the methods of the present invention.

According to one embodiment, the ROCK inhibitor is a small molecule. Exemplary small molecule ROCK inhibitors include, but are not limited to, Y-27632, Glycyl-H-1152, Fasudil, Thiazovivin, GSK429286, CAY10622, AS1892802, and SR 3677. Other small molecule ROCK inhibitors are described in LoGrasso and Feng, "Rho Kinase (ROCK) Inhibitors and Their Application to Inflammatory Disorders," *Current Topics in Med. Chem.* 9:704-723 (2009), which is hereby incorporated by reference in its entirety.

According to one embodiment, the tankyrase inhibitor is a small molecule. Exemplary small molecule tankyrase inhibitors include, without limitation, XAV939, MN-64, IWRI, a pyrimidinone nicotinamide mimetic (e.g., AZ-6102) (see Johannes et al., "Pyrimidinone Nicotinamide Mimetics as Selective Tankyrase and Wnt Pathway Inhibitors Suitable for in Vivo Pharmacology," *Med. Chem. Letters* Jan. 13, 2015, 254-259, which is hereby incorporated by reference in its entirety), and combinations thereof.

According to another embodiment, the ROCK inhibitor and/or the tankyrase inhibitor is an inhibitory molecule (e.g., a nucleic acid inhibitor). Exemplary nucleic acid ROCK inhibitors and tankyrase inhibitors include antisense RNAs or RNAi, such as short interfering RNAs (siRNA), short hairpin RNAs (shRNA), and microRNAs.

The use of antisense methods to inhibit the in vivo translation of genes and subsequent protein expression is well known in the art (see e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, "Antisense DNA and RNA," *Scientific Am.* 262:40-46 (1990), which is hereby incorporated by reference in its entirety). The antisense nucleic acid molecule hybridizes to its corresponding target nucleic acid molecule, such as ROCK1, ROCK2, or tankyrase mRNA, to form a double-stranded molecule, which interferes with translation of the mRNA, as the cell will not translate a double-stranded mRNA. Antisense nucleic acids used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the ROCK1, ROCK2, or tankyrase nucleotide sequence (the nucleotide sequences of ROCK1, ROCK2, and tankyrase are provided supra). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., PCT Publication Nos. WO 2004/015107 to Giese et al., WO 2003/070918 to McSwiggen et al., WO 1998/39352 to Imanishi et al and U.S. Patent Application Publication Nos. 2002/0068708 to Jesper et al., 2002/0147332 to Kaneko et al., and 2008/0119427 to Bhat et al., all of which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

Nucleic acid aptamers that specifically bind to ROCK1, ROCK2, or tankyrase are also useful in the methods of the present invention. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

ROCK inhibitors and tankyrase inhibitors suitable for use in the methods of the present invention may also include inhibitory peptides. Suitable inhibitory peptides include, without limitation, modified ROCK1, ROCK2, or tankyrase peptides that bind, preferably, specifically to the ROCK1, ROCK2, or tankyrase protein but prevent normal ROCK or tankyrase function. Such inhibitory peptides may be chemically synthesized using known peptide synthesis methodology or may be prepared and purified using recombinant technology. Such peptides are usually at least about 5 amino acids in length, but can be anywhere from 5 to 100 amino acids in length. Such peptides may be identified without undue experimentation using well known techniques. Techniques for screening peptide libraries for peptides that are capable of specifically binding to a polypeptide target, in this case ROCK1, ROCK2, and/or tankyrase are well known in the art (see e.g., U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO 84/03506 and WO 84/03564 to Geysen, which are hereby incorporated by reference in their entirety).

In one embodiment, a subject with a tumor comprising a p53 DNA contact mutation is identified prior to administering a ROCK inhibitor (and, optionally, a tankyrase inhibitor).

In another embodiment, identifying a subject with a tumor comprising a p53 DNA contact mutation involves obtaining a tissue sample from the tumor and testing the sample for a p53 DNA contact mutation.

"Obtaining a tissue sample" as used herein, refers to obtaining possession of a sample by "directly acquiring" or "indirectly acquiring" the sample. "Directly acquiring a sample" means performing a process (e.g., performing a physical method such as a surgery, biopsy, or extraction) to obtain the sample. "Indirectly acquiring a sample" refers to receiving the sample from another party or source (e.g., a third party laboratory that directly acquired the sample). Methods described herein can include obtaining a tissue sample from a tumor.

The source of the tissue sample can be solid tissue as from a fresh, frozen, and/or preserved organ, tissue sample, biopsy, or aspirate; blood or any blood constituents; bodily fluids such as cerebral spinal fluid, amniotic fluid, peritoneal fluid, or interstitial fluid; or cells from any time in gestation or development of the subject. Preferably, the tissue sample is from a tumor. The tissue sample can contain compounds that are not naturally intermixed with the tissue in nature such as preservatives, anticoagulants, buffers, fixatives, nutrients, antibiotics or the like. The sample may be preserved as a frozen sample or as formaldehyde- or paraformaldehyde-fixed paraffin-embedded ("FFPE") tissue preparation. For example, the sample can be embedded in a matrix, e.g., an FFPE block or a frozen sample. Typically, the sample is a tumor sample, e.g., includes one or more premalignant or malignant cells. In certain, embodiments, the sample, e.g., the tumor sample, is acquired from a solid tumor, a soft tissue tumor, or a metastatic lesion. In other embodiments, the sample, e.g., the tumor sample, includes tissue or cells from a surgical margin. In an embodiment, the sample, e.g., tumor sample, includes one or more circulating tumor cells ("CTC") (e.g., a CTC acquired from a blood sample). In certain, embodiments, the sample, e.g., the tumor sample, is acquired from a solid tumor, a soft tissue tumor or a metastatic lesion.

Identifying a p53 DNA contact mutation in a tumor can be carried out using methods that are well known in the art. In one embodiment, detecting or identifying a p53 DNA contact mutation comprises sequencing at least a portion of the nucleotide sequence of p53 comprising the mutation. This can be performed by direct sequencing of the gene, such as gene regions comprising the mutation, from a tissue sample obtained from the tumor of a subject. Direct sequencing assays typically involve isolating a DNA sample from the subject using any suitable method known in the art, and cloning the region of interest to be sequenced into a suitable vector for amplification by growth in a host cell (e.g., bacteria) or direct amplification by PCR or other amplification assay. Following amplification, the DNA can be sequenced using any suitable method. One sequencing method involves high-throughput next generation sequencing ("NGS") to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing, which are well known to those of ordinary skill in the art, can be used to carry out the methods of the present invention (i.e., to identify or detect a p53 DNA contact mutation).

In another embodiment, the DNA contact mutation in p53 is identified or detected in a hybridization assay utilizing one or more oligonucleotide probes comprising a nucleotide sequence that is complementary to a nucleic acid molecule comprising p53. In a hybridization assay, the presence or absence of a gene mutation is determined based on the hybridization of one or more oligonucleotide probes to one or more nucleic acid molecules in a sample from the subject. The oligonucleotide probe or probes comprise a nucleotide sequence that is complementary to at least the region of the gene that contains the identified mutation. The oligonucleotide probes are designed to be complementary to the wild type, non-mutant nucleotide sequence and/or the mutant nucleotide sequence of the one or more genes to effectuate the detection of the presence or the absence of the mutation in the sample from the subject upon contacting the sample with the oligonucleotide probe(s).

A variety of hybridization assays that are known in the art are suitable for use in the methods of the present invention. These methods include, without limitation, direct hybridization assays, such as northern blot or Southern blot (see e.g., Ausabel et al., *Current Protocols in Molecular Biology*, John Wiley & Sons, NY (1991), which is hereby incorporated by reference in its entirety). Alternatively, direct hybridization can be carried out using an array based method where oligonucleotide probe(s) designed to be complementary to a particular non-mutant or mutant gene region are affixed to a solid support. A labeled DNA or cDNA sample from the subject is contacted with the array containing the oligonucleotide probe(s), and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array.

In another embodiment, identifying is carried out with an amplification-based assay which amplifies a nucleic acid molecule comprising p53 or a portion thereof. Amplification based assays include assays such as molecular beacon assays, nucleic acid arrays, and allele-specific PCR. Other common genotyping methods include, but are not limited to, restriction fragment length polymorphism assays; primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic Acids Res.* 36(12):e75 (2008), which is hereby incorporated by reference in its entirety), homogeneous primer extension assays, primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier "The Invader Assay for SNP Genotyping," *Mutat Res.* 573(1-2):103-10 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., which are hereby incorporated by reference in their entirety); and oligonucleotide ligation assays, such as ligation with rolling circle amplification, homogeneous ligation, OLA (see U.S. Pat. No. 4,988,617 to Landgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

According to one embodiment, once the p53 DNA contact mutation is identified, a ROCK inhibitor may be administered to the subject.

Pharmaceutical compositions containing a ROCK inhibitor suitable for use in the methods of the present invention can include a pharmaceutically acceptable carrier as described infra, one or more active agents (i.e., the ROCK inhibitor), and a suitable delivery vehicle. Suitable delivery vehicles include, but are not limited to, viruses, bacteria, biodegradable microspheres, microparticles, nanoparticles, liposomes, collagen minipellets, and cochleates.

In one embodiment, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010), PCT Publication No. WO 2011/034798 to Bumcrot et al., PCT Publication No. WO 2009/111658 to Bumcrot et al., and PCT Publication No. WO 2010/105209 to Bumcrot et al., which are hereby incorporated by reference in their entirety.

In another embodiment, the delivery vehicle is a nanoparticle. A variety of nanoparticle delivery vehicles are known in the art and are suitable for delivery of a ROCK inhibitor (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J. Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2):111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat.

No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda, and U.S. Pat. No. 5,059,421 to Loughrey et al., which are hereby incorporated by reference in their entirety.

A liposome containing a ROCK inhibitor can be contacted with the target primary cancer (or tumor) cells under conditions effective for delivery of the inhibitory agent into the cancer (or tumor) cell. For administration to a primary tumor site, the liposomal vesicles need not be targeted to the cancer (or tumor) cells per se.

A liposome and nanoparticle delivery system can be made to accumulate at a target organ, tissue, or cell via active targeting (e.g., by incorporating an antibody or other ligand on the surface of the delivery vehicle). For example, when the target cell is a cancer (or tumor) cell as in the present invention, delivery vehicle may be conjugated to an anti-C3B(I) antibody as disclosed by U.S. Pat. No. 6,572,856 to Taylor et al., which is hereby incorporated by reference in its entirety. Alternatively, the delivery vehicle may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, both of which are hereby incorporated by reference in their entirety.

In another embodiment, the delivery vehicle is a viral vector. Viral vectors are particularly suitable for the delivery of inhibitory nucleic acid molecules, such as siRNA or shRNA molecules, but can also be used to deliver molecules encoding an anti-ROCK antibody. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988); Rosenfeld et al., "Adenovirus-Mediated Transfer of a Recombinant Alpha 1-Antitrypsin Gene to the Lung Epithelium In Vivo," *Science* 252:431-434 (1991); PCT Publication No. WO 93/07283 to Curiel et al.; PCT Publication No. WO 93/06223 to Perricaudet et al.; and PCT Publication No. WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-associated Virus Antisense Vector," *Science* 258:1485-1488 (1992); Ponnazhagan et al., "Suppression of Human Alpha-Globin Gene Expression Mediated by the Recombinant Adeno-associated Virus 2-Based Antisense Vectors," *J. Exp. Med.* 179:733-738 (1994); and Zhou et al., "Adeno-associated Virus 2-Mediated Transduction and Erythroid Cell-specific Expression of a Human Beta-globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell or tissue. One such type of retroviral vector is disclosed in U.S. Pat. No. 5,849,586 to Kriegler et al., which is hereby incorporated by reference in its entirety. Other suitable nucleic acid delivery vehicles include those disclosed in U.S. Patent Application Publication No. 2007/0219118 to Lu et al., which is hereby incorporated by reference in its entirety.

Regardless of the type of infective transformation system employed, it should be targeted for delivery of the nucleic acid to the desired cell type. For example, for delivery into a cluster of cells (e.g., cancer or tumor cells) a high titer of the infective transformation system can be injected directly within the site of those cells so as to enhance the likelihood of cell infection. The infected cells will then express the inhibitory nucleic acid molecule targeting the inhibition of integrin expression. The expression system can further contain a promoter to control or regulate the strength and specificity of expression of the nucleic acid molecule in the target tissue or cell.

In one embodiment, the administering step is carried out to treat a tumor in a subject. Such administration can be carried out systemically or via direct or local administration to the tumor or tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method, or procedure generally known in the art. The mode of affecting delivery of an agent will vary depending on the type of therapeutic agent (e.g., an antibody, an inhibitory nucleic acid molecule, or a small molecule) and the tumor or cancer to be treated.

A ROCK inhibitor of the present invention may be orally administered, for example, with an inert diluent, or with an assimilable edible carrier, or it may be enclosed in hard or soft shell capsules, or it may be compressed into tablets, or it may be incorporated directly with the food of the diet. ROCK inhibitors may also be administered in a time release manner incorporated within such devices as time-release capsules or nanotubes. Such devices afford flexibility relative to time and dosage. For oral therapeutic administration, ROCK inhibitors may be incorporated with excipients and used in the form of tablets, capsules, elixirs, suspensions, syrups, and the like. Such compositions and preparations should contain at least 0.1% of the inhibitor, although lower concentrations may be effective and indeed optimal. The percentage of the inhibitor in these compositions may, of course, be varied and may be between about 0.1% to about 60% of the weight of the unit. The amount of an inhibitor of the present invention in such therapeutically useful compositions is such that a suitable dosage will be obtained.

When the ROCK inhibitor of the present invention is administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, may be preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the inhibitors of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents.

Intraperitoneal or intrathecal administration of ROCK inhibitors can also be achieved using infusion pump devices. Such devices allow continuous infusion of desired compounds avoiding multiple injections and multiple manipulations.

In addition to the formulations described previously, the inhibitors may also be formulated as a depot preparation. Such long acting formulations may be formulated with suitable polymeric or hydrophobic materials (e.g., as an emulsion in an acceptable oil) or ion exchange resins, or as sparingly soluble derivatives, e.g., as a sparingly soluble salt Effective doses of the compositions containing an inhibitor may vary depending upon many different factors, including type and stage of the tumor or cancer, means of administration, target site, physiological state of the subject, other medications or therapies administered, and physical state of the subject relative to other medical complications. Treatment dosages may need to be titrated to optimize safety and efficacy.

For the treatment of tumors, the inhibitors can be administered to a subject in need of treatment alone, or in combination with other antitumor or anticancer substances and/or with radiation therapy and/or with surgical treatment to remove a tumor or cancerous tissue. These other substances or radiation treatments may be given at the same or different times as administering the inhibitor. For example, administration of an inhibitor can be used in combination with mitotic inhibitors, such as taxol or vinblastine; alkylating agents, such as cisplatin, cyclophosphamide, or ifosfamide; antimetabolites, such as 5-fluorouracil or hydroxyurea; DNA intercalators, such as adriamycin or bleomycin; topoisomerase inhibitors, such as etoposide or camptothecin; antiangiogenic agents, such as angiostatin; antiestrogens, such as tamoxifen; and/or other drugs or antibodies that inhibit cancer or tumor cells, such as, for example, GLEEVEC (Novartis) and HERCEPTIN (Genetech).

The term "treat" or "treatment" refer to both therapeutic treatment and prophylactic or preventative measures, where the object is to prevent or slow down (lessen) an undesired physiological change or disorder, such as the development or spread of a tumor or cancer. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if not receiving treatment. Subjects in need of treatment include those already with the condition or disorder (i.e., a tumor or cancer) as well as those prone to have the condition or disorder or those in which the condition or disorder is to be prevented. The term "treat" or "treatment" with respect to a tumor or tumor cells refers to stopping the progression of said cells, slowing down growth, inducing regression, or amelioration of symptoms associated with the presence of said cells.

A further aspect of the present invention relates to a method of identifying a subject as a candidate for treatment. This method involves obtaining a sample from a tumor in a subject and determining the presence of a p53 DNA contact mutation in the sample. The presence of a p53 DNA contact mutation in the sample indicates the tumor is susceptible to targeted treatment with a ROCK inhibitor and the subject is a candidate for treatment.

p53 DNA contact mutations and ROCK inhibitors are described supra.

In one embodiment of this aspect of the present invention, a course of treatment is assigned to the subject based on determining the presence of a p53 DNA contact mutation in the sample. Determining the presence of a DNA p53 mutation in a sample, or identifying the presence of a p53 DNA contact mutation in a sample can be carried out as described supra. For example, and without limitation, determining the presence of a p53 DNA contact mutation may be carried out using a hybridization assay or an amplification assay. Assigning a suitable treatment can involve assigning a treatment as described supra. For example, and according to one embodiment, the assigned course of treatment comprises administering a ROCK inhibitor as described supra.

A further aspect of the present invention relates to a method of treating a tumor in a subject. This method involves administering to a subject having a tumor comprising increased YAP-dependent transcription a Rho-associated protein kinase (ROCK) inhibitor, where the ROCK inhibitor treats the tumor in the subject.

As discussed supra, YAP is a potent transcriptional co-activator that functions as a nuclear effector of the Hippo signaling pathway. In particular, YAP interacts with a variety of DNA-binding transcription factors in the nucleus to activate target gene expression (Yagi et al., "A WW Domain-containing Yes-associated Protein (YAP) is a Novel Transcriptional Co-activator," *EMBO J.* 18:2551-62 (1999); Zhao et al., "TEAD Mediates YAP-dependent Gene Induction and Growth Control," *Genes Dev.* 22:1962-71 (2008), which are hereby incorporated by reference in their entirety).

YAP activity is linked to its cellular abundance and nuclear localization. Amplification of the YAP gene has been observed in several cancer types, including breast (Overholtzer et al., "Transforming Properties of YAP, a Candidate Oncogene on the Chromosome 11q22 Amplicon," *Proc. Natl. Acad. Sci.* 103:12405-10 (2006), which is hereby incorporated by reference in its entirety), medulloblastoma (Fernandez et al., "YAP1 is Amplified and Up-regulated in Hedgehog-associated Medulloblastomas and Mediates Sonic Hedgehog-driven Neural Precursor Proliferation," *Genes Dev.* 23:2729-41 (2009), which is hereby incorporated by reference in its entirety), hepatocellular (HCC) (Zender et al., "Identification and Validation of Oncogenes in Liver Cancer Using an Integrative Oncogenomic Approach," *Cell* 125:1253-67 (2006), which is hereby incorporated by reference in its entirety), and squamous cell carcinomas (Snijders et al., "Rare Amplicons Implicate Frequent Deregulation of Cell Fate Specification Pathways in Oral Squamous Cell Carcinoma," *Oncogene* 24:4232-42 (2005), which is hereby incorporated by reference in its entirety). Increased YAP abundance is also seen in liver (Xu et al., "Yes-associated Protein is an Independent Prognostic Marker in Hepatocellular Carcinoma," *Cancer* 115:4576-85 (2009); Zhao et al., "Inactivation of YAP Oncoprotein by the Hippo Pathway is Involved in Cell Contact Inhibition and Tissue Growth Control," *Genes Dev.* 21:2747-61 (2007), which are hereby incorporated by reference in their entirety), breast (Steinhardt et al., "Expression of Yes-associated Protein in Common Solid Tumors," *Human Pathology* 39:1582-9 (2008), which is hereby incorporated by reference in its entirety), prostate (Zhao et al., "Inactivation of YAP Oncoprotein by the Hippo Pathway is Involved in Cell Contact Inhibition and Tissue Growth Control," *Genes Dev.* 21:2747-61 (2007), which are hereby incorporated by reference in their entirety) and colorectal (Camargo et al., "YAP1 Increases Organ Size and Expands Undifferentiated Progenitor Cells," *Curr. Biol.* 17:2054-60 (2007), which is hereby incorporated by reference in its entirety) cancers, squamous cell (Dong et al., "Genes Differentially Expressed with Malignant Transformation and Metastatic Tumor Progression of Murine Squamous Cell Carcinoma," *J. Cell Biochem. Suppl.* 29:90-100 (1997)), lung and colon adenocarcinomas, and ovarian carcinomas (Steinhardt et al., "Expression of Yes-associated Protein in Common Solid Tumors," *Human Pathology* 39:1582-9 (2008), which is hereby incorporated by reference in its entirety).

As described herein, tumors containing p53 DNA contact mutations show constitutive activation of TEAD/YAP transcription.

The details described supra regarding other aspects of the present invention also apply to carrying the method of this aspect of the present invention.

EXAMPLES

The following examples are provided to illustrate embodiments of the present invention but they are by no means intended to limit its scope.

Materials and Methods for Examples 1-4
Cell Culture and Treatments

HEK293T, MDA-MB-231, MDA-MB-468, U373MB, U251MG, SK-LMS-1, U138MG, LN229, M059J, M059K, and BT-549 cells were grown in Dulbecco's Modified Eagle's Medium (DMEM) (Invitrogen, Carlsbad, Calif.) supplemented with 10% Fetal Bovine Serum (FBS) (Sigma-Aldrich, St. Louis, Mo.), 50 units/ml of penicillin/streptomycin. HCC193, SF295, SK-BR-3, HCC1395, HCC1954, H1299, HCC1937, and HCC1806 cells were grown in RPMI-1640 medium supplemented with 10% FBS and 50 units/ml of penicillin. SK-MEL-2 cells were grown in Eagle's Minimum Essential Medium (MEM) supplemented with 1% non-essential amino acids (NEAA), 10% Fetal Bovine Serum (FBS) (Sigma-Aldrich, St. Louis, Mo.), 50 units/ml of penicillin/streptomycin. MCF10A cells were grown in DMEM/F12 medium supplemented with, 5% horse serum, 10 ug/ml insulin, 100 ng/ml cholera toxin, 0.5 mg/ml hydrocortisone, 20 ng/ml EGF, and 50 units/ml of penicillin/streptomycin. All cells were cultured at 37° C. and 90% humidity in a 5% $CO_2$ incubator. All inhibitors were dissolved in DMSO and treatments were as indicated. DMSO was used as a control in all experiments. ROCK inhibitors were as follows: Y-27632 (Tocris Bioscience, 1254), Glycyl-H-1152 (Cayman Chemical, 13332), Fasudil (Abcam, Ab120306); Verteporfin (Sigma-Aldrich, SML0534), and Simvastatin (Sigma-Aldrich, S6196).

Constructs and Viral Infections pQCXIH-Myc-YAP was a gift from Kunliang Guan (Addgene plasmid # 33091) 44. A pQCXIH vector control was made by removing YAP. pBABE vector control and H-RAS (V12) were as previously described (Mahale et al., "Clonal Selection in Malignant Transformation of Human Fibroblasts Transduced with Defined Cellular Oncogenes," *Cancer Research* 68:1417-1426 (2008), which is hereby incorporated by reference in its entirety). DN TEAD4 was cloned from the pSPORT6 Vector (Dharmacon) with primers containing the restriction sites compatible with the NSPI-CMV-MCS lentiviral vector (Benson et al., "p53-dependent Gene Repression Through p21 is Mediated by Recruitment of E2F4 Repression Complexes," *Oncogene* 33:3959-3969 (2014), which is hereby incorporated by reference in its entirety). The DN mutation, Y429H (TAC→CAC), was introduced by PCR amplification with the mutated 3' primer. Primers were as follows:

```
Forward:
                                      (SEQ ID NO: 9)
TAAGCAGCTAGCGCCACCTTGGAGGGCACGGCCGGCAC;

Reverse complement:
                                     (SEQ ID NO: 10)
ACTATGGGATCCTCATTCTTTCACCAGCCTGTGGATGTGGTGCTGAGC.
``` shp53.1 and shp53.2 were in the pLKO.1 backbone with sequences as follows:

```
    shp53.1:
                                     (SEQ ID NO: 11)
    GTCCAGATGAAGCTCCCAGAA;

shp53.2:
                                     (SEQ ID NO: 12)
    CACCATCCACTACAACTACAT;

shScr:
                                     (SEQ ID NO: 13)
    CCTAAGGTTAAGTCGCCCTCG.
```

The mutant p53 constructs containing the substitution of a single amino acid, were obtained by PCR site-directed mutagenesis using the QuickChange® Lightning Site-Directed Mutagenesis Kit (Agilent Technology, Agilent Technology, Milano, Italy) and the WT-p53 cDNA as template as previously described. Primers were as follow:

```
R175H (g524a)
Forward:
                                          (SEQ ID NO: 14)
ATGGTGGGGGCAGTGCCTCACAACCTC, Reverse:
                                          (SEQ ID NO: 15)
GAGGTTGTGAGGCACTGCCCCCACCAT;

G245S (g733a)
Forward:
                                          (SEQ ID NO: 16)
CCTCCGGTTCATGCTGCCCATGCAGGAAC, Reverse:
                                          (SEQ ID NO: 17)
GTTCCTGCATGGGCAGCATGAACCGGAGG;

R248Q (g743a)
Forward:
                                          (SEQ ID NO: 18)
GAGGATGGGCCTCTGGTTCATGCCGCC, Reverse:
                                          (SEQ ID NO: 19)
GGCGGCATGAACCAGAGGCCCATCCTC;

R273H (g818a)
Forward:
                                          (SEQ ID NO: 20)
AGGACAGGCACAAACATGCACCTCAAAGCTGTTC.

Reverse:
                                          (SEQ ID NO: 21)
GAACAGCTTTGAGGTGCATGTTTGTGCCTGTCCTG.
```

All constructs were verified by DNA sequencing.

To create retroviral stocks, HEK293T cells were co-transfected with the appropriate retroviral expression vector and pCL-ampho packaging plasmid. To create lentiviral stocks, HEK293T cells were co-transfected with the appropriate lentiviral expression vector, pCMVΔR8.74 packaging vector and pMD2 VSVG envelope vector. Titers for each virus stock were determined by colony formation following marker selection in the same assay cell, HT1080, making it possible to compare results using similar amounts of virus in different experiments. Retroviral and lentiviral infections were carried out on all cell lines in the presence of 8 μg/ml polybrene (Sigma). Cells were subsequently selected for antibiotic resistance (2 μg/ml puromycin or 100 μg/ml hygromycin) and expanded as mass populations. In all cases, similar MOIs were used.

Reporter Assays

Cells were plated at $2 \times 10^4$ cells/well in 24 well plates, unless otherwise stated, 48 hours before collection and treated or genetically manipulated as described. Firefly and renilla luciferase activities were assayed with the dual luciferase assay system (Promega, Madison Wis., USA), as directed, and firefly luciferase activity was normalized to renilla luciferase activity. Firefly and renilla luminescence were measured with the TD-20e Luminometer (Turner).

Anchorage-Independent Growth Assay

Growth in soft agar was determined by seeding $2.5 \times 10^3$ MCF10A cells in 1 ml of growth media containing 0.3% agar (BD 214050) on top of 1 ml of 0.48% agar in 35-mm dishes. Cells were fed every 4 days for 3 weeks with 0.2 mL of growth medium. Colonies were stained with 1% crystal violet in ethanol and photographed. Colony density was measured using Image J. Assays were conducted in triplicate.

RNA Extraction and cDNA Synthesis

Total RNA was extracted from cells using QIAshredder (Qiagen, Valencia, Calif., USA) and RNeasy Mini kit (Qiagen) following the manufacturer's instructions. First-strand cDNA synthesis was performed using Superscript II reverse transcriptase (Invitrogen, Carlsbad, Calif., USA) according to the manufacturer's instructions.

Quantitative Real-Time PCR Analysis

Quantitative PCR was carried out using the ViiA™ 7 Real-Time PCR System (Life Technologies) using the FastStart SYBR Green Master mix (Roche, 04673492001). Primers were as follows:

```
CTGF
Forward:
                                          (SEQ ID NO: 22)
CCAATGACAACGCCTCCTG, Reverse:
                                          (SEQ ID NO: 23)
TGGTGCAGCCAGAAAGCTC;

CYR61
Forward:
                                          (SEQ ID NO: 24)
AGCCTCGCATCCTATACAACC, Reverse:
                                          (SEQ ID NO: 25)
TTCTTTCACAAGGCGGCACTC;

ANKRD1
Forward:
                                          (SEQ ID NO: 26)
CACTTCTAGCCCACCCTGTGA, Reverse:
                                          (SEQ ID NO: 27)
CCACAGGTTCCGTAATGATTT;

18S
Forward:
                                          (SEQ ID NO: 28)
GTAACCCGTTGAACCCCATT;

Reverse:
                                          (SEQ ID NO: 29)
CCATCCAATCGGTAGTAGCG.
```

PCR was performed in 384 well plates using 10 μl volumes under the following conditions: 95° C. for 15 min, followed by 40 cycles of 94° C. for 15 sec, 61° C. for 30 sec, and 72° C. for 30 sec. Specificity was verified by a dissociation curve. Results were analyzed with ViiA7 RUO software (Life Technologies).

Cell Proliferation Assay

For clonogenic assay, cells were plated in triplicate at $1 \times 10^3$ cells in 6-well plates. Cells were treated or genetically manipulated as described. After 10 to 14 days, colonies were stained with 1% crystal violet in ethanol and photographed.

Xenograft Tumor Assay $1 \times 10^6$ MDA-MB-231 cells either overexpressing DN TEAD4 or silenced for p53 were inoculated orthotopically into the fat pads of the fifth mammary glands of 6-week-old immunocompromised female SCID mice. The tumor volume was measured with a caliper every 2 weeks, using the formula volume=length×width$^2$/2. At the end of the 4 months observation period, the mice bearing xenograft tumors were sacrificed and the tumor tissues were removed for formalin fixation and preparation of paraffin-embedded sections.

Immunohistochemistry Staining

The paraffin-embedded tissue sections were used for examination of TEAD4 and p53 expression, and HE staining. For immunohistochemistry study, sections were incubated with primary antibodies (1:200 dilutions) overnight at 4° C., followed by biotin-labeled secondary antibody (1:100 dilutions) for 1 h at room temperature. Sections were then incubated with ABC-peroxidase and DAB (diaminobenzedine), counterstained with hematoxylin, and visualized using light microscope.

Example 1 p53 DNA-Contact Mutants Identify a New Class of Hippo Deregulated Human Tumors Missense mutations reside within the DNA binding domain (DBD), some of which inhibit DNA-contact (e.g., R248, R273), which affect amino acids that directly interact with DNA, while p53 conformational mutations (e.g., R175, G245, R282) profoundly alter the 3D conformation of the DBD (Freed-Pastor et al., "Mutant p53: One Name, Many Proteins," *Genes & Development* 26:1268-1286 (2012), which is hereby incorporated by reference in its entirety). Thus, the level of TEAD/YAP transcriptional activity was systematically compared in human tumor lines harboring different types of p53 missense mutations, including the four most frequent hotspot mutations found in human cancers as well as p53 null tumor cells (Table 1).

TABLE 1

Human tumor lines harboring different types of p53 missense mutations.

| Tumor Line | p53 mutation |
|---|---|
| MDA-MB-231 | R280K |
| MDA-MB-468 | R273H |
| U373MG | R273H |
| U251MG | R273H |
| HCC193 | R248Q |
| SF295 | R248Q |
| SK-BR-3 | R175H |
| SK-MEL-2 | G245S |
| SK-LMS-1 | G245S |
| U138MG | I232T/C242F |
| HCC1395 | R175H |
| LN299 | K164E |
| M059J | E286K |
| M059K | E286K |
| HCC1954 | Y163C |
| BT-549 | G245S |
| H1299 | Gene deletion |
| HCC1937 | R386* |
| HCC1806 | Frame shift |

Figure 1B:
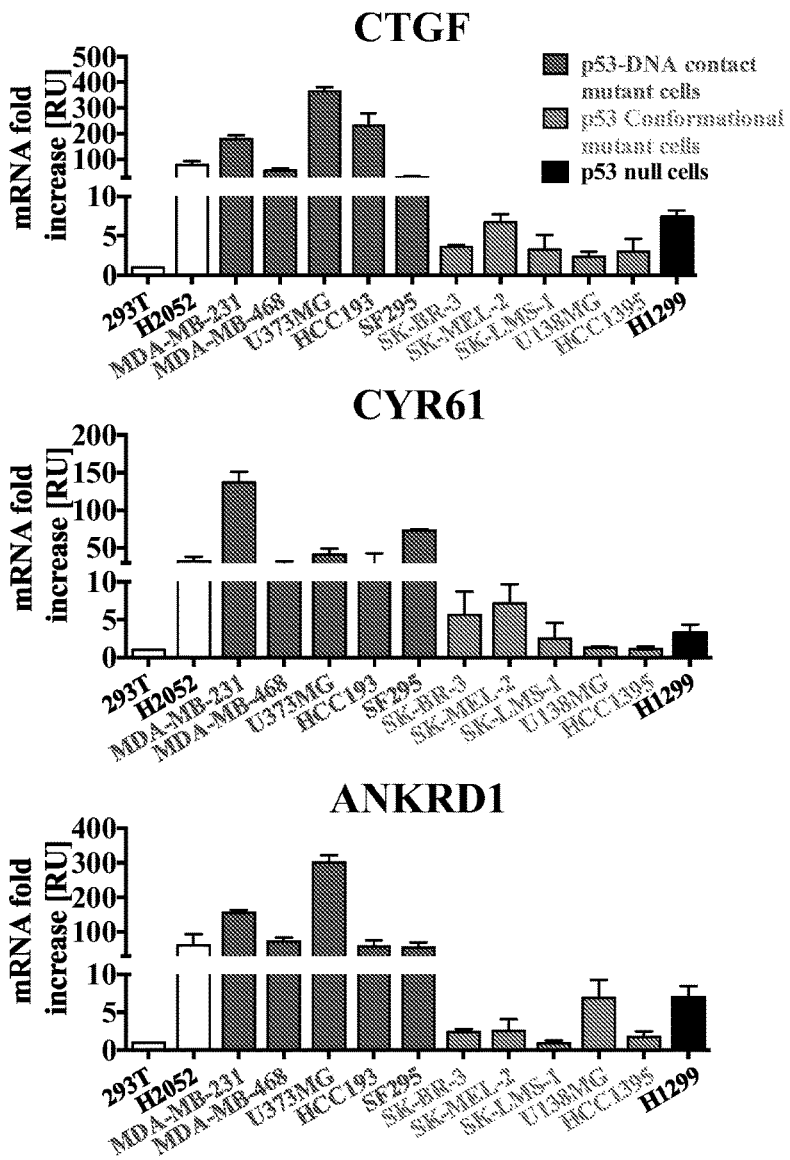

A very high TEAD luciferase reporter activity was detected in all tumor lines analyzed containing p53 DNA-contact mutations but lack of this activity in any with a p53 conformational mutation or null genotype (FIG. 1A). Moreover, p53 DNA-contact mutant-expressing cells exhibited much higher levels of expression of TEAD specific target genes, CTGF, CYR61, and ANKRD1 than p53 conformational mutant-expressing cells (FIG. 1B). These findings suggested that p53 DNA-contact mutants comprised a new class of genetic alterations that upregulate TEAD/YAP transcription in human tumors.

Figure 2A:
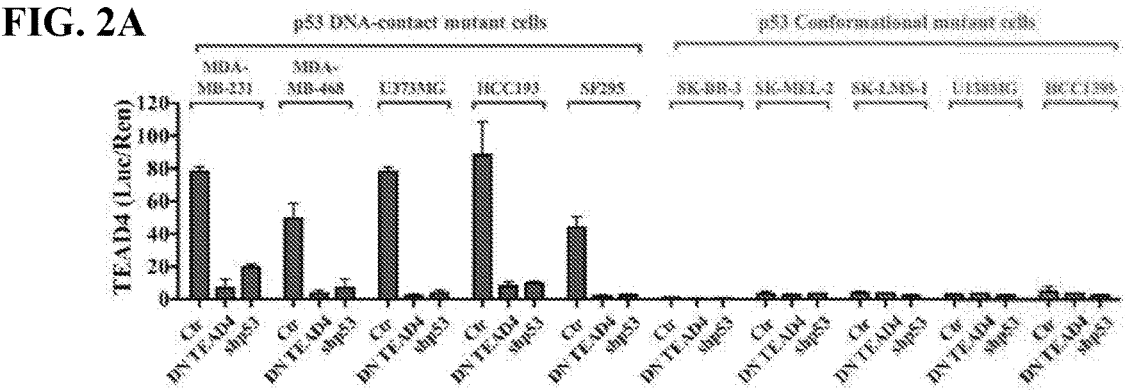
FIGS. 2A-D show p53 knock-down phenocopies TEAD4 inhibition and blocks TEAD/YAP-dependent transcription and proliferation in vitro and in vivo of p53 DNA-contact mutant-containing tumor lines.
Figure 2B:
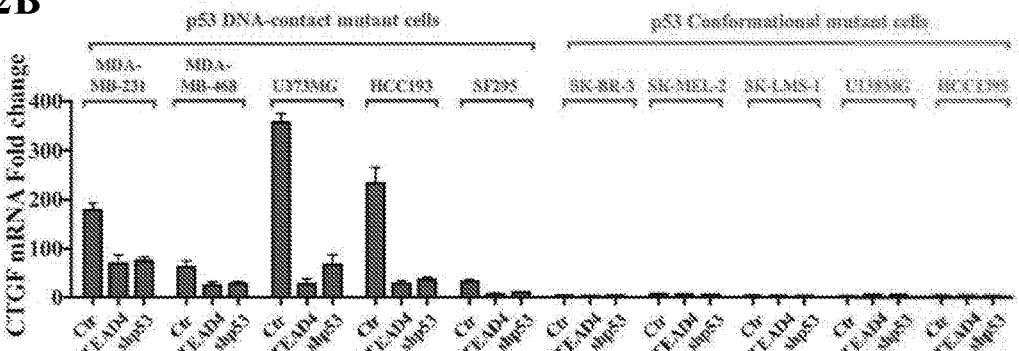

Example 2 p53 Knock Down Phenocopies TEAD4 Inhibition and Blocks TEAD/YAP-Dependent Transcription and Proliferation In Vitro and In Vivo of p53 DNA-Contact Mutant-Containing Tumor Lines To test whether p53 DNA contact mutations were responsible for TEAD/YAP transcriptional upregulation in tumor cells, the abilities of DN TEAD4, which lacks the TEAD DNA binding domain and functions as a dominant negative for TEAD/YAP transcription (Liu-Chittenden et al., "Genetic and Pharmacological Disruption of the TEAD-YAP Complex Suppresses the Oncogenic Activity of YAP," *Genes & Development* 26:1300-1305 (2012), which is hereby incorporated by reference in its entirety) and shp53 to impact TEAD reporter activity were compared. FIG. 2A shows that each of these genetic manipulations markedly inhibited the elevated TEAD reporter activity specifically observed in each p53 DNA contact mutant tumor line analyzed. This same pattern of inhibition was observed for inhibition of expression of the elevated levels of TEAD dependent target genes such as CTGF observed in these same p53 DNA contact mutant tumor lines (FIG. 2B).

Figure 2C:
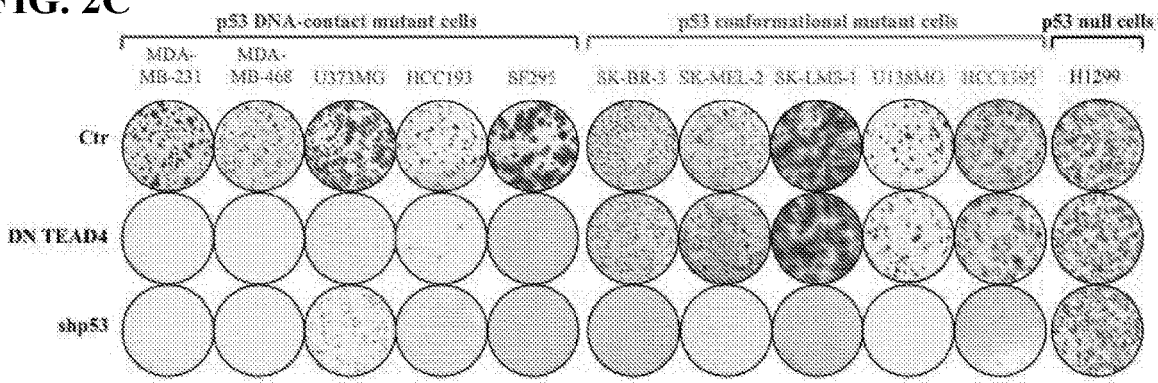
Figure 2D:
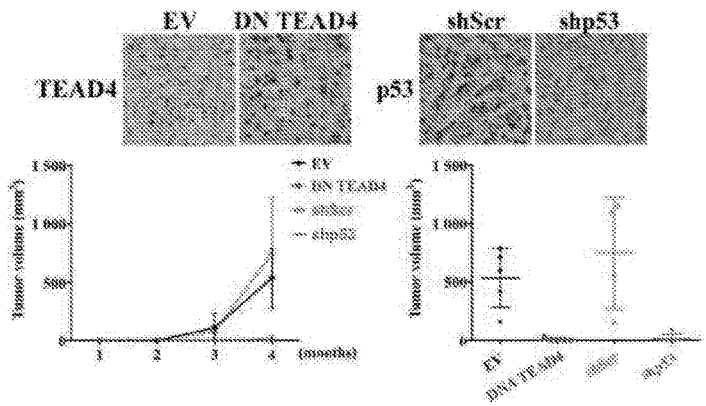

The biological effects of these genetic manipulations on tumor cell proliferation in serum containing medium were next compared. It was observed that colony formation by all p53 mutant tumor cells was strikingly inhibited in response to shp53, which had no effect on colony formation by H1299, a p53 null mutant colon tumor line as a specificity control. These results were consistent with evidence that p53 missense mutations exhibit gain of function (GOF), which appear to be addictive for tumor cells possessing them. Of note, DNTEAD4 was markedly inhibitory to colony formation, specifically by p53 DNA contact mutant containing tumor cells (FIG. 2C). These results correlated DN TEAD4 inhibition of deregulated TEAD/YAP transcription in these p53 mutant tumor cells with specific inhibition of their proliferation. Finally, the effects of DNTEAD4 or shp53 on growth in vivo of MDA-MB-231 breast carcinoma cells, which contain a p53 DNA-contact mutant, R280K, were tested. FIG. 2D demonstrates that either manipulation caused a profound inhibition in the in vivo growth of orthotopically inoculated tumor cells, establishing the importance of p53 DNA contact mutants as oncogenic drivers through upregulation of TEAD dependent transcription.

Example 3

Figure 3A:
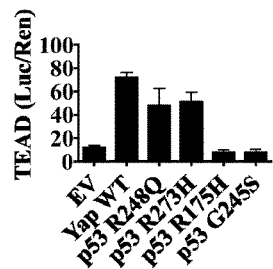
FIGS. 3A-F show that activation of TEAD/YAP-dependent transcription is essential for transformed phenotype induced by p53 DNA-contact mutants in MCF10A cells.
Figure 3B:
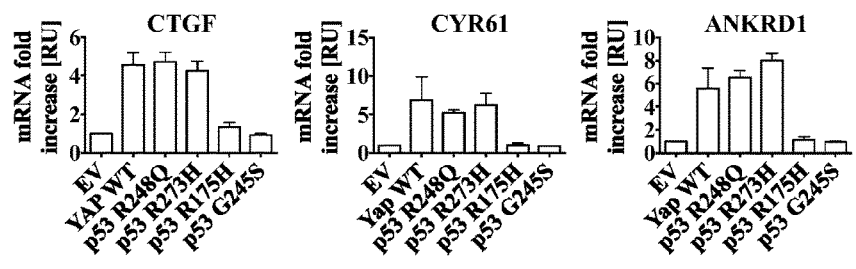
Figure 3C:
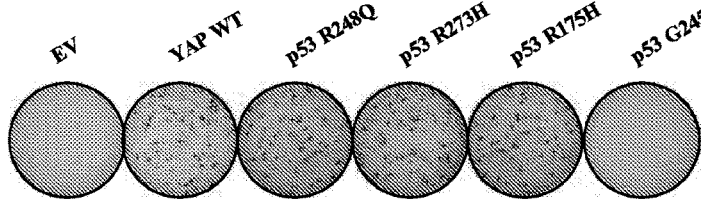

Activation of TEAD/YAP-Dependent Transcription is Essential for Transformed Phenotype Induced by p53 DNA-Contact Mutants in MCF10A Cells To directly demonstrate the ability of p53 DNA-contact mutants to specifically activate TEAD/YAP transcription, two p53 DNA-contact mutants (R248Q and R273H) and two p53 conformational mutants were exogenously expressed by lentiviral mediated transduction of immortalized MCF10A cells. FIGS. 3A-C show that like overexpression of YAP, which served as a positive control, both DNA contact mutants induced high levels of constitutive TEAD/YAP reporter activity and increased levels of TEAD/YAP endogenous target genes, not observed with either p53 conformational mutant tested. Both DNA contact and conformational p53 mutants as well as YAP promoted anchorage-independent colony formation in soft agar by MCF10a cells as previously reported for YAP (Overholtzer et al., "Transforming Properties of YAP, a Candidate Oncogene on the Chromosome 11q22 Amplicon," *PNAS USA* 103:12405-12410 (2006), which is hereby incorporated by reference in its entirety). A p53 mutant (G245S) that lacked the ability to upregulate TEAD dependent transcription, failed to induce colonies in soft agar, suggesting that this mutant does not exert gain of function (FIG. 3C).

Figure 3D:
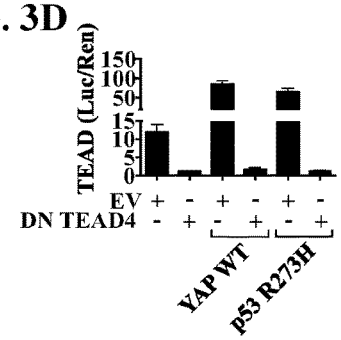
Figure 3E:
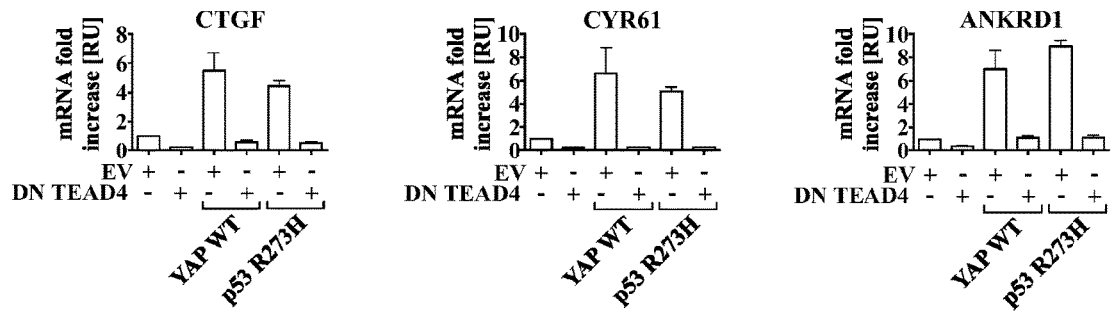
Figure 3F:
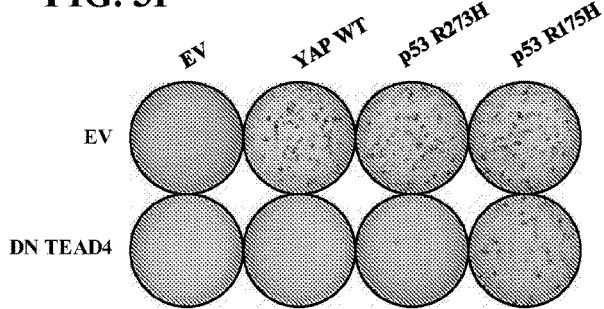

To further establish that the ability of p53 DNA contact mutations to function as oncogenic drivers was mediated by their activation of TEAD/YAP dependent transcription, the effects of DN TEAD4 on both TEAD transcription and the transformed phenotype were tested. FIG. 3D shows that this genetic manipulation markedly inhibited both transcription of the TEAD reporter and the over expression of endogenous Hippo target genes in response to YAP over-expression or p53R273H, a representative DNA contact mutant (FIG. 3E). Moreover, DNTEAD4 specifically blocked colony formation in agar in response to YAP and p53R273H, with no effect on transformation induced by p53R175H, a representative conformational mutant (FIG. 3F). All of these findings provide strong evidence that p53 DNA contact mutations acquire transforming GOF by a mechanism, which causes Hippo pathway deregulation and constitutive TEAD/YAP transcriptional activation.

Example 4

ROCK Inhibitors Specifically Antagonize TEAD Dependent Transcription and the Transformed Phenotype of p53 DNA Contact Mutant Tumor Cells There are few if any agents yet available that specifically target Hippo pathway mutant tumors. The above findings identifying a major new class of these tumors led to seeking to identify potential inhibitors, which would inhibit both TEAD/YAP transcription and transformation by p53 DNA contact mutants with a high degree of specificity. Verteporfin has been reported to inhibit Hippo deregulated transcription at the level of TEAD/YAP protein/protein interactions (Liu-Chittenden et al., "Genetic and Pharmacological Disruption of the TEAD-YAP Complex Suppresses the Oncogenic Activity of YAP," *Genes & Development* 26:1300-1305 (2012), which is hereby incorporated by reference in its entirety). Freed-Pastor and colleagues performed expression array analysis of MDA-MB-468 p53 mutated cells and identified mutant p53 dependent upregulation of several genes involved in the cholesterol synthesis pathway (Freed-Pastor et al., "Mutant p53 Disrupts Mammary Tissue Architecture Via the Mevalonate Pathway," *Cell* 148:244-258 (2012), which is hereby incorporated by reference in its entirety). Moreover, the mevalonate pathway has been proposed as upstream regulator of YAP activity (Sorrentino et al., "Metabolic Control of YAP and TAZ by the Mevalonate Pathway," *Nature Cell Biology* 16:357-366 (2014), which is hereby incorporated by reference in its entirety). Thus, the activity of Simvastatin, a potent inhibitor of the mevalonate pathway, which might inhibit Hippo pathway deregulation by decreasing RhoA posttranslational lipidation, blocking its accumulation at the plasma membrane, was tested. Inhibitors that antagonize the functions of ROCKs that act downstream of RhoA, are known to have diverse biological effects, including enhancing IPS generation (Watanabe et al., "A ROCK Inhibitor Permits Survival of Dissociated Human Embryonic Stem Cells," *Nature Biotechnology* 25:681-686 (2007), which is hereby incorporated by reference in its entirety) and the propagation of normal and tumor cells in organoid culture (Olson, "Applications for ROCK Kinase Inhibition," *Current Opinion in Cell Biology* 20:242-248 (2008); van de Wetering et al., "Prospective Derivation of a Living Organoid Biobank of Colorectal Cancer Patients," *Cell* 161:933-945 (2015), which are hereby incorporated by reference in their entirety). Despite these apparent growth positive effects, a prototype ROCK inhibitor, Y-27632, was also tested on growth of the same battery of p53 mutated human tumor cells.

Figure 4A:
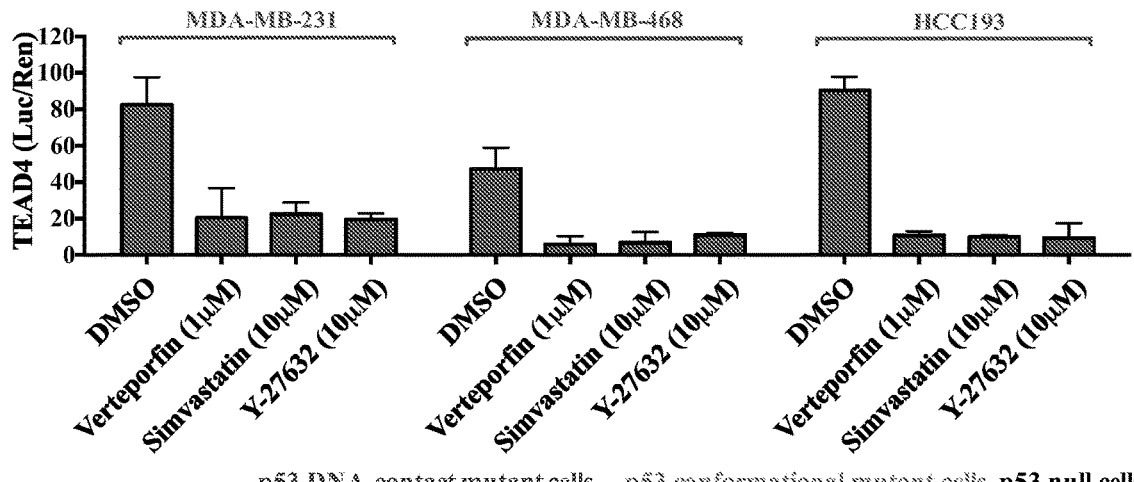
FIGS. 4A-C show that the ROCK inhibitor Y-27632 phenocopies p53 knockdown or DNTEAD4 overexpression in specifically antagonizing the TEAD/YAP transformed phenotype. The graphs in FIG. 4A show analysis of TEAD4 reporter activity in representative tumor lines harboring a p53 DNA-contact mutation.
Figure 4B:
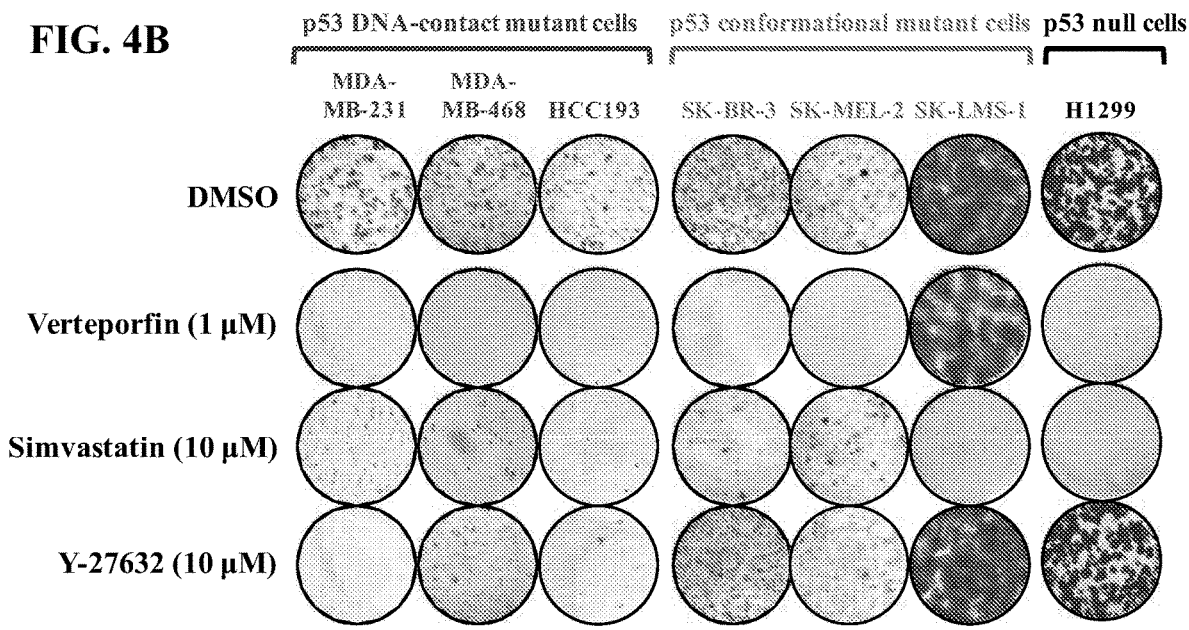
Figure 4C:
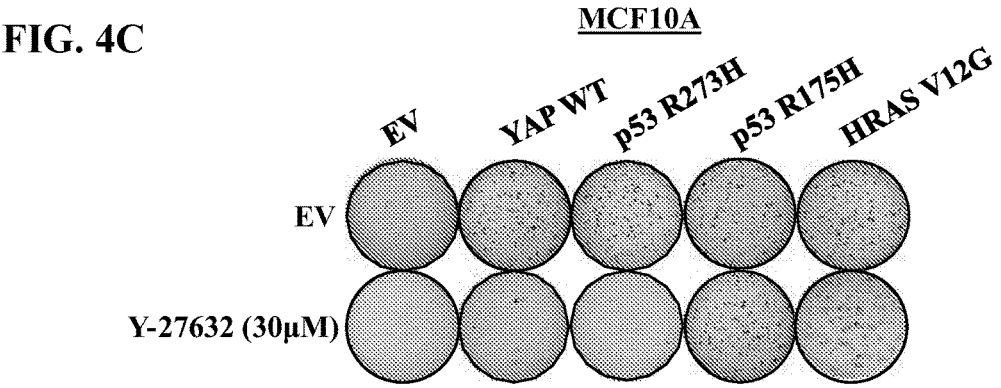

At a concentration level sufficiently high to inhibit proliferation of representative human tumor lines with p53 DNA contact mutations, both Verteporfin and Simvastatin also inhibited the proliferation of representative tumor lines expressing p53 conformational mutants. Simvastatin also inhibited proliferation of SK-LMS-1, expressing a p53 conformational mutation, and p53-null H1299 cells, neither of which like the other p53 conformational mutant tumor cells showed up-regulated TEAD/YAP transcription or was detectably inhibited by DN TEAD4 (see FIG. 2A). Thus, neither of these inhibitors showed a high degree of specificity. In striking contrast, Y-27632 phenocopied the effects of DNTEAD4 in specifically inhibiting the proliferation of p53 DNA contact mutant expressing tumor cells without any obvious growth inhibitory effects on any of the other tumor cells analyzed (FIG. 4B). Similarly, the ROCK inhibitor antagonized both TEAD reporter and TEAD endogenous target gene expression in a manner similar to that of DN TEAD4 (FIG. 4A). As shown in FIG. 4C, Y-27632 also specifically and markedly impaired the transforming ability of MCF10a cells overexpressing YAP and p53 R273H (DNA contact) but not p53 R175H (conformational) or HRAS (V12G) mutants tested under the same conditions. These results confirmed its exquisite specificity as well as potent inhibitory ability for cells transformed by mechanisms involving TEAD/YAP dependent transcription.

Figure 5A:
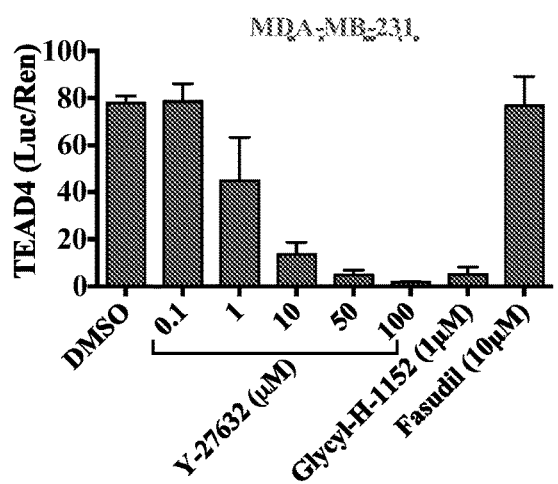
FIGS. 5A-B show that ROCK inhibitors are a new class of inhibitors of Hippo pathway deregulated tumors.
Figure 5B:
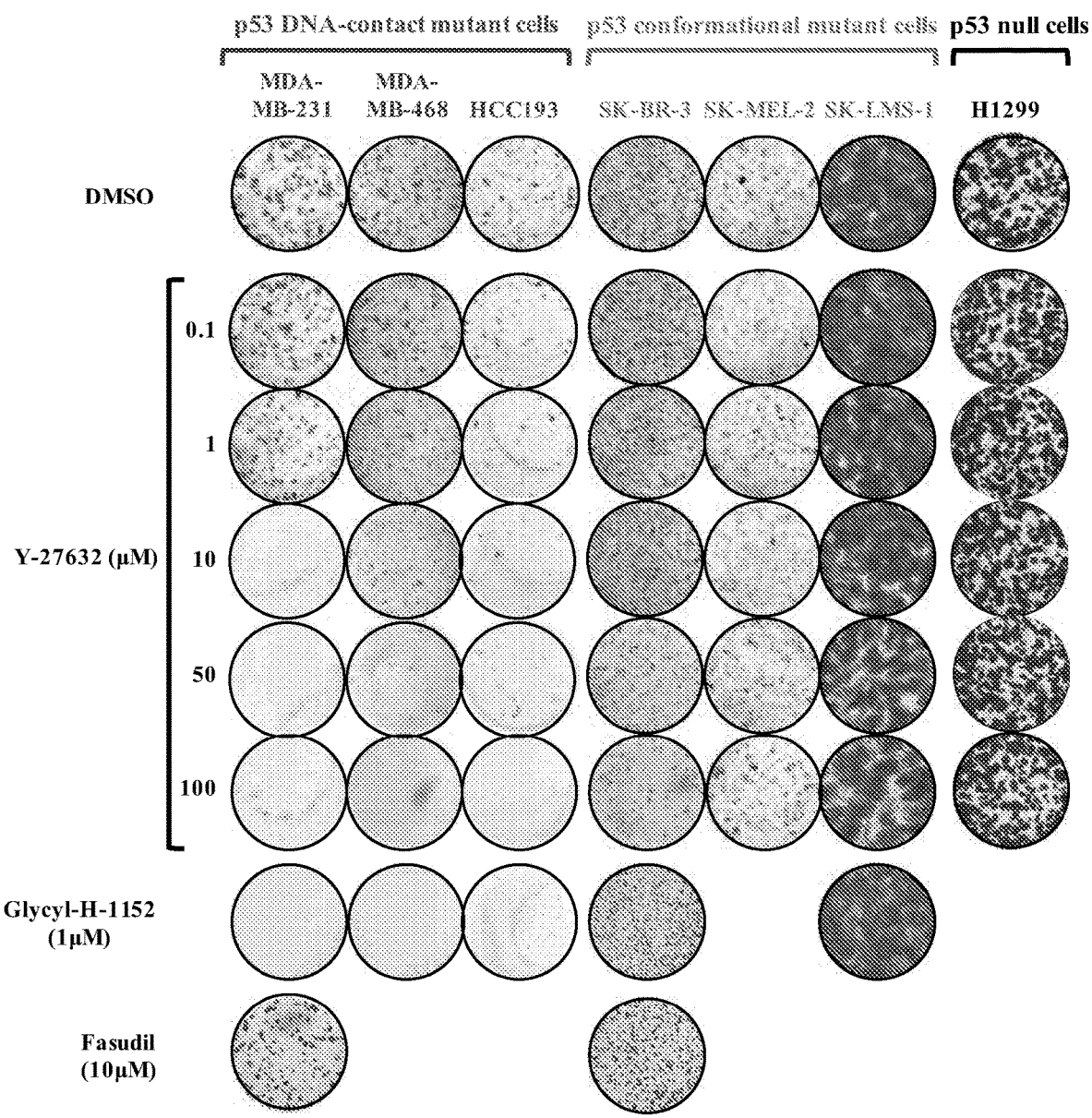

Several ROCK inhibitors with varying potencies in inhibiting in vitro kinase activities of ROCK1 and ROCK2 have been developed (Anastassiadis et al., "Comprehensive Assay of Kinase Catalytic Activity Reveals Features of Kinase Inhibitor Selectivity," *Nature Biotechnology* 29:1039-1045 (2011), which is hereby incorporated by reference in its entirety). FIG. 5 shows a titration of Y-27632 in which marked and specific inhibition of proliferation of tumor cells containing different p53 DNA contact mutants. There was almost complete inhibition of colony formation at concentrations ranging from 10-50 uM of 3 different p53 contact mutant tumor cells with no detectable inhibition of colony formation even at 100 µM for tumor cells with p53 DNA conformational mutants (FIG. 5B). Glycyl-H-1152 is a more potent ROCK inhibitor with a reported $ICD_{50}$ for inhibition of ROCK1 and ROCK2 of 6 and 11.8 nM, respectively (Anastassiadis et al., "Comprehensive Assay of Kinase Catalytic Activity Reveals Features of Kinase Inhibitor Selectivity," *Nature Biotechnology* 29:1039-1045 (2011); Ikenoya et al., "Inhibition of Rho-kinase-induced Myristoylated Alanine-rich C Kinase Substrate (MARCKS) Phosphorylation in Human Neuronal Cells by H-1152, a Novel and Specific Rho-kinase Inhibitor," *Journal of Neurochemistry* 81:9-16 (2002); Sasaki et al., "The Novel and Specific Rho-kinase Inhibitor (S)-(+)-2-methyl-1-[(4-methyl-5-isoquinoline)sulfonyl]-homopiperazine as a Probing Molecule for Rho-kinase-involved Pathway," *Pharmacology & Therapeutics* 93:225-232 (2002), which are hereby incorporated by reference in their entirety). At 1 µM, Glycyl-H-1152 treatment strikingly and specifically inhibited proliferation of tumor lines expressing p53 contact mutants, correlated with marked inhibition of TEAD/YAP dependent transcription (FIG. 5A). Fasudil, which is in the clinic for treatment of pulmonary hypertension and other cardiovascular disorders because of its ability to act as a potent vasodilator, is a far less potent ROCK inhibitor with reported $ICD_{50}$ of 0.33 µM for ROCK2 (Ikenoya et al., "Inhibition of Rho-kinase-induced Myristoylated Alanine-rich C Kinase Substrate (MARCKS) Phosphorylation in Human Neuronal Cells by H-1152, a Novel and Specific Rho-kinase Inhibitor," *Journal of Neurochemistry* 81:9-16 (2002); Ono-Saito et al., "H-series Protein Kinase Inhibitors and Potential Clinical Applications," *Pharmacology & Therapeutics* 82:123-131 (1999), which are hereby incorporated by reference in their entirety). At 10 µM, Fasudil caused little if any inhibition of growth of representative tumor lines containing either a p53 DNA contact or conformational mutant, and caused little if any detectable inhibition of TEAD/YAP dependent transcription. All of these findings argue strongly that potent ROCK inhibitors have the ability to specifically inhibit the proliferation of tumors containing the newly identified class of p53 mutants with lesions that directly impair DNA binding.

Example 5

Figure 6:
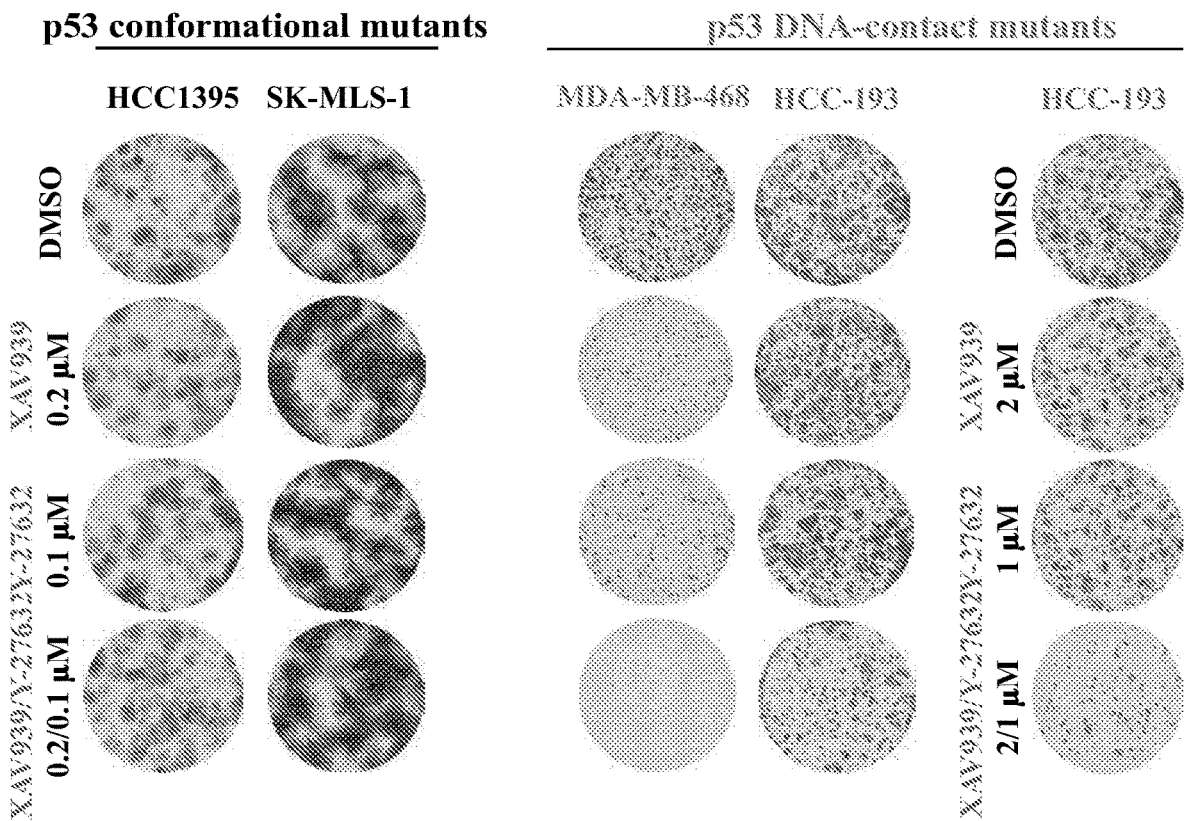
FIG. 6 shows that XAV939 and Y-27632 cooperate to specifically target tumor cells harboring p53 DNA-contact mutations. In particular.

XAV939 and Y-27632 Cooperate to Specifically Target Tumor Cells Harboring p53 DNA-Contact Mutations Y-27632, a prototype inhibitor of Rho kinases (ROCK1 and ROCK2), is able to specifically inhibit the proliferation of p53 DNA-contact mutant tumor lines (FIG. 6), but was not shown to affect the growth of tumor lines harboring mutations in Hippo pathway core components. XAV939 was tested on a newly identified class of Hippo deregulated tumors that harbor p53 DNA-contact mutations. Strikingly, XAV939 was able to inhibit the proliferation of p53-DNA contact tumor lines, MDA-MB-468 and HCC-193, but had no effect on the proliferation of p53 conformational mutant lines, HCC-1395 and SK-LMS-1, which do not show a deregulation in the Hippo pathway (FIG. 6). These findings indicate that tankyrase inhibitors may be more broadly effective than ROCK inhibitors in treating Hippo pathway deregulated tumor cells (FIG. 6).

Figure 7:
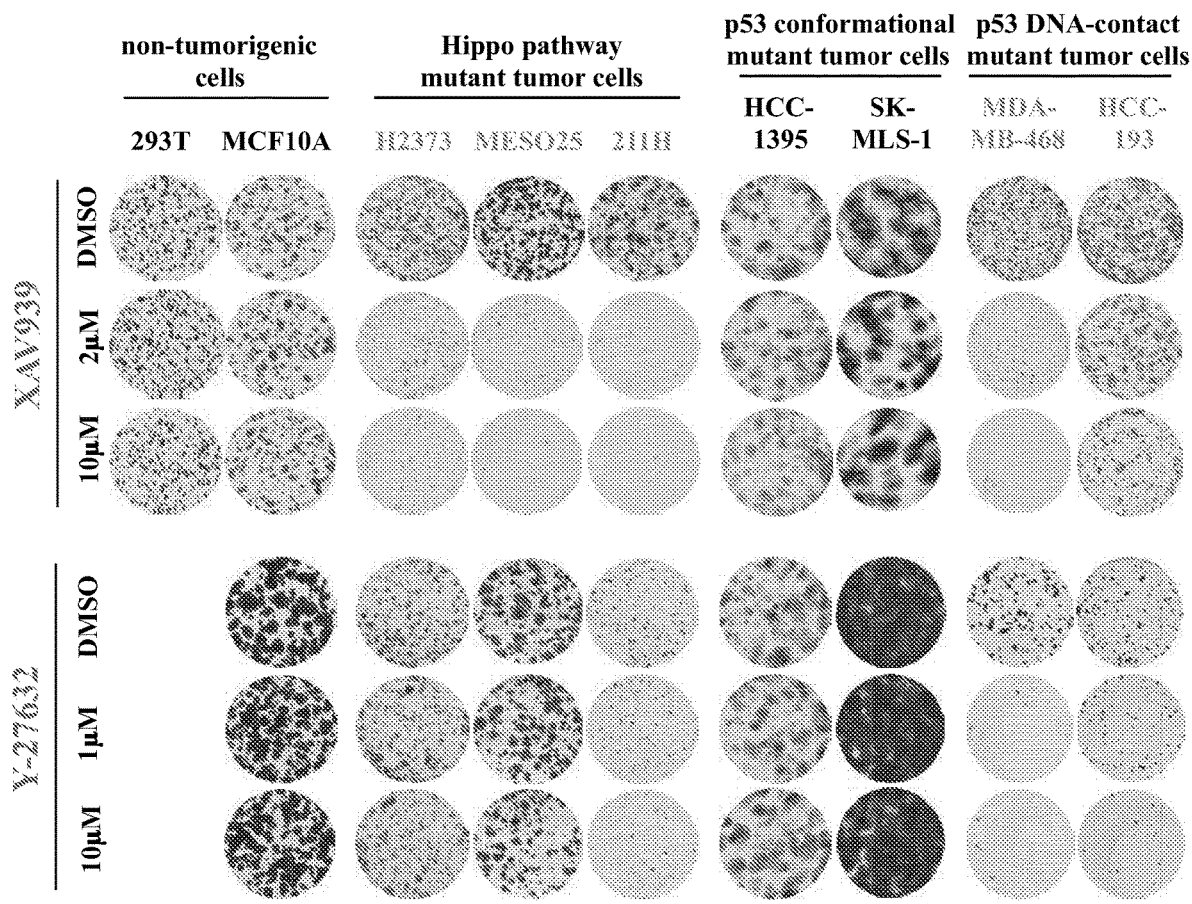
FIG. 7 provides a comparison of the abilities of XAV939 and Y-27632 to inhibit proliferation of tumor cells with different lesions that deregulate the Hippo inhibitor pathway and upregulate TEAD dependent transcription.

Based on the ability of both XAV939 and Y-27632 to antagonize the proliferation of p53-DNA contact tumor lines, it was tested whether these compounds could cooperate at suboptimal (lower) concentration in inhibiting the proliferation of such tumor cells. Strikingly, the combination of suboptimal concentrations of XAV939 and Y-27632 were more effective in inhibiting the proliferation of p53-DNA contact tumor lines compared to the treatment with either agent alone (FIG. 7). Of note, these same combinations of XAV939 and Y-27632 treatment did not affect the proliferation of p53 conformational mutant tumor lines (FIG. 7). Since the targets for ROCK and tankyrase inhibitors are different, these findings indicate that the combination can be cooperative in inhibiting the growth of tumor cells with p53 DNA contact mutations, minimizing the nonspecific toxicity that may be associated with either of these.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of therapeutically treating a breast tumor, a lung tumor, or a glioma comprising a p53 DNA contact mutation in a subject, said method comprising:
   identifying a subject having a breast tumor, a non-small cell lung tumor, or a glioma comprising a p53 DNA contact mutation at an amino acid residue corresponding to position S241, R248, R273, or R280 of SEQ ID NO:2 and
   administering to the subject a Rho-associated protein kinase ("ROCK") inhibitor, wherein the ROCK inhibitor is capable of inhibiting both TEAD/YAP transcription in the tumor and selectively inhibiting proliferation of p53 DNA contact mutant expressing tumor cells without growth inhibitory effects on tumor cells that express p53 DNA conformational mutations, to therapeutically treat the tumor in the subject, wherein the ROCK inhibitor is selected from Glycyl-H-1152, Thiazovivin, GSK429286, CAY10622, SR3677, and a combination thereof.

2. The method according to claim 1, wherein the p53 DNA contact mutation is selected from the group consisting of R280K, R273H, R248Q, S241F, R248W, R273C, and combinations thereof.

3. The method according to claim 1, wherein the subject is a human.

4. The method according to claim 1, wherein said identifying comprises:
   obtaining a tissue sample from the tumor and
   testing the sample for a p53 DNA contact mutation.

5. The method according to claim 4, wherein said testing is carried out using a hybridization assay, ef-an amplification assay, or DNA sequencing.

6. A method of therapeutically treating cancer associated with a breast tumor, a non-small cell lung tumor, or a glioma comprising a p53 DNA contact mutation in a subject, said method comprising:
   identifying a subject having a tumor comprising a p53 DNA contact mutation at an amino acid residue corresponding to position S241, R248, R273, or R280 of SEQ ID NO:2 and
   administering to the subject a Rho-associated protein kinase ("ROCK") inhibitor, wherein the ROCK inhibitor is capable of inhibiting both TEAD/YAP transcription in the tumor and selectively inhibiting proliferation of p53 DNA contact mutant expressing tumor cells without growth inhibitory effects on tumor cells that express p53 DNA conformational mutations, to therapeutically treat the subject for the cancer, wherein the ROCK inhibitor is selected from Glycyl-H-1152, Thiazovivin, GSK429286, CAY10622, SR3677, and a combination thereof.

7. The method according to claim 6, wherein the p53 DNA contact mutation is selected from the group consisting of R280K, R273H, R248Q, S241F, R248W, R273C, and combinations thereof.

8. The method according to claim 6, wherein the subject is a human.

9. The method according to claim 6, wherein said identifying comprises:
   obtaining a tissue sample from the tumor and
   testing the sample for a p53 DNA contact mutation.

10. The method according to claim 9, wherein said testing is carried out using a hybridization assay, an amplification assay, or DNA sequencing.

11. A method of identifying a subject as a candidate for treatment, said method comprising:
    obtaining a sample from a breast tumor, a non-small cell lung tumor, or a glioma in a subject;
    determining the presence of a p53 DNA contact mutation in the sample at an amino acid residue corresponding to position S241, R248, R273, or R280 of SEQ ID NO:2, wherein the presence of a p53 DNA contact mutation in the sample indicates that (i) the tumor is susceptible to targeted treatment with a ROCK inhibitor, wherein the ROCK inhibitor is capable of inhibiting both TEAD/YAP transcription and capable of selectively inhibiting proliferation of p53 DNA contact mutant expressing tumor cells without growth inhibitory effects on tumor cells that express p53 DNA conformational mutations in the tumor, and (ii) the subject is a candidate for treatment;

assigning a course of treatment to the subject based on said determining; and carrying out the assigned course of treatment, wherein the assigned course of treatment comprises administering the ROCK inhibitor, wherein the ROCK inhibitor is selected from Glycyl-H-1152, Thiazovivin, GSK429286, CAY10622, SR3677, and a combination thereof.

12. The method according to claim 11, wherein the p53 DNA contact mutation is selected from the group consisting of R280K, R273H, R248Q, S241F, R248W, R273C, and combinations thereof.

13. The method according to claim 11, wherein the subject is a human.

14. The method according to claim 11, wherein said determining is carried out using a hybridization assay, an amplification assay, or DNA sequencing.

15. The method according to claim 1, wherein the ROCK inhibitor has an $ICD_{50}$ of about 6 nM for ROCK1 and 11 nM for ROCK2.

16. The method according to claim 6, wherein the ROCK inhibitor has an $ICD_{50}$ of about 6 nM for ROCK1 and 11 nM for ROCK2.

17. A method of therapeutically treating a breast tumor, a lung tumor, or a glioma comprising a p53 DNA contact mutation in a subject, said method comprising:

identifying a subject having a breast tumor, a lung tumor, or a glioma comprising a p53 DNA contact mutation at an amino acid residue corresponding to position S241, R248, R273, or R280 of SEQ ID NO:2 and administering to the subject a Rho-associated protein kinase ("ROCK") inhibitor in combination with a tankyrase inhibitor, in suboptimal concentrations, wherein the ROCK inhibitor is capable of inhibiting both TEAD/YAP transcription in the tumor and selectively inhibiting proliferation of p53 DNA contact mutant expressing tumor cells without growth inhibitory effects on tumor cells that express p53 DNA conformational mutations, to therapeutically treat the tumor in the subject, wherein the ROCK inhibitor is Y-27632A and wherein the tankyrase inhibitor is XAV939.

* * * * *

SEQUENCE LISTING

```
<160> NUMBER OF SEQ ID NOS: 29

<210> SEQ ID NO 1
<211> LENGTH: 2591
<212> TYPE: DNA
<213> ORGANISM: Homo sapiens

<400> SEQUENCE: 1
gatgggattg gggttttccc ctcccatgtg ctcaagactg gcgctaaaag ttttgagctt    60
ctcaaaagtc tagagccacc gtccagggag caggtagctg ctgggctccg gggacacttt   120
gcgttcgggc tgggagcgtg cttttcacga cggtgacacg cttccctgga ttggcagcca   180
gactgccttc cgggtcactg ccatggagga gccgcagtca gatcctagcg tcgagccccc   240
tctgagtcag gaaacatttt cagacctatg gaaactactt cctgaaaaca acgttctgtc   300
ccccttgccg tcccaagcaa tggatgattt gatgctgtcc ccggacgata ttgaacaatg   360
gttcactgaa gacccaggtc cagatgaagc tcccagaatg ccagaggctg ctccccccgt   420
ggcccctgca ccagcagctc ctacaccggc ggcccctgca ccagcccct cctggcccct   480 gtcatcttct gtcccttccc agaaaaccta ccagggcagc tacggtttcc gtctgggctt   540
cttgcattct gggacagcca agtctgtgac ttgcacgtac tcccctgccc tcaacaagat   600
gttttgccaa ctggccaaga cctgccctgt gcagctgtgg gttgattcca cacccccgcc   660
cggcacccgc gtccgcgcca tggccatcta caagcagtca cagcacatga cggaggttgt   720
gaggcgctgc ccccaccatg agcgctgctc agatagcgat ggtctggccc ctcctcagca   780
tcttatccga gtggaaggaa atttgcgtgt ggagtatttg gatgacagaa acactttttcg   840 acatagtgtg gtggtgccct atgagccgcc tgaggttggc tctgactgta ccaccatcca   900
ctacaactac atgtgtaaca gttcctgcat gggcggcatg aaccggaggc ccatcctcac   960
```

```
catcatcaca ctggaagact ccagtggtaa tctactggga cggaacagct tgaggtgcg     1020 tgtttgtgcc tgtcctggga gagaccggcg cacagaggaa gagaatctcc gcaagaaagg    1080
ggagcctcac cacgagctgc ccccagggag cactaagcga gcactgccca caacaccag     1140 ctcctctccc cagccaaaga agaaaccact ggatggagaa tatttcaccc ttcagatccg    1200
tgggcgtgag cgcttcgaga tgttccgaga gctgaatgag gccttggaac tcaaggatgc    1260
ccaggctggg aaggagccag gggggagcag ggctcactcc agccacctga agtccaaaaa    1320
gggtcagtct acctcccgcc ataaaaaact catgttcaag acagaagggc ctgactcaga    1380
ctgacattct ccacttcttg ttccccactg acagcctccc accccatct ctccctcccc     1440 tgccattttg ggttttgggt ctttgaaccc ttgcttgcaa taggtgtgcg tcagaagcac    1500
ccaggacttc catttgcttt gtcccggggc tccactgaac aagttggcct gcactggtgt    1560
tttgttgtgg ggaggaggat ggggagtagg acataccagc ttagatttta aggttttac    1620 tgtgagggat gtttgggaga tgtaagaaat gttcttgcag ttaagggtta gtttacaatc    1680
agccacattc taggtagggg cccacttcac cgtactaacc agggaagctg tccctcactg    1740
ttgaattttc tctaacttca aggcccatat ctgtgaaatg ctggcatttg cacctacctc    1800
acagagtgca ttgtgagggt taatgaaata atgtacatct ggccttgaaa ccaccttta    1860 ttacatgggg tctagaactt gacccccttg agggtgcttg ttccctctcc ctgttggtcg    1920
gtgggttggt agtttctaca gttgggcagc tggttaggta gagggagttg tcaagtctct    1980
gctggcccag ccaaaccctg tctgacaacc tcttggtgaa ccttagtacc taaaaggaaa    2040
tctcacccca tcccacaccc tggaggattt catctcttgt atatgatgat ctggatccac    2100
caagacttgt tttatgctca gggtcaattt cttttttctt ttttttttt ttttttcttt     2160 ttctttgaga ctgggtctcg ctttgttgcc caggctggag tggagtggcg tgatcttggc    2220
ttactgcagc ctttgcctcc ccggctcgag cagtcctgcc tcagcctccg gagtagctgg    2280
gaccacaggt tcatgccacc atggccagcc aacttttgca tgttttgtag agatggggtc    2340
tcacagtgtt gcccaggctg gtctcaaact cctgggctca ggcgatccac ctgtctcagc    2400
ctcccagagt gctgggatta caattgtgag ccaccacgtc cagctggaag ggtcaacatc    2460
ttttacattc tgcaagcaca tctgcattt caccccaccc ttccctct tctccctttt      2520 tatatcccat ttttatatcg atctcttatt ttacaataaa actttgctgc cacctgtgtg    2580
tctgaggggt g                                                         2591
```

<210> SEQ ID NO 2
<211> LENGTH: 393
<212> TYPE: PRT
<213> ORGANISM: Homo sapiens

<400> SEQUENCE: 2

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

```
Thr Pro Ala Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Asn
            275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390
```

<210> SEQ ID NO 3
<211> LENGTH: 6650
<212> TYPE: DNA
<213> ORGANISM: Homo sapiens

<400> SEQUENCE: 3

```
gctggttccc cttccgagcg tccgcgcccc gcatgcgcag tctgcccgg cggtctccgt     60 ttgtttgaac aggaaggcgg acatattagt ccctctcagc cccctcgcc ccacccccca    120 ggcattcgcc gccgcgactc gccctttccc cggctgggac cgcagcccct cccagaagct    180
cccccatcag cagccgccgg gacccaacta tcgtcttcct cttcgcccgc tctccagcct    240
ttcctctgct aagtctccat cgggcatcga cctcgcccctg ccccaccgga caccgtagca    300
```

| | |
|---|---|
| gcagcccag cagcgacggg acaaaatggg agagtgaggc tgtcctgcgt ggaccagctc | 360 |
| gtggccgaga ctgatcggtg cgtcgggccg ggccgagtag agccggggac gcggggctag | 420 |
| accgtctaca gcgcctctga gcggagcggg cccggcccgt ggcccgagcg gcggccgcag | 480 |
| ctggcacagc tcctcacccg cccttttgctt tcgcctttcc tcttctccct cccttgttgc | 540 |
| ccggagggag tctccaccct gcttctcttt ctctacccgc tcctgcccat ctcgggacgg | 600 |
| ggacccctcc atggcgacgg cggccgggc ccgctagact gaagcacctc gccgagcga | 660 |
| cgaggctggt ggcgacggcg ctgtcggctg tcgtgagggg ctgccgggtg ggatgcgact | 720 |
| ttgggcgtcc gagcggctgt gggtcgctgt tgccccccggc ccggggtctg gagagcggag | 780 |
| gtccccctcag tgaggggaag acgggggaac cgggcgcacc tggtgaccct gaggttccgg | 840 |
| ctcctccgcc ccgcggctgc gaacccaccg cggaggaagt tggttgaaat tgctttccgc | 900 |
| tgctggtgct ggtaagaggg cattgtcaca gcagcagcaa catgtcgact ggggacagtt | 960 |
| ttgagactcg atttgaaaaa atggacaacc tgctgcggga tcccaaatcg aagtgaatt | 1020 |
| cggattgttt gctggatgga ttggatgctt tggtatatga tttggatttt cctgccttaa | 1080 |
| gaaaaaacaa aaatattgac aacttttttaa gcagatataa agacacaata aataaaatca | 1140 |
| gagatttacg aatgaaagct gaagattatg aagtagtgaa ggtgattggt agaggtgcat | 1200 |
| ttggagaagt tcaattggta aggcataaat ccaccaggaa ggtatatgct atgaagcttc | 1260 |
| tcagcaaatt tgaaatgata aagagatctg attctgcttt tttctgggaa gaaagggaca | 1320 |
| tcatggcttt tgccaacagt ccttgggttg ttcagctttt ttatgcattc caagatgatc | 1380 |
| gttatctcta catggtgatg gaatacatgc ctggtggaga tcttgtaaac ttaatgagca | 1440 |
| actatgatgt gcctgaaaaa tgggcacgat tctatactgc agaagtagtt cttgcattgg | 1500 |
| atgcaatcca ttcatgggt tttattcaca gagatgtgaa gcctgataac atgctgctgg | 1560 |
| ataaatctgg acatttgaag ttagcagatt ttggtacttg tatgaagatg aataaggaag | 1620 |
| gcatggtacg atgtgataca gcggttggaa cacctgatta tatttcccct gaagtattaa | 1680 |
| aatcccaagg tggtgatggt tattatggaa gagaatgtga ctggtggtcg gttggggtat | 1740 |
| ttttatacga aatgcttgta ggtgatacac cttttatgc agattctttg gttggaactt | 1800 |
| acagtaaaat tatgaaccat aaaaattcac ttaccttttcc tgatgataat gacatatcaa | 1860 |
| aagaagcaaa aaaccttatt tgtgccttcc ttactgacag ggaagtgagg ttagggcgaa | 1920 |
| atggtgtaga agaaatcaaa cgacatctct tcttcaaaaa tgaccagtgg gcttgggaaa | 1980 |
| cgctccgaga cactgtagca ccagttgtac ccgatttaag tagtgacatt gatactagta | 2040 |
| attttgatga cttggaagaa gataaaggag aggaagaaac attccctatt cctaaagctt | 2100 |
| tcgttggcaa tcaactacct tttgtaggat ttacatatta tagcaatcgt agatacttat | 2160 |
| cttcagcaaa tcctaatgat aacagaacta gctccaatgc agataaaagc ttgcaggaaa | 2220 |
| gtttgcaaaa aacaatctat aagctggaag aacagctgca taatgaaatg cagttaaaag | 2280 |
| atgaaatgga gcagaagtgc agaacctcaa acataaaact agacaagata atgaaagaat | 2340 |
| tggatgaaga gggaaatcaa agaagaaatc tagaatctac agtgtctcag attgagaagg | 2400 |
| agaaaatgtt gctacagcat agaattaatg agtaccaaag aaaagctgaa caggaaaatg | 2460 |
| agaagagaag aaatgtagaa aatgaagttt ctacattaaa ggatcagttg gaagacttaa | 2520 |
| agaaagtcag tcagaattca cagcttgcta atgagaagct gtcccagtta caaaagcagc | 2580 |
| tagaagaagc caatgactta cttaggacag aatcggacac agctgtaaga ttgaggaaga | 2640 |
| gtcacacaga gatgagcaag tcaattagtc agttagagtc cctgaacaga gagttgcaag | 2700 |

-continued

```
agagaaatcg aattttagag aattctaagt cacaaacaga caaagattat taccagctgc   2760
aagctatatt agaagctgaa cgaagagaca gaggtcatga ttctgagatg attggagacc   2820
ttcaagctcg aattacatct ttacaagagg aggtgaagca tctcaaacat aatctcgaaa   2880
aagtggaagg agaaagaaaa gaggctcaag acatgcttaa tcactcagaa aaggaaaaga   2940
ataatttaga gatagattta aactacaaac ttaaatcatt acaacaacgg ttagaacaag   3000
aggtaaatga acacaaagta accaaagctc gtttaactga caaacatcaa tctattgaag   3060
aggcaaagtc tgtggcaatg tgtgagatgg aaaaaaagct gaaagaagaa agagaagctc   3120
gagagaaggc tgaaaatcgg gttgttcaga ttgagaaaca gtgttccatg ctagacgttg   3180
atctgaagca atctcagcag aaactagaac atttgactgg aaataaagaa aggatggagg   3240
atgaagttaa gaatctaacc ctgcaactgg agcaggaatc aaataagcgg ctgttgttac   3300
aaaatgaatt gaagactcaa gcatttgagg cagacaattt aaaaggttta gaaaagcaga   3360
tgaaacagga aataaatact ttattggaag caaagagatt attagaattt gagttagctc   3420
agcttacgaa acagtataga ggaaatgaag gacagatgcg ggagctacaa gatcagcttg   3480
aagctgagca atatttctcg acactttata aaacccaggt aaaggaactt aaagaagaaa   3540
ttgaagaaaa aaacagagaa aatttaaaga aaatacagga actacaaaat gaaaaagaaa   3600
ctcttgctac tcagttggat ctagcagaaa caaaagctga gtctgagcag ttggcgcgag   3660
gccttctgga agaacagtat tttgaattga cgcaagaaag caagaaagct gcttcaagaa   3720
atagacaaga gattacagat aaagatcaca ctgttagtcg gcttgaagaa gcaaacagca   3780
tgctaaccaa agatattgaa atattaagaa gagagaatga agagctaaca gagaaaatga   3840
agaaggcaga ggaagaatat aaactggaga aggaggagga gatcagtaat cttaaggctg   3900
cctttgaaaa gaatatcaac actgaacgaa cccttaaaac acaggctgtt aacaaattgg   3960
cagaaataat gaatcgaaaa gattttaaaa ttgatagaaa gaaagctaat acacaagatt   4020
tgagaaagaa agaaaaggaa aatcgaaagc tgcaactgga actcaaccaa gaaagagaga   4080
aattcaacca gatggtagtg aaacatcaga aggaactgaa tgacatgcaa gcgcaattgg   4140
tagaagaatg tgcacatagg aatgagcttc agatgcagtt ggccagcaaa gagagtgata   4200
ttgagcaatt gcgtgctaaa cttttggacc tctcggattc tacaagtgtt gctagttttc   4260
ctagtgctga tgaaactgat ggtaacctcc cagagtcaag aattgaaggt tggctttcag   4320
taccaaatag aggaaatatc aaacgatatg gctggaagaa acagtatgtt gtggtaagca   4380
gcaaaaaaat tttgttctat aatgacgaac aagataagga gcaatccaat ccatctatgg   4440
tattggacat agataaactg tttcacgtta gacctgtaac ccaaggagat gtgtatagag   4500
ctgaaactga agaaattcct aaaatattcc agatactata tgcaaatgaa ggtgaatgta   4560
gaaaagatgt agagatggaa ccagtacaac aagctgaaaa aactaatttc caaaatcaca   4620
aaggccatga gtttattcct acactctacc actttcctgc caattgtgat gcctgtgcca   4680
aacctctctg gcatgttttt aagccacccc ctgccctaga gtgtcgaaga tgccatgtta   4740
agtgccacag agatcactta gataagaaag aggacttaat ttgtccatgt aaagtaagtt   4800
atgatgtaac atcagcaaga gatatgctgc tgttagcatg ttctcaggat gaacaaaaaa   4860
aatgggtaac tcatttagta aagaaaatcc ctaagaatcc accatctggt tttgttcgtg   4920
cttcccctcg aacgctttct acaagatcca ctgcaaatca gtctttccgg aaagtggtca   4980
aaaatacatc tggaaaaact agttaaccat gtgactgagt gccctgtgga atcgtgtggg   5040
```

| | |
|---|---:|
| atgctacctg ataaaccagg cttctttaac catgcagagc agacaggctg tttctttgac | 5100 |
| acaaatatca caggcttcag ggttaagatt gctgtttttc tgtccttgct ttggcacaac | 5160 |
| acactgaggg ttttttttat tgcgggtttg cctacaggta gattagatta attattacta | 5220 |
| tgtaatgcaa gtacagttgg gggaaagctt aggtagatat attttttta aaaggtgctg | 5280 |
| cctttttgga tttataagaa aatgcctgtc agtcgtgata gaacagagtt ttcctcatat | 5340 |
| gagtaagagg aagggacttt cactttcaag tggaacagcc atcactatca agatcagctc | 5400 |
| atggaaggag taaagaaaat atctcaaaat gagacaaact gaagttttgt tttttttta | 5460 |
| atgacttaag ttttttgtgct cttgcaagac tatacaaaac tattttaaga aagcagtgat | 5520 |
| atcacttgaa cttcagtgcc ctcactgtag aatttaaaag ccttactgtt gattgcccat | 5580 |
| gttggacttg atgagaaat taaatatctt tcattatgct ttacaaaata ctgtatatgt | 5640 |
| ttcagcaagt ttggggaatg ggagaggaca aaaaaaagtt acatttaatc tatgcatttt | 5700 |
| tgccaagcca tattgagtta ttttactact agagacatta ggaaactaac tgtacaaaag | 5760 |
| aaccaagttt aaaagcattt tgtggggtac atcatttcta taattgtata atgtatttct | 5820 |
| ttgtggtttt aaatgataaa gacattaagt taacaaacat ataagaaatg tatgcactgt | 5880 |
| ttgaaatgta aattattctt agaacacttt caatgggggt tgcattgtcc ttttagtgcc | 5940 |
| ttaatttgag ataattattt tactgccatg agtaagtata gaaatttcaa aaaatgtatt | 6000 |
| ttcaaaaaat tatgtgtgtc agtgagtttt tcattgataa ttggtttaat ttaaatatt | 6060 |
| tagaggtttg ttggactttc ataaattgag tacaatcttt gcatcaaact acctgctaca | 6120 |
| ataatgactt tataaaactg caaaaaatgt agaaggttgc accaacataa aaaggaaata | 6180 |
| tggcaataca tccatgatgt tttccagtta acataggaat taccagataa atactgttaa | 6240 |
| actcttgtcc agtaacaaga gttgattcat atggacagta tgatttattg tttatttttt | 6300 |
| taaccaaata cctcctcagt aatttataat ggctttgcag taatgtgtat cagataagaa | 6360 |
| gcactggaaa accgatcgtc tctaggatga tatgcatgtt tcaagtggta ttgaaagccg | 6420 |
| cactgatgga tatgtaataa taaacatatc tgttattaat atactaatga ctctgtgctc | 6480 |
| atttaatgag aaataaaagt aatttatgga tgggtatctt taattttac tgcaatgtgt | 6540 |
| tttctcatgg ctgaaatgaa tggaaaacat acttcaaatt agtctctgat tgtatataaa | 6600 |
| tgtttgtgaa attccatggt tagattaaag tgtattttta aaagataaaa | 6650 |

<210> SEQ ID NO 4
<211> LENGTH: 6401
<212> TYPE: DNA
<213> ORGANISM: Homo sapiens

<400> SEQUENCE: 4

| | |
|---|---:|
| caaggcggcc ggcggcgacc atggcagcgg gccggcggcg gccgtagtgg cccaggcctg | 60 |
| ggcttcagcc tcccggggcc ccagagggcg gggcggtccg ggccgcgcg gtggcggcgc | 120 |
| cacttccctg ctcccgcccg aggactcctg cgggcactcg ctgaggacca gcggaccggc | 180 |
| ggcgcgaatc tgactgaggg gcggggacgc cgtctgttcc ccgccgctcc cggcagggcc | 240 |
| gggccgggct gggccgggct gggccgggcg ggccctggg agcagcccc aggcggggga | 300 |
| ccgccttgga gacccgaagc cggagctaga ggcaggcggt gggcccgggt ggagtcccgg | 360 |
| ccggagctgg tggttcgggg gcggtgctag gccccgaggc tgcggaccct gagcgcgagg | 420 |
| agcctgagtg cgggtccagc ggtggcggca tgagccggcc cccgccgacg gggaaaatgc | 480 |
| ccggcgcccc cgagaccgcg ccgggggacg gggcaggcgc gagccgccag aggaagctgg | 540 |

-continued

```
aggcgctgat ccgagaccct cgctccccca tcaacgtgga gagcttgctg gatggcttaa    600
attccttggt ccttgattta gattttcctg ctttgaggaa aaacaagaac atagataatt    660
tcttaaatag atatgagaaa attgtgaaaa aaatcagagg tctacagatg aaggcagaag    720
actatgatgt tgtaaaagtt attggaagag gtgcttttgg tgaagtgcag ttggttcgtc    780
acaaggcatc gcagaaggtt tatgctatga agcttcttag taagtttgaa atgataaaaa    840
gatcagattc tgcctttttt tgggaagaaa gagatattat ggcctttgcc aatagcccct    900
gggtggttca gcttttttat gcctttcaag atgataggta tctgtacatg gtaatggagt    960
acatgcctgg tggagacctt gtaaacctta tgagtaatta tgatgtgcct gaaaaatggg   1020
ccaaatttta cactgctgaa gttgttcttg ctctggatgc aatacactcc atgggtttaa   1080
tacacagaga tgtgaagcct gacaacatgc tcttggataa acatggacat ctaaaattag   1140
cagattttgg cacgtgtatg aagatggatg aaacaggcat ggtacattgt gatacagcag   1200
ttggaacacc ggattatata tcacctgagg ttctgaaatc acaaggggt gatggtttct   1260 atgggcgaga atgtgattgg tggtctgtag gtgttttcct ttatgagatg ctagtggggg   1320
atactccatt ttatgcggat tcacttgtag gaacatatag caaaattatg gatcataaga   1380
attcactgtg tttccctgaa gatgcagaaa tttccaaaca tgcaaagaat ctcatctgtg   1440
ctttcttaac agatagggag gtacgacttg ggagaaatgg ggtggaagaa atcagacagc   1500
atcctttctt taagaatgat cagtggcatt gggataacat aagagaaacg gcagctcctg   1560
tagtacctga actcagcagt gacatagaca gcagcaattt cgatgacatt gaagatgaca   1620
aaggagatgt agaaaccttc ccaattccta agcttttgt tggaaatcag ctgcctttca   1680
tcggatttac ctactataga gaaaatttat tattaagtga ctctccatct tgtagagaaa   1740
ctgattccat acaatcaagg aaaaatgaag aaagtcaaga gattcagaaa aaactgtata   1800
cattagaaga acatcttagc aatgagatgc aagccaaaga ggaactggaa cagaagtgca   1860
aatctgttaa tactcgccta gaaaaaacag caaaggagct agaagaggag attaccttac   1920
ggaaaagtgt ggaatcagca ttaagacagt tagaaagaga aaaggcgctt cttcagcaca   1980
aaaatgcaga atatcagagg aaagctgatc atgaagcaga caaaaacga aatttggaaa   2040 atgatgttaa cagcttaaaa gatcaacttg aagatttgaa aaaagaaat caaaactctc   2100 aaatatccac tgagaaagtg aatcaactcc agagacaact ggatgaaacc aatgctttac   2160
tgcgaacaga gtctgatact gcagcccggt taaggaaaac ccaggcagaa agttcaaaac   2220
agattcagca gctggaatct aacaatagag atctacaaga taaaaactgc ctgctggaga   2280
ctgccaagtt aaaacttgaa aaggaattta tcaatcttca gtcagctcta gaatctgaaa   2340
ggagggatcg aacccatgga tcagagataa ttaatgattt acaaggtaga atatgtggcc   2400
tagaagaaga tttaaagaac ggcaaaatct tactagcgaa agtagaactg gagaagagac   2460
aacttcagga gagatttact gatttggaaa aggaaaaaag caacatggaa atagatatga   2520
cataccaact aaaagttata cagcagagcc tagaacaaga gaagctgaa cataaggcca   2580 caaaggcacg actagcagat aaaaataaga tctatgagtc catcgaagaa gccaaatcag   2640
aagccatgaa agaaatggag aagaagctct tggaggaag aactttaaaa cagaaagtgg   2700
agaacctatt gctagaagct gagaaaagat gttctctatt agactgtgac ctcaaacagt   2760
cacagcagaa aataaatgag ctccttaaac agaaagatgt gctaaatgag gatgttagaa   2820
acctgacatt aaaaatagag caagaaactc agaagcgctg ccttacacaa aatgacctga   2880
```

```
agatgcaaac acaacaggtt aacacactaa aaatgtcaga aaagcagtta aagcaagaaa      2940
ataaccatct catggaaatg aaaatgaact tggaaaaaca aaatgctgaa cttcgaaaag      3000
aacgtcagga tgcagatggg caaatgaaag agctccagga tcagctcgaa gcagaacagt      3060
atttctcaac cctttataaa acacaagtta gggagcttaa agaagaatgt gaagaaaaga      3120
ccaaacttgg taagaattg cagcagaaga acaggaatt acaggatgaa cgggactctt        3180
tggctgccca actggagatc accttgacca agcagattc tgagcaactg gctcgttcaa       3240
ttgctgaaga acaatattct gatttggaaa aagagaagat catgaaagag ctggagatca      3300
aagagatgat ggctagacac aaacaggaac ttacggaaaa agatgctaca attgcttctc      3360
ttgaggaaac taataggaca ctaactagtg atgttgccaa tcttgcaaat gagaaagaag      3420
aattaaataa caaattgaaa gatgttcaag agcaactgtc aagattgaaa gatgaagaaa      3480
taagcgcagc agctattaaa gcacagtttg agaagcagct attaacagaa agaacactca      3540
aaactcaagc tgtgaataag ttggctgaga tcatgaatcg aaaagaacct gtcaagcgtg      3600
gtaatgacac agatgtgcgg agaaaagaga aggaaatag aaagctacat atggagctta      3660
aatctgaacg tgagaaattg acccagcaga tgatcaagta tcagaaagaa ctgaatgaaa      3720
tgcaggcaca aatagctgaa gagagccaga ttcgaattga actgcagatg acattggaca      3780
gtaaagacag tgacattgag cagctgcggt cacaactcca agccttgcat attggtctgg      3840
atagttccag tataggcagt ggaccagggg atgctgaggc agatgatggg tttccagaat      3900
caagattaga aggatggctt tcattgcctg tacgaaacaa cactaagaaa tttggatggg      3960
ttaaaaagta tgtgattgta agcagtaaga agattctttt ctatgacagt gaacaagata      4020
aagaacaatc caatccttac atggttttag atatagcaa gttatttcat gtccgaccag      4080
ttacacagac agatgtgtat agagcagatg ctaaagaaat tccaaggata ttccagattc      4140
tgtatgccaa tgaaggagaa agtaagaagg aacaagaatt ccagtggag ccagttggag       4200 aaaaatctaa ttatatttgc cacaagggac atgagtttat tcctactctt tatcatttcc      4260
caaccaactg tgaggcttgt atgaagcccc tgtggcacat gtttaagcct cctcctgctt      4320
tggagtgccg ccgttgccat attaagtgtc ataaagatca tatggacaaa aaggaggaga      4380
ttatagcacc ttgcaaagta tattatgata tttcaacggc aaagaatctg ttattactag      4440
caaattctac agaagagcag cagaagtggg ttagtcggtt ggtgaaaaag atacctaaaa      4500
agcccccagc tccagaccct tttgcccgat catctcctag aacttcaatg aagatacagc      4560
aaaaccagtc tattagacgg ccaagtcgac agcttgcccc aaacaaacct agctaactgc      4620
cttctatgaa agcagtcatt attcaaggtg atcgtattct tccagtgaaa acaagactga      4680
aatatgatgg cccaaaattt attaaaaagc tatattttcc tgagagactg atacatacac      4740
tcatacatat atgtgttccc cttttccctg taatataaat tacaaatctg ggctcctttg      4800
aagcaacagg ttgaaccaac aatgattggt tgatagacta aggatatatg caactcttcc      4860
agacttttcc ataaagctct ctcggcagtc gctcacacta caatgcacac aaggattgag      4920
aagagttaaa ggctaaagaa aacatctttt ctagcttcaa cagagaggtt tcaccagcac      4980
atttaccaga agaatctggg aatggattcc actacagtga tattgactgc atctttaaga      5040
agtgaccatt atactgtgta tatatatata aacacacaca catatatata tatatatata      5100
gtactctaat actgcaagaa ggtttttaa acttcccact ttatttttta tacacattaa       5160
tcagatatca ttacttgctg cagttgcaac tatgcacttg tataaagcca taatgttgga      5220
gtttatatca ctcattcctg tgtacctgat ggaagttgca tgttcatgtt taagcagtta     5280
```

```
ctgtaacaag aagtttaaag ttaattatat cagtttccta atgcttcatg ataggcaact    5340
ttacccattt tgaatgcctt aatttaattt ttttcaaagt ctcagccctg tctgtattaa    5400
aaaacaaaaa aagcgtttac cagctcttag gatgtaaact agctttgtgg aagataaatc    5460
gtgcactatt tttacacata aatagttata tcaatgtcag cctatttgga ttaacaaatg    5520
tttttaaagt attattggtt atagaaacaa taatggatgg tgttggaact aatatatcct    5580
tgatgtctgt ctattattca ttcaactctt tttacagacc tcagtattag tctgtgacta    5640
caaatatttt tatttgcttt aaatttgctg gctaccctag atgtgttttt attcctggta    5700 aagcatttg tgattacatt ttcacactta agattcaaaa ttttcccaa atataaagaa    5760 aactaagaca gactgtagat gcattttaaa tatttaaata tgatcctcag acatgcagct    5820
gtgtgtggca gtatttagt accgggttaa gaaaactggc aactgggaag aagtggcctc    5880
aaaggcactt aatttgattt ttattttta aatgctgtca aagttacagt ttacgcagga    5940
cattcttgcc gtattctcat gatcccagat aagtgtgtgt tttatactgc aacaatatgc    6000
agcaatggta agcgtaaagt tttttttttg tttttgtttt tttttatatt atgaagtctt    6060
ttaacagtct ctctttatat aaatacacag agtttggtat gatatttaaa tacatcatct    6120
ggccaggcat ggtggcttac gcctgtaatc ctagcacttt gggaggccaa gacgggcgga    6180
tcacctgagg tgaggagttc aagaccagcc tgcccaacat agtgaaactc cgtctctacc    6240
aatatacaaa aattagccgg gcatgatggt ggtggcctgt aatcccagct acttgggagg    6300
ctgagacagg agaatcgctt gaacccagga gacggtggtt gcagtgagcg aagatcgagc    6360
cactgcactc cagcctgggc agctgaacaa gactccgtct c                        6401

<210> SEQ ID NO 5
<211> LENGTH: 9599
<212> TYPE: DNA
<213> ORGANISM: Homo sapiens

<400> SEQUENCE: 5
cgaagatggc ggcgtcgcgt cgctctcagc atcatcacca ccatcatcaa caacagctcc      60
agcccgcccc aggggcttca gcgccgccgc cgccacctcc tcccccactc agccctggcc     120
tggcccgggg gaccacccca gcctctccca cggccagcgg cctggccccc ttcgcctccc     180
cgcggcacgg cctagcgctg ccggaggggg atggcagtcg ggatccgccc gacaggcccc     240
gatccccgga cccggttgac ggtaccagct gttgcagtac caccagcaca atctgtaccg     300 tcgccgcgc tcccgtggtc ccagcggttt ctacttcatc tgccgctggg gtcgctccca     360
acccagccgg cagtggcagt aacaattcac cgtcgtcctc ttcttccccg acttcttcct     420
catcttcctc tccatcctcc cctggatcga gcttggcgga gagccccgag gcggccggag     480
ttagcagcac agcaccactg gggcctgggg cagcaggacc tgggacaggg gtcccagcag     540
tgagcggggc cctacgggaa ctgctggagg cctgtcgcaa tggggacgtg tcccgggtaa     600
agaggctggt ggacgcggca aacgtaaatg caaaggacat ggccggccgg aagtcttctc     660
ccctgcactt cgctgcaggt tttggaagga aggatgttgt agaacactta ctacagatgg     720
gtgctaatgt ccacgctcgt gatgatggag gtctcatccc gcttcataat gcctgttctt     780
ttggccatgc tgaggttgtg agtctgttat tgtgccaagg agctgatcca aatgccaggg     840
ataactggaa ctatacacct ctgcatgaag ctgctattaa agggaagatc gatgtgtgca     900
ttgtgctgct gcagcacgga gctgacccaa acattcggaa cactgatggg aaatcagccc     960
```

```
tggacctggc agatccttca gcaaaagctg tccttacagg tgaatacaag aaagacgaac       1020
tcctagaagc tgctaggagt ggtaatgaag aaaaactaat ggctttactg actcctctaa       1080
atgtgaattg ccatgcaagt gatgggcgaa agtcgactcc tttacatcta gcagcgggct       1140
acaacagagt tcgaatagtt cagcttcttc ttcagcatgg tgctgatgtt catgcaaaag       1200
acaaaggtgg acttgtgcct cttcataatg catgttcata tggacattat gaagtcacag       1260
aactgctact aaagcatgga gcttgtgtta atgccatgga tctctggcag tttactccac       1320
tgcacgaggc tgcttccaag aaccgtgtag aagtctgctc tttgttactt agccatggcg       1380
ctgatcctac attagtcaac tgccatggca aaagtgctgt ggatatggct ccaactccgg       1440
agcttaggga gagattgact tatgaattta aaggtcattc tttactacaa gcagccagag       1500
aagcagactt agctaaagtt aaaaaaacac tcgctctgga aatcattaat ttcaaacaac       1560
cgcagtctca tgaaacagca ctgcactgtg ctgtggcctc tctgcatccc aaacgtaaac       1620
aagtgacaga attgttactt agaaaaggag caaatgttaa tgaaaaaaat aaagatttca       1680
tgactcccct gcatgttgca gccgaaagag cccataatga tgtcatggaa gttctgcata       1740
agcatggcgc caagatgaat gcactggaca cccttggtca gactgctttg catagagccg       1800
ccctagcagg ccacctgcag acctgccgcc tcctgctgag ttacggctct gaccccctcca       1860 tcatctcctt acaaggcttc acagcagcac agatgggcaa tgaagcagtg cagcagattc       1920
tgagtgagag tacacctata cgtacttctg atgttgatta tcgactctta gaggcatcta       1980
aagctggaga cttggaaact gtgaagcaac tttgcagctc tcaaaatgtg aattgtagag       2040
acttagaggg ccggcattcc acgcccttac acttcgcagc aggctacaac cgcgtgtctg       2100
ttgtagagta cctgctacac cacggtgccg atgtccatgc caaagacaag ggtggcttgg       2160 tgcccccttca taatgcctgt tcatatggac actatgaggt ggctgagctt ttagtaaggc       2220
atggggcttc tgtcaatgtg gcggacttat ggaaatttac ccctctccat gaagcagcag       2280
ctaaaggaaa gtatgaaatc tgcaagctcc ttttaaaaca tggagcagat ccaactaaaa       2340
agaacagaga tggaaatata cctttggatt tggtaaagga aggagacaca gatattcagg       2400
acttactgag aggggatgct gctttgttgg atgctgccaa gaagggctgc ctggcaagag       2460
tgcagaagct ctgtaccccca gagaatatca actgcagaga cacccagggc agaaattcaa       2520
cccctctgca cctggcagca ggctataata acctggaagt agctgaatat cttctagagc       2580
atggagctga tgttaatgcc caggacaagg gtggtttaat tcctcttcat aatgcggcat       2640
cttatgggca tgttgacata gcggctttat tgataaaata caacacgtgt gtaaatgcaa       2700
cagataagtg ggcgtttact cccctccatg aagcagccca gaaggaagg acgcagctgt       2760 gcgcccctcct cctagcgcat ggtgcagacc ccaccatgaa gaaccaggaa ggccagacgc       2820
ctctggatct ggcaacagct gacgatatca gagctttgct gatagatgcc atgcccccag       2880
aggccttacc tacctgtttt aaacctcagg ctactgtagt gagtgcctct ctgatctcac       2940
cagcatccac cccctcctgc ctctcggctg ccagcagcat agacaacctc actgcccctt       3000
tagcagagtt ggccgtagga ggagcctcca atgcagggga tggcgccgcg ggaacagaaa       3060
ggaaggaagg agaagttgct ggtcttgaca tgaatatcag ccaatttcta aaaagccttg       3120
gccttgaaca ccttcgggat atctttgaaa cagaacagat tacactagat gtgttggctg       3180
atatgggtca tgaagagttg aaagaaatag gcatcaatgc atatgggcac gccacaaat       3240 taatcaaagg agtagaaaga ctcttaggtg gacaacaagg caccaatcct tatttgactt       3300
ttcactgtgt taatcaggga acgattttgc tggatcttgc tccagaagat aaagaatatc       3360
```

```
agtcagtgga agaagagatg caaagtacta ttcgagaaca cagagatggt ggtaatgctg    3420
gcggcatctt caacagatac aatgtcattc gaattcaaaa agttgtcaac aagaagttga    3480
gggagcggtt ctgccaccga cagaaggaag tgtctgagga gaatcacaac catcacaatg    3540
agcgcatgtt gtttcatggt tctcctttca ttaatgccat tattcataaa gggtttgatg    3600
agcgacatgc atacatagga ggaatgtttg gggccgggat ttattttgct gaaaactcct    3660
caaaaagcaa ccaatatgtt tatggaattg gaggaggaac aggctgccct acacacaagg    3720
acaggtcatg ctatatatgt cacagacaaa tgctcttctg tagagtgacc cttgggaaat    3780
cctttctgca gtttagcacc atgaaaatgg cccacgcgcc tccagggcac cactcagtca    3840
ttggtagacc gagcgtcaat gggctggcat atgctgaata tgtcatctac agaggagaac    3900
aggcataccc agagtatctt atcacttacc agatcatgaa gccagaagcc ccttcccaga    3960
ccgcaacagc cgcagagcag aagacctagt gaatgcctgc tggtgaaggc cagatcagat    4020
ttcaacctgg gactggatta cagaggattg tttctaataa caacatcaat attctagaag    4080
tccctgacag cctagaaata agctgtttgt cttctataaa gcattgctat agtgatgaat    4140
agtatgagta actgatacat actcaactgc tactgttccc tttgaggaaa tgtttacagg    4200
ggcggccttt taacatatct caggctcatt ttcattgcaa ttatccattt ctaaaacaag    4260
attgcttcga tctagacttg gaaatggaaa ataagaaaac caatgctttt tcaaatgttc    4320
acaattcaca cactacattt gttttgttat gcatgacgtg tctataacaa atatacacat    4380
acgacaggca acaagcttgt ttttgatttg ccagacatgc atcattggct attgtttgtt    4440
tgttttttgt tttttttgtgt tttttgggtt actttgaaaa tgagccagag ccttcttgag    4500
gatattttgc acaaagtcac gctgacaaaa tcattagcag tgcaacccaa gcttctggct    4560
gagcaagatt cagtttccac ttttttaaaat tttttttattt tgctctgtag ctgcacttct    4620
cgttatcata aattgagatg aaaaggaaaa aacatcaagt tttagtacct ttttatgaat    4680
tggcctatct tacaagagaa gggcacaaac accaacctga cttaggaacg cctaaattca    4740
gagaagtcaa agccggtgaa ggccacttgc tctttccaac acaagcctgc cacagaggtc    4800
ttcgggacag tactggagat gcaggttgac acgggcttga gttccaaggt gaaaaaactg    4860
gggaggctgt gaaggaagag ctgcattaag gagggtgagg agcgtgtggt tctgtatcat    4920
ggcagcccca atggatccag gggatgcctc caaaaaatac atgcttccct tcccttaatc    4980
tgtactgttg ggattgttac ccctccaaat tagctgcctt atttcaaaag tcagtgaaat    5040
tactgcactt gatgagggtc acaaaaatac cacttgattg ttttctttagt tgagaatgct    5100 gggattcaga ctcgaatagt ggatagatac acacaaatgc aaggactttt tgtttactc    5160 cagatttggg gtttattttg agtggcatgc ttcaaatagt tcataaagat ccttgcatta    5220
aatttctgaa ccatttcttc aaacttctta gtgtgtttag acaaggagaa caaaaattga    5280
aaccaaagcc ctttctgtta tttttttcaat gaaggtgaga agaaatacc atacaatttt    5340 ctttgtgaaa ttactgttta ttttcatcaa catttaccaa gtgccattga catttataaa    5400
aaaaaatgat cctttatagt tcttacactt gcccttttca ccttaactga atatgaattg    5460
agtgcactaa cttatttact tgatatactg tgcatctact ctgctttgaa gcgaaagaaa    5520
tataaacacg aggaggaata ggaaagacag tgtgacacaa acttgccatt gcaattcaaa    5580
gccctgaaaa cgatgggttt aatgcaaggt gattaagctg tgacctcctt taatctcctg    5640
aagcaaaata aaatggttac atgcaaaact tctagaaata gactcttaaa atatatacat    5700
```

```
tttgctttga ttttggcttc aacccagtgc tggaactagg catccagact agtttgaatg   5760
tttgtagctg aattttttatg ggtcctcaaa attaaatcga gaattagcct cagttgttgc   5820
ttcttttgaa gtttcagtga cccaagctgg gtgtttgtgt cttggctact tgtttaatag   5880
cactagaatt ccaggtgaag ctttgagagt tgatattcat taagagggct ttttttcccc   5940
ttctttcctt ctcttttgct gtaacaaagg gttgaagaaa ttgccatctg tgtagttttc   6000
agtagctgtc aagtgtgtct tacttacctt cccccagacg tagtttaaaa tggtaaacac   6060
agctgtgatt tttagttaag taaaagagtt aatatgatat agatatggaa agctttatgg   6120
cttcattaaa aagataaacc actacctaac tgtggttgta tgttgtttcc atcatactaa   6180
ctagatgaat ggatgcgcca gttttcatct tggtccttac acttgagaag ttaaactgtg   6240
gttcagtatt taaactgcca gtgttatacg tctcatgctc tgtgtgccag gtgaaggtac   6300
tgtgtaagga agacatttgc ggtgcttctt gtcctataat gattcaagta tatagtagtt   6360
cttgaaagag tgtgcatata ttactcatct gcttaagaga gtgggttaat ggatatatca   6420
gaggagccaa atacattttt ttcagaactt gaaaaccaaa ggtcatcatg agtgcactca   6480
aaagttagga caagtttatt acatttggga ttttcatctg tagccgtatg aagaacccctt   6540 tccaatataa agcatggca ttaaattagg ctgaagtctt ttatttttg tatatgtact   6600 atatagaaat actagcaagt taggatcatc caatatggcc taccccgaaa tggcccctct   6660
gtttccctaa ccacatggaa gaaagaatct gaacgtctcc accggctcta cccgagttcc   6720
aaaactaaag ggcttctcca gacctgatgg ttccagttta cctgctgttg gcctgctgga   6780
tacttgactc aggcataaat taagtgccct ggtcccgaac tttctccctg tatttgacct   6840
ccttccctct ttcctaaatt actagtctgg aattaaaatt agctccagca atgacctttg   6900
actccattca ttttctcctc atcttgggtc ttaaaaaagg agaccagata cctcctagct   6960
tttgtatcac aaccaggaat gggtattagg cctcatgcgc tttgctcaga acactgccgc   7020
tttgttaaca aatgacagca tggaacccag agttttgatt cgatgcaaaa taacagcagt   7080
gcaaccagga ttcttgtttt cctttttcctt cttggagttt ggaatttcta gcttttcaag   7140
cagcataagt agaatcaaca ttaggatgtt ttcatgaaat agcatcctta tacttctttg   7200
agcttgatgt tagtggctag actgatttcc ctttgctctc aaaatacaaa gtgcattgaa   7260
gtatacagag aaatgcctga atatggcaag caaataatgt agattaacat tctattattg   7320
tatccgtttt acaaaaaata aaattttgat atatgccgga gaacggcatt agaatgcaat   7380
aagttgtcta ggttttttctg tttcagtgtc tctcccaatg gcacgaaggg ttattgggca   7440
ttgtccccac ccccgccttt ttaacatgtg cactatctgg attcctgtaa atggccttgc   7500
aaacagaagt ggtgtgtatt ttcaagcacc tttccccccat tgtatccgaa tccctcttgt   7560
gtgatatctg tgacaaatag ccttcttctt gtgttttctg ttggactaat tgtctcacgt   7620
aaagctatag accttactaa tttggcaggt attcaaaact gccattaaga taggatttca   7680
tgtcagatac gtatttaaag agtaaagtca aatttgttta atgtcagatc agtgacagaa   7740
gtgaaaagaa agtaattgtg aaagtgatgt ttgagctatt gtacacatct agcatatgga   7800
aagcaaatgc actcgaaaac tactattcta gaacatgagg cttcttcagc aacttgtgca   7860
ctctgccatt aataaattaa attttccccc tctagaaagc cttaactatg gcggaaactt   7920 tttaacctttt tatattttaa taaataaaac attgtagtcc catttcttag tgtttgaaag   7980
gtgtgtcagt gagtcggcca tgtctccatg tgtttcagac ctgttcatct tatttttatga   8040 tggtatattt cataagtaat attcccttac atgcaatgga gctgattaaa attaatccat   8100
```

```
ttcaatttct ccatattgga acttcctcag ctaccagatt tctggtttgg agaagtgctg    8160
gaaagatttc aaagcctatt cagttgtgta tgtggggata cgacagcaac tgtgataacct   8220
tgtagaatat gagtgatatg caagctgtgt tttttaattg ttttaaaatg taaattatgg   8280
ttatgctaaa gtgaaaacct agaggaagct aatgatttta tatactttgc acgaccaaat   8340
atggtcgtag tatgacgagt tttatacatt gccagagagt tctgcctcct ctgaaataac   8400
attcgcactg tagattgcat ttcggctttt cctcctttca cattctttt tgctttacac    8460
ttcacgtctt cgcacctgcc ctacctccca tcctttcaaa gaggtttctt tcacgttcca   8520
gaattcagat tgttctgtga tttcttttac atcagtctac ccatttctgc aggcagccct   8580
gaaagccctt gtgttgattc agagtgtttg cagagaaatg cagttgaacc ctggtagtgg   8640
ggtgtccctc acacccgc gcaccctcc caaagttcag gatgaaaggc tagaaaaccc      8700
attcaaagtt aggaaagaac acagatcttt gaggccgata gcctagacct agaagatgac   8760
cttgagtatg taaacattgt ctccgtgaca caaaacactg aaactcttca tgtgcatata   8820
acacctgctt ctgctcccat tgtttcaagc tcatcttatc tttgtagtag taatgtttgt   8880
ctttgatacc tacaaactaa aaaggtactt ttatcaaggt ttctcaaaac atttacaaaa   8940
ccagctttga gaaaatgtta tgttgcctgg caacagcact cggagtagta attgtgtttt   9000
ctcattgtga tgttggtctg tgtgagcaac cagtgtagtg actctttggt tcattattcg   9060
tgttgttttt attttttagtc tctgtgtgac ccaacagtgg caggggttac aaccccctct   9120
cctttctttt ttgtatttat ctatttgtag gattgtcaga tcaagtacaa gatgcccagt   9180
taagtttgaa tttcagagaa acaatttcac gttaagaatg tttcatgcaa tatttggcat   9240
atatttacag taaaagcatt cattatttgt ctgaaattca aatttaactg agcatgctgg   9300
tttttctcat tgtttggttt ttctaaatct ggcaatccta cagctgtggt catgggaaat   9360
cacctacagc atgttaaagt cctctagtca tcatctcgtc acctgaaatg gaagtccttt   9420
ttccctcacc ctccacttct ttccaaagga gggcatcaag gaacttaacc tgcctgcctg   9480
gtgggtttct atttaagaca tctttgtgat tatatttaac ctgcaattgt gctttggctt   9540
aatgtctagc tcactgtact tgtaaatgat taatattcaa taaaaccatt tttaaagta    9599
```

<210> SEQ ID NO 6
<211> LENGTH: 1327
<212> TYPE: PRT
<213> ORGANISM: Homo sapiens

<400> SEQUENCE: 6

Met Ala Ala Ser Arg Ser Gln His His His His His Gln Gln
1               5                   10                  15

Gln Leu Gln Pro Ala Pro Gly Ala Ser Ala Pro Pro Pro Pro
            20                  25                  30

Pro Pro Leu Ser Pro Gly Leu Ala Pro Gly Thr Thr Pro Ala Ser Pro
        35                  40                  45

Thr Ala Ser Gly Leu Ala Pro Phe Ala Ser Pro Arg His Gly Leu Ala
    50                  55                  60

Leu Pro Glu Gly Asp Gly Ser Arg Asp Pro Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
            100                 105                 110

```
Ala Ala Gly Val Ala Pro Asn Pro Ala Gly Ser Gly Ser Asn Asn Ser
            115                 120                 125

Pro Ser Ser Ser Ser Pro Thr Ser Ser Ser Ser Ser Ser Pro Ser
        130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

Gly Asp Val Ser Arg Val Lys Arg Leu Val Asp Ala Ala Asn Val Asn
            195                 200                 205

Ala Lys Asp Met Ala Gly Arg Lys Ser Ser Pro Leu His Phe Ala Ala
    210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
                260                 265                 270

Ala Asp Pro Asn Ala Arg Asp Asn Trp Asn Tyr Thr Pro Leu His Glu
            275                 280                 285

Ala Ala Ile Lys Gly Lys Ile Asp Val Cys Ile Val Leu Leu Gln His
            290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
            355                 360                 365

Lys Ser Thr Pro Leu His Leu Ala Ala Gly Tyr Asn Arg Val Arg Ile
    370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Lys His Gly Ala Cys Val Asn Ala Met Asp
            420                 425                 430

Leu Trp Gln Phe Thr Pro Leu His Glu Ala Ala Ser Lys Asn Arg Val
            435                 440                 445

Glu Val Cys Ser Leu Leu Leu Ser His Gly Ala Asp Pro Thr Leu Val
    450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
    515                 520                 525
```

```
Ala Val Ala Ser Leu His Pro Lys Arg Lys Gln Val Thr Glu Leu Leu
    530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
            580                 585                 590

Thr Ala Leu His Arg Ala Ala Leu Ala Gly His Leu Gln Thr Cys Arg
        595                 600                 605

Leu Leu Leu Ser Tyr Gly Ser Asp Pro Ser Ile Ile Ser Leu Gln Gly
    610                 615                 620

Phe Thr Ala Ala Gln Met Gly Asn Glu Ala Val Gln Gln Ile Leu Ser
625                 630                 635                 640

Glu Ser Thr Pro Ile Arg Thr Ser Asp Val Asp Tyr Arg Leu Leu Glu
                645                 650                 655

Ala Ser Lys Ala Gly Asp Leu Glu Thr Val Lys Gln Leu Cys Ser Ser
            660                 665                 670

Gln Asn Val Asn Cys Arg Asp Leu Glu Gly Arg His Ser Thr Pro Leu
        675                 680                 685

His Phe Ala Ala Gly Tyr Asn Arg Val Ser Val Val Glu Tyr Leu Leu
    690                 695                 700

His His Gly Ala Asp Val His Ala Lys Asp Lys Gly Gly Leu Val Pro
705                 710                 715                 720

Leu His Asn Ala Cys Ser Tyr Gly His Tyr Glu Val Ala Glu Leu Leu
                725                 730                 735

Val Arg His Gly Ala Ser Val Asn Val Ala Asp Leu Trp Lys Phe Thr
            740                 745                 750

Pro Leu His Glu Ala Ala Ala Lys Gly Lys Tyr Glu Ile Cys Lys Leu
        755                 760                 765

Leu Leu Lys His Gly Ala Asp Pro Thr Lys Lys Asn Arg Asp Gly Asn
    770                 775                 780

Thr Pro Leu Asp Leu Val Lys Glu Gly Asp Thr Asp Ile Gln Asp Leu
785                 790                 795                 800

Leu Arg Gly Asp Ala Ala Leu Leu Asp Ala Ala Lys Lys Gly Cys Leu
                805                 810                 815

Ala Arg Val Gln Lys Leu Cys Thr Pro Glu Asn Ile Asn Cys Arg Asp
            820                 825                 830

Thr Gln Gly Arg Asn Ser Thr Pro Leu His Leu Ala Ala Gly Tyr Asn
        835                 840                 845

Asn Leu Glu Val Ala Glu Tyr Leu Leu Glu His Gly Ala Asp Val Asn
    850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
            900                 905                 910

Lys Gly Arg Thr Gln Leu Cys Ala Leu Leu Leu Ala His Gly Ala Asp
        915                 920                 925

Pro Thr Met Lys Asn Gln Glu Gly Gln Thr Pro Leu Asp Leu Ala Thr
    930                 935                 940

Ala Asp Asp Ile Arg Ala Leu Leu Ile Asp Ala Met Pro Pro Glu Ala
```

```
              945                 950                 955                 960
Leu Pro Thr Cys Phe Lys Pro Gln Ala Thr Val Val Ser Ala Ser Leu
                965                 970                 975
Ile Ser Pro Ala Ser Thr Pro Ser Cys Leu Ser Ala Ala Ser Ser Ile
                980                 985                 990
Asp Asn Leu Thr Gly Pro Leu Ala Glu Leu Ala Val Gly Gly Ala Ser
                995                1000                1005
Asn Ala Gly Asp Gly Ala Ala Gly Thr Glu Arg Lys Glu Gly Glu
    1010                1015                1020
Val Ala Gly Leu Asp Met Asn Ile Ser Gln Phe Leu Lys Ser Leu
    1025                1030                1035
Gly Leu Glu His Leu Arg Asp Ile Phe Glu Thr Glu Gln Ile Thr
    1040                1045                1050
Leu Asp Val Leu Ala Asp Met Gly His Glu Glu Leu Lys Glu Ile
    1055                1060                1065
Gly Ile Asn Ala Tyr Gly His Arg His Lys Leu Ile Lys Gly Val
    1070                1075                1080
Glu Arg Leu Leu Gly Gly Gln Gln Gly Thr Asn Pro Tyr Leu Thr
    1085                1090                1095
Phe His Cys Val Asn Gln Gly Thr Ile Leu Leu Asp Leu Ala Pro
    1100                1105                1110
Glu Asp Lys Glu Tyr Gln Ser Val Glu Glu Glu Met Gln Ser Thr
    1115                1120                1125
Ile Arg Glu His Arg Asp Gly Gly Asn Ala Gly Gly Ile Phe Asn
    1130                1135                1140
Arg Tyr Asn Val Ile Arg Ile Gln Lys Val Val Asn Lys Lys Leu
    1145                1150                1155
Arg Glu Arg Phe Cys His Arg Gln Lys Glu Val Ser Glu Glu Asn
    1160                1165                1170
His Asn His His Asn Glu Arg Met Leu Phe His Gly Ser Pro Phe
    1175                1180                1185
Ile Asn Ala Ile Ile His Lys Gly Phe Asp Glu Arg His Ala Tyr
    1190                1195                1200
Ile Gly Gly Met Phe Gly Ala Gly Ile Tyr Phe Ala Glu Asn Ser
    1205                1210                1215
Ser Lys Ser Asn Gln Tyr Val Tyr Gly Ile Gly Gly Gly Thr Gly
    1220                1225                1230
Cys Pro Thr His Lys Asp Arg Ser Cys Tyr Ile Cys His Arg Gln
    1235                1240                1245
Met Leu Phe Cys Arg Val Thr Leu Gly Lys Ser Phe Leu Gln Phe
    1250                1255                1260
Ser Thr Met Lys Met Ala His Ala Pro Pro Gly His His Ser Val
    1265                1270                1275
Ile Gly Arg Pro Ser Val Asn Gly Leu Ala Tyr Ala Glu Tyr Val
    1280                1285                1290
Ile Tyr Arg Gly Glu Gln Ala Tyr Pro Glu Tyr Leu Ile Thr Tyr
    1295                1300                1305
Gln Ile Met Lys Pro Glu Ala Pro Ser Gly Thr Ala Thr Ala Ala
    1310                1315                1320
Glu Gln Lys Thr
    1325

<210> SEQ ID NO 7
```

<211> LENGTH: 1327
<212> TYPE: PRT
<213> ORGANISM: Homo sapiens

<400> SEQUENCE: 7

```
Met Ala Ala Ser Arg Arg Ser Gln His His His His His Gln Gln
1               5                   10                  15

Gln Leu Gln Pro Ala Pro Gly Ala Ser Ala Pro Pro Pro Pro Pro
            20                  25                  30

Pro Pro Leu Ser Pro Gly Leu Ala Pro Gly Thr Thr Pro Ala Ser Pro
        35                  40                  45

Thr Ala Ser Gly Leu Ala Pro Phe Ala Ser Pro Arg His Gly Leu Ala
50                  55                  60

Leu Pro Glu Gly Asp Gly Ser Arg Asp Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Pro Val Val Pro Ala Val Ser Thr Ser Ser
                100                 105                 110

Ala Ala Gly Val Ala Pro Asn Pro Ala Gly Ser Gly Ser Asn Asn Ser
            115                 120                 125

Pro Ser Ser Ser Ser Pro Thr Ser Ser Ser Ser Ser Pro Ser
130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

Gly Asp Val Ser Arg Val Lys Arg Leu Val Asp Ala Ala Asn Val Asn
        195                 200                 205

Ala Lys Asp Met Ala Gly Arg Lys Ser Ser Pro Leu His Phe Ala Ala
210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
            260                 265                 270

Ala Asp Pro Asn Ala Arg Asp Asn Trp Asn Tyr Thr Pro Leu His Glu
        275                 280                 285

Ala Ala Ile Lys Gly Lys Ile Asp Val Cys Ile Val Leu Leu Gln His
290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Arg Ile
370                 375                 380

Val Gln Leu Leu Leu Gln His Gly Ala Asp Val His Ala Lys Asp Lys
```

-continued

```
            385                 390                 395                 400
        Gly Gly Leu Val Pro Leu His Asn Ala Cys Ser Tyr Gly His Tyr Glu
                        405                 410                 415

Val Thr Glu Leu Leu Leu Lys His Gly Ala Cys Val Asn Ala Met Asp
                        420                 425                 430

Leu Trp Gln Phe Thr Pro Leu His Glu Ala Ala Ser Lys Asn Arg Val
                        435                 440                 445

Glu Val Cys Ser Leu Leu Leu Ser His Gly Ala Asp Pro Thr Leu Val
                450                 455                 460

Asn Cys His Gly Lys Ser Ala Val Asp Met Ala Pro Thr Pro Glu Leu
        465                 470                 475                 480

Arg Glu Arg Leu Thr Tyr Glu Phe Lys Gly His Ser Leu Leu Gln Ala
                        485                 490                 495

Ala Arg Glu Ala Asp Leu Ala Lys Val Lys Thr Leu Ala Leu Glu
                500                 505                 510

Ile Ile Asn Phe Lys Gln Pro Gln Ser His Glu Thr Ala Leu His Cys
                        515                 520                 525

Ala Val Ala Ser Leu His Pro Lys Arg Lys Gln Val Thr Glu Leu Leu
        530                 535                 540

Leu Arg Lys Gly Ala Asn Val Asn Glu Lys Asn Lys Asp Phe Met Thr
        545                 550                 555                 560

Pro Leu His Val Ala Ala Glu Arg Ala His Asn Asp Val Met Glu Val
                        565                 570                 575

Leu His Lys His Gly Ala Lys Met Asn Ala Leu Asp Thr Leu Gly Gln
                        580                 585                 590

Thr Ala Leu His Arg Ala Ala Leu Ala Gly His Leu Gln Thr Cys Arg
                        595                 600                 605

Leu Leu Leu Ser Tyr Gly Ser Asp Pro Ser Ile Ile Ser Leu Gln Gly
                        610                 615                 620

Phe Thr Ala Ala Gln Met Gly Asn Glu Ala Val Gln Gln Ile Leu Ser
        625                 630                 635                 640

Glu Ser Thr Pro Ile Arg Thr Ser Asp Val Asp Tyr Arg Leu Leu Glu
                        645                 650                 655

Ala Ser Lys Ala Gly Asp Leu Glu Thr Val Lys Gln Leu Cys Ser Ser
                        660                 665                 670

Gln Asn Val Asn Cys Arg Asp Leu Glu Gly Arg His Ser Thr Pro Leu
                        675                 680                 685

His Phe Ala Ala Gly Tyr Asn Arg Val Ser Val Val Glu Tyr Leu Leu
                        690                 695                 700

His His Gly Ala Asp Val His Ala Lys Asp Lys Gly Gly Leu Val Pro
        705                 710                 715                 720

Leu His Asn Ala Cys Ser Tyr Gly His Tyr Glu Val Ala Glu Leu Leu
                        725                 730                 735

Val Arg His Gly Ala Ser Val Asn Val Ala Asp Leu Trp Lys Phe Thr
                        740                 745                 750

Pro Leu His Glu Ala Ala Ala Lys Gly Lys Tyr Glu Ile Cys Lys Leu
                        755                 760                 765

Leu Leu Lys His Gly Ala Asp Pro Thr Lys Lys Asn Arg Asp Gly Asn
                        770                 775                 780

Thr Pro Leu Asp Leu Val Lys Glu Gly Asp Thr Asp Ile Gln Asp Leu
        785                 790                 795                 800

Leu Arg Gly Asp Ala Ala Leu Leu Asp Ala Ala Lys Lys Gly Cys Leu
                        805                 810                 815
```

```
Ala Arg Val Gln Lys Leu Cys Thr Pro Glu Asn Ile Asn Cys Arg Asp
                820                 825                 830

Thr Gln Gly Arg Asn Ser Thr Pro Leu His Leu Ala Ala Gly Tyr Asn
                835                 840                 845

Asn Leu Glu Val Ala Glu Tyr Leu Leu Glu His Gly Ala Asp Val Asn
            850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
                900                 905                 910

Lys Gly Arg Thr Gln Leu Cys Ala Leu Leu Leu Ala His Gly Ala Asp
                915                 920                 925

Pro Thr Met Lys Asn Gln Glu Gly Gln Thr Pro Leu Asp Leu Ala Thr
        930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                965                 970                 975

Ile Ser Pro Ala Ser Thr Pro Ser Cys Leu Ser Ala Ala Ser Ser Ile
                980                 985                 990

Asp Asn Leu Thr Gly Pro Leu Ala  Glu Leu Ala Val Gly  Gly Ala Ser
            995                 1000                1005

Asn Ala  Gly Asp Gly Ala Ala  Gly Thr Glu Arg Lys  Glu Gly Glu
    1010                1015                1020

Val Ala  Gly Leu Asp Met Asn  Ile Ser Gln Phe Leu  Lys Ser Leu
    1025                1030                1035

Gly Leu  Glu His Leu Arg Asp  Ile Phe Glu Thr Glu  Gln Ile Thr
    1040                1045                1050

Leu Asp  Val Leu Ala Asp Met  Gly His Glu Glu Leu  Lys Glu Ile
    1055                1060                1065

Gly Ile  Asn Ala Tyr Gly His  Arg His Lys Leu Ile  Lys Gly Val
    1070                1075                1080

Glu Arg  Leu Leu Gly Gly Gln  Gly Thr Asn Pro  Tyr Leu Thr
    1085                1090                1095

Phe His  Cys Val Asn Gln Gly  Thr Ile Leu Leu Asp  Leu Ala Pro
    1100                1105                1110

Glu Asp  Lys Glu Tyr Gln Ser  Val Glu Glu Met  Gln Ser Thr
    1115                1120                1125

Ile Arg  Glu His Arg Asp Gly  Gly Asn Ala Gly  Gly Ile Phe Asn
    1130                1135                1140

Arg Tyr  Asn Val Ile Arg Ile  Gln Lys Val Val  Asn Lys Lys Leu
    1145                1150                1155

Arg Glu  Arg Phe Cys His Arg  Gln Lys Glu Val Ser  Glu Glu Asn
    1160                1165                1170

His Asn  His His Asn Glu Arg  Met Leu Phe His Gly  Ser Pro Phe
    1175                1180                1185

Ile Asn  Ala Ile Ile His Lys  Gly Phe Asp Glu Arg  His Ala Tyr
    1190                1195                1200

Ile Gly  Gly Met Phe Gly Ala  Gly Ile Tyr Phe Ala  Glu Asn Ser
    1205                1210                1215
```

```
Ser Lys Ser Asn Gln Tyr Val Tyr Gly Ile Gly Gly Gly Thr Gly
    1220                1225               1230

Cys Pro Thr His Lys Asp Arg Ser Cys Tyr Ile Cys His Arg Gln
    1235                1240               1245

Met Leu Phe Cys Arg Val Thr Leu Gly Lys Ser Phe Leu Gln Phe
    1250                1255               1260

Ser Thr Met Lys Met Ala His Ala Pro Pro Gly His His Ser Val
    1265                1270               1275

Ile Gly Arg Pro Ser Val Asn Gly Leu Ala Tyr Ala Glu Tyr Val
    1280                1285               1290

Ile Tyr Arg Gly Glu Gln Ala Tyr Pro Glu Tyr Leu Ile Thr Tyr
    1295                1300               1305

Gln Ile Met Lys Pro Glu Ala Pro Ser Gln Thr Ala Thr Ala Ala
    1310                1315               1320

Glu Gln Lys Thr
    1325

<210> SEQ ID NO 8
<211> LENGTH: 1166
<212> TYPE: PRT
<213> ORGANISM: Homo sapiens

<400> SEQUENCE: 8

Met Ser Gly Arg Arg Cys Ala Gly Gly Ala Cys Ala Ser Ala
1               5                   10                  15

Ala Ala Glu Ala Val Glu Pro Ala Ala Arg Glu Leu Phe Glu Ala Cys
                20                  25                  30

Arg Asn Gly Asp Val Glu Arg Val Lys Arg Leu Val Thr Pro Glu Lys
            35                  40                  45

Val Asn Ser Arg Asp Thr Ala Gly Arg Lys Ser Thr Pro Leu His Phe
        50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Asp Gly Gly Leu Ile Pro Leu His
                85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
        115                 120                 125

His Glu Ala Ala Ile Lys Gly Lys Ile Asp Val Cys Ile Val Leu Leu
    130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
        195                 200                 205

Gly Arg Lys Ser Thr Pro Leu His Leu Ala Ala Gly Tyr Asn Arg Val
    210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255
```

```
Tyr Glu Val Thr Glu Leu Leu Val Lys His Gly Ala Cys Val Asn Ala
            260                 265                 270

Met Asp Leu Trp Gln Phe Thr Pro Leu His Glu Ala Ala Ser Lys Asn
            275                 280                 285

Arg Val Glu Val Cys Ser Leu Leu Ser Tyr Gly Ala Asp Pro Thr
    290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
                325                 330                 335

Gln Ala Ala Arg Glu Ala Asp Val Thr Arg Ile Lys Lys His Leu Ser
            340                 345                 350

Leu Glu Met Val Asn Phe Lys His Pro Gln Thr His Glu Thr Ala Leu
            355                 360                 365

His Cys Ala Ala Ala Ser Pro Tyr Pro Lys Arg Lys Gln Ile Cys Glu
    370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Val Lys His Glu Ala Lys Val Asn Ala Leu Asp Asn Leu
            420                 425                 430

Gly Gln Thr Ser Leu His Arg Ala Ala Tyr Cys Gly His Leu Gln Thr
            435                 440                 445

Cys Arg Leu Leu Leu Ser Tyr Gly Cys Asp Pro Asn Ile Ile Ser Leu
    450                 455                 460

Gln Gly Phe Thr Ala Leu Gln Met Gly Asn Glu Asn Val Gln Gln Leu
465                 470                 475                 480

Leu Gln Glu Gly Ile Ser Leu Gly Asn Ser Glu Ala Asp Arg Gln Leu
                485                 490                 495

Leu Glu Ala Ala Lys Ala Gly Asp Val Glu Thr Val Lys Lys Leu Cys
            500                 505                 510

Thr Val Gln Ser Val Asn Cys Arg Asp Ile Glu Gly Arg Gln Ser Thr
            515                 520                 525

Pro Leu His Phe Ala Ala Gly Tyr Asn Arg Val Ser Val Val Glu Tyr
    530                 535                 540

Leu Leu Gln His Gly Ala Asp Val His Ala Lys Asp Lys Gly Gly Leu
545                 550                 555                 560

Val Pro Leu His Asn Ala Cys Ser Tyr Gly His Tyr Glu Val Ala Glu
                565                 570                 575

Leu Leu Val Lys His Gly Ala Val Val Asn Val Ala Asp Leu Trp Lys
            580                 585                 590

Phe Thr Pro Leu His Glu Ala Ala Lys Gly Lys Tyr Glu Ile Cys
            595                 600                 605

Lys Leu Leu Leu Gln His Gly Ala Asp Pro Thr Lys Lys Asn Arg Asp
    610                 615                 620

Gly Asn Thr Pro Leu Asp Leu Val Lys Asp Gly Asp Thr Asp Ile Gln
625                 630                 635                 640

Asp Leu Leu Arg Gly Asp Ala Ala Leu Leu Asp Ala Ala Lys Lys Gly
                645                 650                 655

Cys Leu Ala Arg Val Lys Lys Leu Ser Ser Pro Asp Asn Val Asn Cys
            660                 665                 670
```

```
Arg Asp Thr Gln Gly Arg His Ser Thr Pro Leu His Leu Ala Ala Gly
            675                 680                 685

Tyr Asn Asn Leu Glu Val Ala Glu Tyr Leu Leu Gln His Gly Ala Asp
            690                 695                 700

Val Asn Ala Gln Asp Lys Gly Gly Leu Ile Pro Leu His Asn Ala Ala
705                 710                 715                 720

Ser Tyr Gly His Val Asp Val Ala Ala Leu Leu Ile Lys Tyr Asn Ala
                725                 730                 735

Cys Val Asn Ala Thr Asp Lys Trp Ala Phe Thr Pro Leu His Glu Ala
                740                 745                 750

Ala Gln Lys Gly Arg Thr Gln Leu Cys Ala Leu Leu Leu Ala His Gly
            755                 760                 765

Ala Asp Pro Thr Leu Lys Asn Gln Glu Gly Gln Thr Pro Leu Asp Leu
    770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
            820                 825                 830

Ser Ser Leu Ser Ala Ala Ser Ser Leu Asp Asn Leu Ser Gly Ser Phe
        835                 840                 845

Ser Glu Leu Ser Ser Val Val Ser Ser Ser Gly Thr Glu Gly Ala Ser
    850                 855                 860

Ser Leu Glu Lys Lys Glu Val Pro Gly Val Asp Phe Ser Ile Thr Gln
865                 870                 875                 880

Phe Val Arg Asn Leu Gly Leu Glu His Leu Met Asp Ile Phe Glu Arg
                885                 890                 895

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
            915                 920                 925

Gly Val Glu Arg Leu Ile Ser Gly Gln Gln Gly Leu Asn Pro Tyr Leu
930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Met Gln Ser Thr Val
                965                 970                 975

Arg Glu His Arg Asp Gly Gly His Ala Gly Gly Ile Phe Asn Arg Tyr
            980                 985                 990

Asn Ile Leu Lys Ile Gln Lys Val Cys Asn Lys Lys Leu Trp Glu Arg
            995                1000                1005

Tyr Thr His Arg Arg Lys Glu Val Ser Glu Glu Asn His Asn His
    1010                1015                1020

Ala Asn Glu Arg Met Leu Phe His Gly Ser Pro Phe Val Asn Ala
    1025                1030                1035

Ile Ile His Lys Gly Phe Asp Glu Arg His Ala Tyr Ile Gly Gly
    1040                1045                1050

Met Phe Gly Ala Gly Ile Tyr Phe Ala Glu Asn Ser Ser Lys Ser
    1055                1060                1065

Asn Gln Tyr Val Tyr Gly Ile Gly Gly Gly Thr Gly Cys Pro Val
    1070                1075                1080

His Lys Asp Arg Ser Cys Tyr Ile Cys His Arg Gln Leu Leu Phe
```

```
                    1085                1090                1095
Cys  Arg  Val  Thr  Leu  Gly  Lys  Ser  Phe  Leu  Gln  Phe  Ser  Ala  Met
         1100                1105                1110

Lys  Met  Ala  His  Ser  Pro  Pro  Gly  His  His  Ser  Val  Thr  Gly  Arg
         1115                1120                1125

Pro  Ser  Val  Asn  Gly  Leu  Ala  Leu  Ala  Glu  Tyr  Val  Ile  Tyr  Arg
         1130                1135                1140

Gly  Glu  Gln  Ala  Tyr  Pro  Glu  Tyr  Leu  Ile  Thr  Tyr  Gln  Ile  Met
         1145                1150                1155

Arg  Pro  Glu  Gly  Met  Val  Asp  Gly
         1160                1165

<210> SEQ ID NO 9
<211> LENGTH: 38
<212> TYPE: DNA
<213> ORGANISM: Artificial
<220> FEATURE:
<223> OTHER INFORMATION: Forward Primer

<400> SEQUENCE: 9
taagcagcta gcgccacctt ggagggcacg gccggcac                             38

<210> SEQ ID NO 10
<211> LENGTH: 48
<212> TYPE: DNA
<213> ORGANISM: Artificial
<220> FEATURE:
<223> OTHER INFORMATION: Reverse Primer

<400> SEQUENCE: 10
actatgggat cctcattctt tcaccagcct gtggatgtgg tgctgagc                  48

<210> SEQ ID NO 11
<211> LENGTH: 21
<212> TYPE: DNA
<213> ORGANISM: Artificial
<220> FEATURE:
<223> OTHER INFORMATION: shp53.1

<400> SEQUENCE: 11
gtccagatga agctcccaga a                                               21

<210> SEQ ID NO 12
<211> LENGTH: 21
<212> TYPE: DNA
<213> ORGANISM: Artificial
<220> FEATURE:
<223> OTHER INFORMATION: shp53.2

<400> SEQUENCE: 12
caccatccac tacaactaca t                                               21

<210> SEQ ID NO 13
<211> LENGTH: 21
<212> TYPE: DNA
<213> ORGANISM: Artificial
<220> FEATURE:
<223> OTHER INFORMATION: shScr

<400> SEQUENCE: 13
cctaaggtta agtcgccctc g                                               21

<210> SEQ ID NO 14
```

```
<211> LENGTH: 27
<212> TYPE: DNA
<213> ORGANISM: Artificial
<220> FEATURE:
<223> OTHER INFORMATION: Forward Primer

<400> SEQUENCE: 14
atggtggggg cagtgcctca caacctc                                          27

<210> SEQ ID NO 15
<211> LENGTH: 27
<212> TYPE: DNA
<213> ORGANISM: Artificial
<220> FEATURE:
<223> OTHER INFORMATION: Reverse Primer

<400> SEQUENCE: 15
gaggttgtga ggcactgccc ccaccat                                          27

<210> SEQ ID NO 16
<211> LENGTH: 29
<212> TYPE: DNA
<213> ORGANISM: Artificial
<220> FEATURE:
<223> OTHER INFORMATION: Forward Primer

<400> SEQUENCE: 16
cctccggttc atgctgccca tgcaggaac                                        29

<210> SEQ ID NO 17
<211> LENGTH: 29
<212> TYPE: DNA
<213> ORGANISM: Artificial
<220> FEATURE:
<223> OTHER INFORMATION: Reverse Primer

<400> SEQUENCE: 17
gttcctgcat gggcagcatg aaccggagg                                        29

<210> SEQ ID NO 18
<211> LENGTH: 27
<212> TYPE: DNA
<213> ORGANISM: Artificial
<220> FEATURE:
<223> OTHER INFORMATION: Forward Primer

<400> SEQUENCE: 18
gaggatgggc ctctggttca tgccgcc                                          27

<210> SEQ ID NO 19
<211> LENGTH: 27
<212> TYPE: DNA
<213> ORGANISM: Artificial
<220> FEATURE:
<223> OTHER INFORMATION: Reverse Primer

<400> SEQUENCE: 19
ggcggcatga accagaggcc catcctc                                          27

<210> SEQ ID NO 20
<211> LENGTH: 34
<212> TYPE: DNA
<213> ORGANISM: Artificial
<220> FEATURE:
<223> OTHER INFORMATION: Forward Primer

<400> SEQUENCE: 20
```

-continued aggacaggca caaacatgca cctcaaagct gttc                34

<210> SEQ ID NO 21
<211> LENGTH: 35
<212> TYPE: DNA
<213> ORGANISM: Artificial
<220> FEATURE:
<223> OTHER INFORMATION: Reverse Primer

<400> SEQUENCE: 21
gaacagcttt gaggtgcatg tttgtgcctg tcctg                35

<210> SEQ ID NO 22
<211> LENGTH: 19
<212> TYPE: DNA
<213> ORGANISM: Artificial
<220> FEATURE:
<223> OTHER INFORMATION: Forward Primer

<400> SEQUENCE: 22
ccaatgacaa cgcctcctg                19

<210> SEQ ID NO 23
<211> LENGTH: 19
<212> TYPE: DNA
<213> ORGANISM: Artificial
<220> FEATURE:
<223> OTHER INFORMATION: Reverse Primer

<400> SEQUENCE: 23
tggtgcagcc agaaagctc                19

<210> SEQ ID NO 24
<211> LENGTH: 21
<212> TYPE: DNA
<213> ORGANISM: Artificial
<220> FEATURE:
<223> OTHER INFORMATION: Forward Primer

<400> SEQUENCE: 24
agcctcgcat cctatacaac c                21

<210> SEQ ID NO 25
<211> LENGTH: 21
<212> TYPE: DNA
<213> ORGANISM: Artificial
<220> FEATURE:
<223> OTHER INFORMATION: Reverse Primer

<400> SEQUENCE: 25
ttctttcaca aggcggcact c                21

<210> SEQ ID NO 26
<211> LENGTH: 21
<212> TYPE: DNA
<213> ORGANISM: Artificial
<220> FEATURE:
<223> OTHER INFORMATION: Forward Primer

<400> SEQUENCE: 26
cacttctagc ccaccctgtg a                21

<210> SEQ ID NO 27
<211> LENGTH: 21
<212> TYPE: DNA

```
<213> ORGANISM: Artificial
<220> FEATURE:
<223> OTHER INFORMATION: Reverse Primer

<400> SEQUENCE: 27
ccacaggttc cgtaatgatt t                                              21

<210> SEQ ID NO 28
<211> LENGTH: 20
<212> TYPE: DNA
<213> ORGANISM: Artificial
<220> FEATURE:
<223> OTHER INFORMATION: Forward Primer

<400> SEQUENCE: 28
gtaacccgtt gaaccccatt                                                20

<210> SEQ ID NO 29
<211> LENGTH: 20
<212> TYPE: DNA
<213> ORGANISM: Artificial
<220> FEATURE:
<223> OTHER INFORMATION: Reverse Primer

<400> SEQUENCE: 29
ccatccaatc ggtagtagcg                                                20
```

UNITED STATES PATENT AND TRADEMARK OFFICE
CERTIFICATE OF CORRECTION

PATENT NO. : 11,273,151 B2
APPLICATION NO. : 15/773463
DATED : March 15, 2022
INVENTOR(S) : Aaronson et al.

Page 1 of 1

It is certified that error appears in the above-identified patent and that said Letters Patent is hereby corrected as shown below:

In the Claims

In Claim 5, Column 105, Line 62, delete "ef-an" and insert --an-- in it's place.

Signed and Sealed this
Twenty-sixth Day of July, 2022

Katherine Kelly Vidal
*Director of the United States Patent and Trademark Office*